United States Patent
Anderson et al.

(10) Patent No.: US 9,822,150 B2
(45) Date of Patent: Nov. 21, 2017

(54) NEISSERIA MENINGITIDIS COMPOSITIONS AND METHODS THEREOF

(71) Applicant: Pfizer Inc., New York, NY (US)

(72) Inventors: Annaliesa Sybil Anderson, Upper Saddle River, NJ (US); Rasappa Gounder Arumugham, Lansdale, PA (US); John Erwin Farley, Chapel Hill, NC (US); Leah Diane Fletcher, Geneseo, NY (US); Shannon Harris, Nanuet, NY (US); Kathrin Ute Jansen, New York, NY (US); Thomas Richard Jones, New City, NY (US); Lakshmi Khandke, Nanuet, NY (US); Bounthon Loun, Athens, GA (US); John Lance Perez, Doylestown, PA (US); Gary Warren Zlotnick, New Windsor, NY (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/470,922

(22) Filed: Aug. 27, 2014

(65) Prior Publication Data

US 2015/0071959 A1 Mar. 12, 2015

Related U.S. Application Data

(60) Provisional application No. 61/875,068, filed on Sep. 8, 2013, provisional application No. 61/926,717, filed on Jan. 13, 2014, provisional application No. 61/989,432, filed on May 6, 2014.

(51) Int. Cl.
| | |
|---|---|
| A61K 39/00 | (2006.01) |
| C07K 14/22 | (2006.01) |
| A61K 39/095 | (2006.01) |
| A61K 39/12 | (2006.01) |
| A61K 39/39 | (2006.01) |
| C12N 7/00 | (2006.01) |
| A61K 39/13 | (2006.01) |
| A61K 39/295 | (2006.01) |

(52) U.S. Cl.
CPC .......... *C07K 14/22* (2013.01); *A61K 39/0016* (2013.01); *A61K 39/095* (2013.01); *A61K 39/12* (2013.01); *A61K 39/13* (2013.01); *A61K 39/295* (2013.01); *A61K 39/39* (2013.01); *C12N 7/00* (2013.01); *A61K 2039/5252* (2013.01); *A61K 2039/545* (2013.01); *A61K 2039/55505* (2013.01); *A61K 2039/55511* (2013.01); *A61K 2039/70* (2013.01); *C12N 2710/20034* (2013.01); *C12N 2770/32634* (2013.01)

(58) Field of Classification Search
None
See application file for complete search history.

(56) References Cited

U.S. PATENT DOCUMENTS

| | | | |
|---|---|---|---|
| 4,376,110 A | 3/1983 | David et al. | |
| 4,554,101 A | 11/1985 | Hopp | |
| 4,650,764 A | 3/1987 | Temin et al. | |
| 4,666,829 A | 5/1987 | Glenner et al. | |
| 4,708,871 A | 11/1987 | Geyson | |
| 4,797,368 A | 1/1989 | Carter et al. | |
| 4,861,719 A | 8/1989 | Miller | |
| 4,912,094 A | 3/1990 | Myers et al. | |
| 4,925,792 A | 5/1990 | Rappuoli | |
| 4,980,289 A | 12/1990 | Temin et al. | |
| 5,057,540 A | 10/1991 | Kensil et al. | |
| 5,078,996 A | 1/1992 | Conlon, III et al. | |
| 5,124,263 A | 6/1992 | Temin et al. | |
| 5,139,941 A | 8/1992 | Muzyczka et al. | |
| 5,254,339 A | 10/1993 | Morein | |
| 5,399,346 A | 3/1995 | Anderson et al. | |
| 5,459,127 A | 10/1995 | Felgner et al. | |
| 5,514,581 A | 5/1996 | Ferrari et al. | |
| 5,550,213 A | 8/1996 | Anderson et al. | |

(Continued)

FOREIGN PATENT DOCUMENTS

| | | |
|---|---|---|
| AU | 2006318155 A1 | 11/2006 |
| AU | 2007263531 A1 | 6/2007 |

(Continued)

OTHER PUBLICATIONS

Anderson et al, Human Vaccines & Immunotherapeutics 9:3, 471-479; Mar. 2013.*
Deasy et al, Expert Rev. Vaccines, 2011, 10/3:335-343.*
Gasparini et al Expert Rev. Vaccines, 2014, 13/3:345-364.*
Harris et al, Human Vaccines 7: Supplement, 68-74; Jan./Feb. 2011.*
Jiang et al, Vaccine 28 (2010) 6086-6093.*
Konar et al, The Journal of Infectious Diseases 2013;208:627-36.*
Richmond et al, Vaccine 30 (2012) 6163-6174.*

(Continued)

*Primary Examiner* — Nita M. Minnifield
(74) *Attorney, Agent, or Firm* — Anna C. Chau

(57) ABSTRACT

In one aspect, the invention relates to a composition including a first polypeptide having the sequence set forth in SEQ ID NO: 1 and a second polypeptide having the sequence set forth in SEQ ID NO: 2. In one embodiment, the composition includes about 120 µg/ml of a first polypeptide including the amino acid sequence set forth in SEQ ID NO: 1, 120 µg/ml of a second polypeptide including the amino acid sequence set forth in SEQ ID NO: 2, about 2.8 molar ratio polysorbate-80 to the first polypeptide, about 2.8 molar ratio polysorbate-80 to the second polypeptide, about 0.5 mg/ml aluminum, about 10 mM histidine, and about 150 mM sodium chloride. In one embodiment, a dose of the composition is about 0.5 ml in total volume. In one embodiment, two-doses of the composition induce a bactericidal titer against diverse heterologous subfamily A and subfamily B strains in a human.

8 Claims, 2 Drawing Sheets

(56) References Cited

U.S. PATENT DOCUMENTS

| | | |
|---|---|---|
| 5,565,204 A | 10/1996 | Kuo et al. |
| 5,580,859 A | 12/1996 | Felgner et al. |
| 5,583,038 A | 12/1996 | Stover |
| 5,589,466 A | 12/1996 | Felgner et al. |
| 5,597,572 A | 1/1997 | Huergo et al. |
| 5,614,382 A | 3/1997 | Metcalf |
| 5,668,004 A | 9/1997 | O'Donnell |
| 5,723,127 A | 3/1998 | Scott et al. |
| 5,739,118 A | 4/1998 | Carrano et al. |
| 5,955,580 A | 9/1999 | Green et al. |
| 6,113,918 A | 9/2000 | Johnson et al. |
| 6,130,085 A | 10/2000 | Hamers et al. |
| 6,149,919 A | 11/2000 | Domenighini et al. |
| 6,165,995 A | 12/2000 | Hilgers |
| 6,207,646 B1 | 3/2001 | Krieg et al. |
| 6,245,892 B1 | 6/2001 | Oaks et al. |
| 6,270,775 B1 | 8/2001 | Cleary |
| 6,281,337 B1 | 8/2001 | Cannon-Carlson et al. |
| 6,299,884 B1 | 10/2001 | Van Nest et al. |
| 6,355,253 B1 | 3/2002 | Zlotnick |
| 6,355,255 B1 | 3/2002 | Cleary et al. |
| 6,610,310 B2 | 8/2003 | Hilgers |
| 6,951,653 B2 | 10/2005 | Cleary et al. |
| 7,115,730 B1 | 10/2006 | Pizza et al. |
| 7,118,757 B1 | 10/2006 | Seid et al. |
| 7,285,281 B2 | 10/2007 | Green et al. |
| 7,291,588 B2 | 11/2007 | Pizza et al. |
| 7,332,174 B2 | 2/2008 | Green et al. |
| 7,361,355 B2 | 4/2008 | Green et al. |
| 7,384,640 B1 | 6/2008 | Holmes et al. |
| 7,576,176 B1 | 8/2009 | Fraser et al. |
| 7,608,278 B2 | 10/2009 | Hoiseth et al. |
| 7,785,608 B2 | 8/2010 | Zlotnick et al. |
| 7,803,387 B2 | 9/2010 | Arico et al. |
| 7,820,789 B2 | 10/2010 | Kirkham et al. |
| 8,039,007 B2 | 10/2011 | Rappuoli et al. |
| 8,101,194 B2 | 1/2012 | Zlotnick et al. |
| 8,273,360 B2 | 9/2012 | Pizza et al. |
| 8,398,988 B2 | 3/2013 | Contorni et al. |
| 8,563,007 B1 | 10/2013 | Zlotnick et al. |
| 8,574,597 B2 | 11/2013 | Zlotnick |
| 8,632,995 B2 | 1/2014 | Sun et al. |
| 8,986,710 B2 | 3/2015 | Anderson et al. |
| 9,107,873 B2* | 8/2015 | Zlotnick .......... C07K 14/22 |
| 9,132,182 B2* | 9/2015 | Zlotnick .......... C07K 14/22 |
| 9,168,293 B2* | 10/2015 | Zlotnick .......... C07K 14/22 |
| 9,249,196 B2* | 2/2016 | Fraser .......... C07K 14/22 |
| 9,249,198 B2* | 2/2016 | Fraser .......... C07K 14/22 |
| 9,266,929 B2* | 2/2016 | Fraser .......... C07K 14/22 |
| 9,267,163 B2* | 2/2016 | Aric .......... C07K 14/22 |
| 9,724,402 B2* | 8/2017 | Anderson .......... A61K 39/095 |
| 2004/0110670 A1 | 6/2004 | Arico et al. |
| 2004/0167068 A1 | 8/2004 | Zlotnick et al. |
| 2004/0249125 A1 | 12/2004 | Pizza et al. |
| 2006/0251670 A1 | 11/2006 | Comanducci et al. |
| 2006/0257413 A1 | 11/2006 | Zlotnick et al. |
| 2007/0020622 A1 | 1/2007 | Lee et al. |
| 2007/0082007 A1 | 4/2007 | Zlotnick et al. |
| 2007/0148729 A1 | 6/2007 | Farley et al. |
| 2007/0253964 A1 | 11/2007 | Zlotnick et al. |
| 2009/0035328 A1 | 2/2009 | Granoff |
| 2009/0202593 A1 | 8/2009 | Zlotnick et al. |
| 2011/0076299 A1 | 3/2011 | Zlotnick et al. |
| 2011/0189187 A1 | 8/2011 | Zlotnick |
| 2011/0312510 A1 | 12/2011 | Mak et al. |
| 2012/0034261 A1 | 2/2012 | Zlotnick et al. |
| 2012/0070457 A1 | 3/2012 | Daugherty et al. |
| 2012/0093852 A1 | 4/2012 | Anderson et al. |
| 2012/0107339 A1 | 5/2012 | Granoff et al. |
| 2012/0301496 A1* | 11/2012 | Zlotnick .......... C07K 14/22 424/190.1 |
| 2012/0308595 A1* | 12/2012 | Zlotnick .......... C07K 14/22 424/190.1 |
| 2013/0171194 A1* | 7/2013 | Khandke .......... A61K 39/095 424/250.1 |
| 2013/0243807 A1* | 9/2013 | Anderson .......... C07K 16/1217 424/190.1 |
| 2014/0113329 A1 | 4/2014 | Sun et al. |
| 2015/0071959 A1* | 3/2015 | Anderson .......... A61K 39/0016 424/190.1 |
| 2015/0216960 A1 | 8/2015 | Zlotnick et al. |
| 2015/0335724 A1* | 11/2015 | Zlotnick .......... C07K 14/22 424/190.1 |
| 2016/0030543 A1* | 2/2016 | Zlotnick .......... C07K 16/1217 424/190.1 |

FOREIGN PATENT DOCUMENTS

| | | |
|---|---|---|
| CA | 2012311 C | 9/1990 |
| EP | 0125023 B1 | 11/1984 |
| EP | 0171496 B1 | 2/1986 |
| EP | 0173494 A2 | 3/1986 |
| EP | 0184187 A2 | 6/1986 |
| EP | 0185573 B1 | 6/1986 |
| EP | 0467714 A1 | 7/1991 |
| EP | 0178220 B1 | 1/1992 |
| EP | 0488528 B1 | 11/1995 |
| EP | 0453242 B1 | 8/1996 |
| EP | 1296713 B1 | 9/2003 |
| EP | 1326634 B1 | 4/2006 |
| EP | 2351767 A2 | 8/2011 |
| JP | 1144977 A | 6/1989 |
| WO | 86/01533 A1 | 3/1986 |
| WO | 87/01130 A1 | 2/1987 |
| WO | 87/002671 A1 | 5/1987 |
| WO | 89/07150 A1 | 8/1989 |
| WO | 90/02806 A1 | 3/1990 |
| WO | 90/10458 A1 | 9/1990 |
| WO | 91/18088 A1 | 11/1991 |
| WO | 92/05263 A1 | 4/1992 |
| WO | 92/19265 A1 | 11/1992 |
| WO | 93/09239 A1 | 5/1993 |
| WO | 94/12649 A2 | 6/1994 |
| WO | 94/21807 A2 | 9/1994 |
| WO | 94/26914 A1 | 11/1994 |
| WO | 94/28152 A1 | 12/1994 |
| WO | 94/28938 A1 | 12/1994 |
| WO | 95/02697 A1 | 1/1995 |
| WO | 95/07358 A1 | 3/1995 |
| WO | 95/18863 A1 | 7/1995 |
| WO | 95/21931 A1 | 8/1995 |
| WO | 95/22617 A1 | 8/1995 |
| WO | 95/26411 A2 | 10/1995 |
| WO | 95/28494 A1 | 10/1995 |
| WO | 96/10038 A1 | 4/1996 |
| WO | 96/14086 A1 | 5/1996 |
| WO | 96/17823 A1 | 6/1996 |
| WO | 96/22378 A1 | 7/1996 |
| WO | 96/25508 A1 | 8/1996 |
| WO | 96/29412 A1 | 9/1996 |
| WO | 96/39036 A1 | 12/1996 |
| WO | 96/40718 A1 | 12/1996 |
| WO | 97/19182 A1 | 5/1997 |
| WO | 98/08543 A1 | 3/1998 |
| WO | 98/08874 A1 | 3/1998 |
| WO | 98/17805 A2 | 4/1998 |
| WO | 99/01157 A1 | 1/1999 |
| WO | 99/01158 A1 | 1/1999 |
| WO | 99/01175 A1 | 1/1999 |
| WO | 99/10372 A1 | 3/1999 |
| WO | 99/24578 A2 | 5/1999 |
| WO | 99/27944 A1 | 6/1999 |
| WO | 99/36544 A2 | 7/1999 |
| WO | 99/40200 A1 | 8/1999 |
| WO | 99/48525 A1 | 9/1999 |
| WO | 99/55730 A2 | 11/1999 |
| WO | 99/55872 A1 | 11/1999 |
| WO | 99/57280 A2 | 11/1999 |
| WO | 99/61053 A1 | 12/1999 |
| WO | 00/18434 A1 | 4/2000 |
| WO | 00/22430 A2 | 4/2000 |
| WO | 00/42192 A1 | 7/2000 |
| WO | 00/43518 A1 | 7/2000 |

(56) References Cited

FOREIGN PATENT DOCUMENTS

| | | |
|---|---|---|
| WO | 00/44890 A1 | 8/2000 |
| WO | 00/45841 A2 | 8/2000 |
| WO | 00/50075 A2 | 8/2000 |
| WO | 00/57906 A1 | 10/2000 |
| WO | 00/66741 A2 | 11/2000 |
| WO | 00/66791 A1 | 11/2000 |
| WO | 00/71574 A2 | 11/2000 |
| WO | 00/71725 A2 | 11/2000 |
| WO | 01/04316 A2 | 1/2001 |
| WO | 01/31019 A2 | 5/2001 |
| WO | 01/37863 A2 | 5/2001 |
| WO | 01/38350 A2 | 5/2001 |
| WO | 01/41800 A2 | 6/2001 |
| WO | 01/52885 A1 | 7/2001 |
| WO | 01/64920 A2 | 9/2001 |
| WO | 01/64922 A2 | 9/2001 |
| WO | 02/058737 A2 | 8/2002 |
| WO | 02/079243 A2 | 10/2002 |
| WO | 02/079246 A2 | 10/2002 |
| WO | 02/083710 A2 | 10/2002 |
| WO | 02/083711 A2 | 10/2002 |
| WO | 02/098368 A2 | 12/2002 |
| WO | 02/098369 A2 | 12/2002 |
| WO | 03/007985 A2 | 1/2003 |
| WO | 03/009869 A1 | 2/2003 |
| WO | 03/020756 A2 | 3/2003 |
| WO | 03/063766 A2 | 8/2003 |
| WO | WO 2003/063766 A2 * | 8/2003 |
| WO | 2003/080678 A1 | 10/2003 |
| WO | 2003/094834 A2 | 11/2003 |
| WO | 2003/094960 A2 | 11/2003 |
| WO | 2004/019977 A2 | 3/2004 |
| WO | 2004/019992 A1 | 3/2004 |
| WO | 2004/032958 A1 | 4/2004 |
| WO | 2004/046177 A2 | 6/2004 |
| WO | 2004/048404 A2 | 6/2004 |
| WO | 2004/065603 A2 | 8/2004 |
| WO | 2004/067030 A2 | 8/2004 |
| WO | 2004/067033 A1 | 8/2004 |
| WO | 2004/083251 A2 | 9/2004 |
| WO | 2004/094596 A2 | 11/2004 |
| WO | 2005/000345 A2 | 1/2005 |
| WO | 2005/004908 A1 | 1/2005 |
| WO | 2005/020964 A1 | 3/2005 |
| WO | 2005/032583 A2 | 4/2005 |
| WO | 2005/033148 A1 | 4/2005 |
| WO | 2005/065708 A1 | 7/2005 |
| WO | 2005/090986 A2 | 9/2005 |
| WO | 2005/102384 A2 | 11/2005 |
| WO | 2005/103230 A2 | 11/2005 |
| WO | 2005/105140 A2 | 11/2005 |
| WO | 2005/105141 A2 | 11/2005 |
| WO | 2005/108580 A1 | 11/2005 |
| WO | 2005/113607 A2 | 12/2005 |
| WO | 2006/000920 A2 | 1/2006 |
| WO | 2006/011060 A2 | 2/2006 |
| WO | 2006/024954 A2 | 3/2006 |
| WO | 2006/027685 A2 | 3/2006 |
| WO | 2006/046143 A2 | 5/2006 |
| WO | 2006/067632 A2 | 6/2006 |
| WO | 2006/075170 A1 | 7/2006 |
| WO | 2006/081259 A2 | 8/2006 |
| WO | 2006/096701 A2 | 9/2006 |
| WO | 2006/120576 A2 | 11/2006 |
| WO | 2007/000314 A2 | 1/2007 |
| WO | 2007/000341 A2 | 1/2007 |
| WO | 2007/000342 A2 | 1/2007 |
| WO | 2007/000343 A2 | 1/2007 |
| WO | 2007/026249 A2 | 3/2007 |
| WO | 2007/028408 A1 | 3/2007 |
| WO | 2007/060548 A2 | 5/2007 |
| WO | 2007/071786 A2 | 6/2007 |
| WO | 2007/127665 | 8/2007 |
| WO | 2007/111940 A2 | 10/2007 |
| WO | 2007/127665 A2 | 11/2007 |
| WO | 2007/127668 A2 | 11/2007 |
| WO | 2007/144316 A2 | 12/2007 |
| WO | 2007/144317 A2 | 12/2007 |
| WO | 2008/001222 A2 | 1/2008 |
| WO | 2008/001224 A2 | 1/2008 |
| WO | 2008/013943 A2 | 1/2008 |
| WO | 2008/079372 A2 | 7/2008 |
| WO | 2008/084411 A2 | 7/2008 |
| WO | 2008/149238 A2 | 12/2008 |
| WO | 2009/010877 A2 | 1/2009 |
| WO | 2009/016515 A2 | 2/2009 |
| WO | 2009/050586 A1 | 4/2009 |
| WO | 2009/104097 A2 | 8/2009 |
| WO | 2005/090985 A1 | 9/2009 |
| WO | 2009/109550 A1 | 9/2009 |
| WO | 2009/114485 A2 | 9/2009 |
| WO | 2009/143168 A2 | 11/2009 |
| WO | 2009/158142 A1 | 12/2009 |
| WO | 2010/027872 A1 | 3/2010 |
| WO | 2010/028096 A2 | 3/2010 |
| WO | 2010/028859 A1 | 3/2010 |
| WO | 2010/067202 A2 | 6/2010 |
| WO | 2010/070453 A2 | 6/2010 |
| WO | 2010/109323 A1 | 9/2010 |
| WO | 2010/109324 A1 | 9/2010 |
| WO | 2010/127172 A2 | 11/2010 |
| WO | 2011/024072 A2 | 3/2011 |
| WO | 2011/039631 A2 | 4/2011 |
| WO | 2011/042516 A2 | 4/2011 |
| WO | 2011/051893 A1 | 5/2011 |
| WO | 2011/080595 A2 | 7/2011 |
| WO | 2011/110531 A2 | 9/2011 |
| WO | 2011/110634 A1 | 9/2011 |
| WO | 2011/110635 A1 | 9/2011 |
| WO | 2011/126863 A1 | 10/2011 |
| WO | 2011/161653 A1 | 12/2011 |
| WO | 2012/020326 A1 | 2/2012 |
| WO | 2012/025873 A2 | 3/2012 |
| WO | 2012/031271 A1 | 3/2012 |
| WO | 2012/032169 A1 | 3/2012 |
| WO | 2012/032489 A1 | 3/2012 |
| WO | 2012/032498 A2 | 3/2012 |
| WO | 2012/035519 A1 | 3/2012 |
| WO | WO 2012/032489 A1 * | 3/2012 |
| WO | 2003/047619 A1 | 6/2013 |
| WO | 2013/132452 A2 | 9/2013 |
| WO | WO 2013/132452 A2 * | 9/2013 |
| WO | 2014/136064 A2 | 9/2014 |
| WO | WO 2014/136064 A2 * | 9/2014 |
| WO | 2015/033251 A2 | 3/2015 |
| WO | WO 2015/033251 A1 * | 3/2015 |

OTHER PUBLICATIONS

Sheldon et al, Human Vaccines & Immunotherapeutics 8:7, 888-895; Jul. 2012.*
Wang et al, Vaccine 29 (2011) 4739-4744.*
Vesikari et al, Journal of the Pediatric Infectious Diseases Society, (Jan. 23, 2016). pp. 1-8, Electronic Publication Date: Jan. 23, 2016.*
Vesikari et al, Journal of the Pediatric Infectious Diseases Society, (Aug. 4, 2015). pp. 1-9, Electronic Publication Date: Aug. 4, 2015.*
McNeill et al, Microbiol and MOlecular Biol Reviews, 2013, 77/2:234-252.*
Aasel et al., "Most antibodies to PorB and Rmp do not bind to viable meningococci, but bind strongly to ethanol-killed bacteria", Abstract from the 11th International Pathogenic Neisseria Conference (Nice France, Nov. 1-6, 1998), pp. 37-38 (http://neisseria.org/ipnc/history.shtml).
Abdillahi et al, "Whole-cell ELISA for typing Neisseria meningitidis with monoclonal antibodies", FEMS Microbiology Letters 48:367-371 (1987).
Abdillahi et al, "Neisseria meningitidis group B serosubtyping using monoclonal antibodies in whole-cell Elisa", Microbial Pathogenesis 4:27-32 (1988).
Achtman, "Epidemic spread and antigenic variability of Neisseria meningitidis", Trends in Microbiology 3(5):186-192 (1995).
Alm et al, "Genomic-sequence comparison of two unrelated isolates of the human gastric pathogen Helicobacter pylori", Nature 397:176-180 (1999).

(56) References Cited

OTHER PUBLICATIONS

Altschul et al, "Basic Local Alignment Search Tool", J. Mol. Biol. 215:403-410 (1990).
Altschul et al, "Protein database searches for multiple alignments", Proc. Natl. Acad. Sci. 87:5509-5513 (1990).
Altschul et al, "Gapped BLAST and PSI-BLAST: a new generation of protein database search programs", Nucleic Acids Research 25(17): 3389-3402 (1997).
Ambrosch et al, "Immunogenicity and side-effects of a new tetravalent meningococcal polysaccharide vaccine", Bulletin of the World Health Organization 61(2):317-323 (1983).
Andersen, et al, "Immune Responses to Meningococcal Outer Membrane Vesicles After Intranasal Immunisation", Twelfth International Pathogenic Neisseria Conference, Nov. 12-17, 2000, Galveston, Texas (Abstract #057).
Anderson, "Techniques for the preservation of three-dimensional structure in preparing specimens for the electron microscope", Transactions of the New York Academy of Sciences, 13:130-134 (1951).
Anderson et al; "Potential Impact of the Bivalent rLP2086 Vaccine on Neisseria meningitidis Invasive Disease and Carriage Isolates in Two Adolescent Populations"; poster presented at the 30th Annual Meeting of the European Society for Paediatric Infectious Diseases; May 8-12, 2012; Thessaloniki, Greece; http://epostersonline.s3.amazonaws.com/espid2012/espid2012.02400cf.NORMAL.pdf, May 12, 2012.
Ausubel et al, Current Protocols in Molecular Biology, Sections 2.10, 6.3 & 6.4 (1995).
Bantam Medical Dictionary, Third Edition, pp. 302-303 (2000).
Barbour et al, "New tricks of tick-borne pathogen", Nature 390:553 & 555 (1997).
Bateman et al, "The Pfam Protein Families Database", Nucleic Acids Research 28(1):263-266 (2000).
Beard et al, "Transcription Mapping of Mouse Adenovirus Type 1 Early Region 3", Virology 175:81-90 (1990).
Bender et al, "Evidence that the Packaging Signal of Moloney Murine Leukemia Virus Extends into the gag Region", Journal of Virology 61(5):1639-1646 (1987).
Benson, "Tandem repeats finder: a program to analyze DNA sequences", Nucleic Acids Research 27(2):573-580 (1999).
Bernfield et al., "Identification of a novel vaccine candidate for group B Neisseria meningitidis", Abstracts of the Thirteenth International Pathogenic Neisseria Conference, (Ed) Caugant et al. Oslo, Norway, p. 116, Sep. 1-6, 2002.
Bernstein et al, "Gene Transfer with Retrovirus Vectors", Genet. Eng. 7:235-261 (1985).
Better et al, Escherichia coli Secretion of an Active Chimeric Antibody Fragment, Science 240:1041-1043 (1988).
Beuvery et al, "Preparation and Immunochemical Characterization of Meningococcal Group C Polysaccharide-Tetanus Toxoid Conjugates as a New Generation of Vaccines", Infection and Immunity 40(1):39-45 (1983).
Beuvery et al, "Preparation and Physicochemical and Immunological Characterization of Polysaccharide-Outer Membrane Protein Complexes of Neisseria meningitidis", Infection and Immunity 40(1):369-380 (1983).
Biocomputing: Informatics and Genome Projects, Smith D.W., ed., Academic Press, New York (1994).
Bjune, et al., "Effect of Outer Membrane Vesicle Vaccine Against Group B Meningococcal Disease in Norway", The Lancet, 338(8775):1093-1096 (1991).
Boslego et al, "Chapter 17: Gonorrhea Vaccines", Vaccines and Immunotherapy, SJ Cryz Jr. ed., Pergamon Press, pp. 211-223 (1991).
Boulianne et al, "Production of functional chimaeric mouse/human antibody", Nature 312:643-646 (1984).
Brown, "Hybridization Analysis of DNA Blots", Current Protocols in Molecular Biology, Supp. 21, 2.10.1-2.10.16 (1993).
Cabilly et al, "Generation of antibody activity from immunoglobulin polypeptide chains produced in Escherichia coli", Proc. Natl. Acad. Sci. 81:3273-3277 (1984).
Cannon, "Conserved Lipoproteins of Pathogenic Neisseria Species Bearing the H.8 Epitope: Lipid-Modified Azurin and H.8 Outer Membrane Protein", Clinical Microbiology Reviews 2(Suppl):S1-S4 (1989).
Cantini et al, "Solution Structure of the Immunodominant Domain of Protective Antigen GNA1870 of Neisseria meningitidis", The Journal of Biological Chemistry 281(11):7220-7227 (2006).
Carillo et al, "The Multiple Sequence Alignment Problem in Biology", SIAM J. Appl. Math. 48(5):1073-1082 (1988).
Chao et al, "Endocarditis due to Neisseria sicca: Report of One Case", Acta Paed Sin 38(3):229-231 (1997).
Chen et al, "Cloning and Expression of the Streptococcal C5a Peptidase Gene in Escherichia coli: Linkage to the Type 12 M Protein Gene", Infection and Immunity 57(6):1740-1745 (1989).
Chen et al., "Determination of the Optimal Aligned Spacing Between the Shine—Dalgarno Sequence and the Translation Initiation Codon of Escherichia coli mRNAs", Nucleic Acids Research 22(23):4953-4957 (1994).
Chmouryguina et al, "Conservation of the C5a Peptidase Genes in Group A and B Streptococci", Infection and Immunity 64(7):2387-2390 (1996).
Cockerill et al, "Molecular, Serological, and Clinical Features of 16 Consecutive Cases of Invasive Streptococcal Disease", Clinical Infectious Diseases 26:1448-1458 (1998).
Computational Molecular Biology: Sources and Methods for Sequence Analysis, Lesk A.M. et, Oxford University Press, New York, 1988.
Courtney et al, "Cloning, Sequencing, and Expression of a Fibronectin/Fibrinogen-Binding Protein from Group A Streptococci", Infection and Immunity 62(9):3937-3946 (1994).
Cserzo et al, "Prediction of transmembrane alpha-helices in prokaryotic membrane proteins: the dense alignment surface method", Protein Engineering 10(6):673-676 (1997).
Cunningham et al, "Immunological Crossreactivity Between the Class I Epitope of Streptococcal M Protein and Myosin", Adv Exp Med Biol 418:887-892 (1997).
Curiel et al, "High-Efficiency Gene Transfer Mediated by Adenovirus Coupled to DNA-Polylysine Complexes", Human Gene Therapy 3:147-154 (1992).
Curriculum Vitae of Professor Paul M. Dunman, Ph.D., submitted in Opposition Proceedings against Novartis EP 1 645 631 on Sep. 14, 2011.
Curriculum Vitae of Lakshmi Khandke, Ph.D., submitted in Opposition Proceedings against Novartis EP1409013 on Nov. 18, 2011.
Dale et al, "Passive Protection of Mice Against Group A Streptococcal Pharyngeal Infection by Lipoteichoic Acid", The Journal of Infectious Diseases 169:319-323 (1994).
Dale et al, "Hyaluronate Capsule and Surface M Protein in Resistance to Opsonization of Group A Streptococci", Infection and Immunity 64(5):1495-1501 (1996).
Dale et al, "Recombinant, octavalent group A streptococcal M protein vaccine", Vaccine 14(10):944-948 (1996).
Database EMBL [Online] EBI, Kohara, Y., "Caenorhabiditis elegans cDNA clone yk26f2: 5' end, single read," Database accession No. D35881 (Aug. 13, 1994).
Database Geneseq 'Online', "Neisseria meningitidis ORF 741 protein sequence Seq ID No. 2536", XP002320506, Mar. 21, 2000.
Database Geneseq 'Online', "N. gonorrhoeae amino acid sequence SEQ ID 1586", XP002320505, Mar. 7, 2003.
Database Geneseq Online, "Neisseria meningitides ORF2086 protein-encoding gene SedID61" AAY75530, Jan. 29, 2004.
Database Geneseq Online, "Neisseria meningitides ORF2086 protein-encoding gene SedID61" AAZ54292-NT, Jan. 29, 2004.
Database UniPro 'Online', "Hypothetical Protein NMB1870", XP002308111, Oct. 1, 2000.
Database UniProt 'Online', "Putative lipoprotein N meningitidis (Serotype A)", XP002320503, Oct. 1, 2000.
Datasheet for MENCEVAX™, International Data Sheet version 2.1 (May 15, 2000).

(56) References Cited

OTHER PUBLICATIONS

Datasheet for MENOMUNE™, product information as of Feb. 2001.
Datasheet for MeNZB® vaccine product prepared Jun. 23, 2009.
De et al, "Purification and characterization of *Streptococcus pneumoniae* palmitoylated pneumococcal surface adhesin a expressed in *Escherichia coli*", Vaccine 18:1811-1821 (2000).
Declaration by Dr. Julian Parkhill, submitted in Opposition Proceedings against Novartis EP1645631 on Jul. 23, 2008.
Declaration of Dr. Ellen Murphy, submitted in Opposition Proceedings against Novartis EP 1 645 631 on Sep. 14, 2011.
Declaration by Professor Paul Dunman, submitted in Opposition Proceedings against Novartis EP1645631 on Sep. 14, 2011.
Declaration of Emilio A. Emini, Ph.D., submitted in Opposition Proceedings against Novartis EP1645631 on Nov. 3, 2011.
Declaration of Lakshmi Khandke, Ph.D., submitted in Opposition Proceedings against Novartis EP1409013 on Dec. 21, 2011.
Definition of "epitope" from Henderson's Dictionary of Biological Terms, 11th edition, Eleanor Lawrence ed., pp. 37, 184 and cover pages (1997).
Delgado et al., "Lipoprotein NMB0928 from Neisseria meningitidis Serogroup B as a Novel Vaccine Candidate", Vaccine 25:8420-8431 (2007).
Dempsey et al., "The physical map of the chromosome of a serogroup a strain of Neisseria meningitidis shows complex rearrangements relative to the chromosomes of the two mapped strains of the closely related species *N. gonorrhoeae*," Journal of Bacteriology 177(22):6390-6400 (1995).
Devereux et al, "A comprehensive set of sequence analysis programs for the VAX", Nucleic Acids Research 12(1):387-395 (1984).
Duby et al, "Using Synthetic Oligonucleotides as Probes", Current Protocols in Molecular Biology, Supp. 2, 6.4.1-6.4.10 (1993).
Eddy, "Hidden Markov models", Current Opinion in Structural Biology 6:361-365 (1996).
Ellen et al, "M Protein-Associated Adherence of *Streptococcus pyogenes* to Epithelial Surfaces: Prerequisite for Virulence", Infection and Immunity 5(5):826-830 (1972).
Ellis, "New Technologies for Making Vaccines", Vaccines, Plotkin et al. editors, W.B. Saunders Company, Philadelphia, Chapter 29, pp. 568-575 (1988).
Eng et al, "An Approach to Correlate Tandem Mass Spectral Data of Peptides with Amino Acid Sequences in a Protein Database", J Am Soc Mass Spectrom 5:976-989 (1994).
EP Application No. 07075161.5 Response to Communication dated Oct. 28, 2009.
Erdile et al, "Role of Attached Lipid in Immunogenicity of Borrelia burgdorferi OspA", Infection and Immunity 61(1):81-90 (1993).
Farley et al., "Characterization, cloning and expression of different subfamilies of the ORF2086 gene from Neisseria meningitidis", Abstracts of the Thirteenth International Pathogenic Neisseria Conference, (Ed) Caugant et al., Oslo, Norway, p. 124, Sep. 1-6, 2002.
Feavers et al, "Meningococcal protein antigens and vaccines", Vaccine 275:B42-B50 (2009).
Felgner et al, "Lipofection: A highly efficient, lipid-mediated DNA-transfection procedure", Proc. Natl. Acad. Sci. 84:7413-7417 (1987).
Felgner et al, "Cationic liposome-mediated transfection", Nature 337:387-388 (1989).
Final Written Submission in Preparation of Oral Proceedings in Opposition against Novartis EP 1 645 631 submitted Sep. 14, 2011.
Fischetti et al, "Conservation of a hexapeptide sequence in the anchor region of surface proteins from Gram-positive cocci", Molecular Microbiology 4(9):1603-1605 (1990).
Fleischmann et al, "Whole-Genome Random Sequencing and Assembly of Haemophilus influenzae Rd", Science 269:496-501 (1995).
Fletcher et al, "Vaccine Potential of the Neisseria meningitidis 2086 Lipoprotein", Infection and Immunity 72(4):2088-2100 (2004).

Fogg et al,"Constitutive Expression of Fibronectin Binding in *Streptococcus pyogenes* as a Result of Anaerobic Activation of rofA", Journal of Bacteriology 179(19):6172-6180 (1997).
Fontana et al, "A genomic approach to identify vaccine candidates against gonococcus", Abstract from the 13th International Pathogenic Neisseria Conference, Oslo Norway, Sep. 1-6, 2002, p. 248 (http://neisseria.org/ipnc/history.shtml).
Foster et al, "Surface protein adhesins of *Staphylococcus aureus*", Trends in Microbiology 6(12):484-488 (1998).
Fraser et al, "Genomic sequence of a Lyme disease spirochaete, Borrelia burgdorferi", Nature 390:580-591 (1997).
Fredriksen et al, "Production, Characterization and Control of MenB-Vaccine <<Folkehelsa>>: An Outer Membrane Vesicle Vaccine Against Group B Meningococcal Disease", NIPH Annals 14(2):67-80 (1991).
Fukasawa et al, "Neisseria meningitidis serogroup C polysaccharide and serogroup B outer membrane vesicle conjugate as a bivalent meningococcus vaccine candidate", Vaccine 17:2951-2958 (1999).
Gentz et al, "Bioassay for trans-activation using purified human immunodeficiency virus tat-encoded protein: Trans-activation requires mRNA synthesis", Proc. Natl. Acad. Sci. 86:821-824 (1989).
Giuliani et al, "The Region Comprising Amino Acids 100 to 255 of Neisseria meningitidis Lipoprotein GNA 1870 Elicits Bactericidal Antibodies", Infection and Immunity 73(2):1151-1160 (2005).
Giuliani et al, "A universal vaccine for serogroup B meningococcus" Proc Natl Acad Sci 103(29):10834-10839 (2006).
Gold et al., "Chapter 78. Translational Initiation", *Escherichia Coli* and *Salmonella typhimurium*: Cellular and Molecular Biology, Ed. Neidhardt FC, vol. 2, pp. 1302-1307 (1987).
Goldschneider et al, "Human Immunity to the Meningococcus I. The Role of Humoral Antibodies", Journal of Experimental Medicine 129(6):1307-1326 (1969).
Goldschneider et al, "Human Immunity to the Meningococcus II. Development of Natural Immunity", Journal of Experimental Medicine 129(6):1327-1348 (1969).
Gomez et al, "The Bacillus subtilis lipoprotein LpIA causes cell lysis when expressed in *Escherichia coli*", Microbiology 140:1839-1845 (1994).
Gotschlich et al, "Human Immunity to the Meningococcus. IV. Immunogenicity of Group A and Group C Meningococcal Polysaccharides in Human Volunteers", Journal of Experimental Medicine 129(6):1367-1384 (1969).
Gotschlich et al, "Human Immunity to the Meningococcus. V. The Effect of Immunization with Meningococcal Group C Polysaccharide on the Carrier State", Journal of Experimental Medicine 129(6):1385-1395 (1969).
Graham et al, "Characteristics of a Human Cell Line Transformed by DNA from Human Adenovirus Type 5", J. Gen. Virology 36:59-72 (1977).
Graham, "Covalently closed circles of human adenovirus DNA are infectious", The EMBO Journal 3(12):2917-2922 (1984).
Grandi, "Reverse Vaccinology: A Critical Analysis", Encyclopedia of Genetics, Genomics, Proteomics and Bioinformatics, pp. 1320-1330 (2005).
Green et al, "The e (P4) Outer Membrane Protein of Haemophilus influenzae: Biologic Activity of Anti-e Serum and Cloning and Sequencing of the Structural Gene", Infection and Immunity 59(9):3191-3198 (1991).
Greenspan et al, "Defining epitopes: It's not as easy as it seems", Nature Biotechnology 17:936-937 (1999).
Griffin et al, "Computer Analysis of Sequence Data", Methods in Molecular Biology, vol. 24, Part 1, Chapter 1, Humana Press, New Jersey (1994).
Gupta, "Aluminum compounds as vaccine adjuvants", Advanced Drug Delivery Reviews 32(3):155-172 (1998).
Guzman et al, "Tight Regulation, Modulation, and High-Level Expression by Vectors Containing the Arabinose PBAD Promoter", Journal of Bacteriology 177(14):4121-4130 (1995).
Hacker et al, "Pathogenicity islands of virulent bacteria: structure, function and impact on microbial evolution", Molecular Microbiology 23(6):1089-1097 (1997).

(56) References Cited

OTHER PUBLICATIONS

Hanski et al, "Expression of protein F, the fibronectin-binding protein of *Streptococcus pyogenes* JRS4, in heterologous streptococcal and enterococcal strains promotes their adherence to respiratory epithelial cells", Infection and Immunity 60(12):5119-5125 (1992).

Hanski et al, "Protein F, a fibronectin-binding protein, is an adhesin of the group A streptococcus *Streptococcus pyogenes*", Proc. Natl. Acad. Sci. 89:6172-6176 (1992).

Hansson et al, "Expression of Truncated and Full-Length Forms of the Lyme Disease Borrelia Outer Surface Protein A in *Escherichia coli*", Protein Expression and Purification 6:15-24 (1995).

Hayashi et al, "Lipoproteins in Bacteria", Journal of Bioenergetics and Biomembranes 22(3):451-471 (1990).

Hem et al, "Chapter 9: Structure and Properties of Aluminum-Containing Adjuvants", Vaccine Design: The Subunit and Adjuvant Approach, Plenum Press, New York, pp. 249-276 (1995).

Hernandez-Sanchez et al, "Lambda bar minigene-mediated inhibition of protein synthesis involves accumulation of peptidyl-tRNA and starvation for tRNA", The EMBO Journal 17(13):3758-3765 (1998).

Hornyik et al, "Cerebrospinal Fluid Shunt Infection by Neisseria sicca", Pediatr Neurosurg 21:189-191 (1994).

Houghten, "General Method for the rapid solid-phase synthesis of large numbers of peptides: Specificity of antigen-antibody interaction at the level of individual amino acids", Proceedings of the National Academy of Sciences of USA 82:5131-5135 (1985).

Huang et al, "The streptokinase gene of group a streptococci: cloning, expression in *Escherichia coli*, and sequence analysis", Molecular Microbiology 3(2):197-205 (1989).

Hung, "The Neisseria meningitidis Macrophage Infectivity Potentiator Protein Induces Cross-Strain Serum Bactericidal Activity and is a Potential Serogroup B Vaccine Candidate", Infection and Immunity, 79(9):3784-3791 (2011).

Hynes et al, "Analysis of a Second Bacteriophage Hyaluronidase Gene from *Streptococcus pyogenes*: Evidence for a Third Hyaluronidase Involved in Extracellular Enzymatic Activity", Infection and Immunity 63(8):3015-3020 (1995).

Hynes et al, "The extracellular hyaluronidase gene (hylA) of *Streptococcus pyogenes*", FEMS Microbiology Letters 184:109-112 (2000).

Interlocutory Decision of the Opposition Division in Opposition against Novartis EP 1 645 631 dated May 21, 2012.

Isberg et al, "Binding and internalization of microorganisms by integrin receptors", Trends in Microbiology 2(1):10-14 (1994).

Jackson et al, U.S. Appl. No. 60/098,685, filed Sep. 1, 1998.

Jiang et al, "Broad vaccine coverage predicted for a bivalent recombinant factor H binding protein based vaccine to prevent serogroup B meningococcal disease", Vaccine 28:6086-6093 (2010).

Johnson et al., "Analysis of the Human Ig Isotype Response to Lactoferrin Binding Protein A from Neisseria meningitidis", FEMS Immunology and Medical Microbiology 25(4):349-354 (1999).

Jones et al, "The Importance of the Location of Antibody Binding on the M6 Protein for Opsonization and Phagocytosis of Group A M6 Streptococci", J. Exp. Med. 167:1114-1123 (1988).

JVCI-CMR website showing Z2491 Sanger sequence (http://cmr.jvci.org/tigr-scripts/CMR/shared/Genomes.cgi and links) printed on Jul. 1, 2010.

Kafri et al, "A Packaging Cell Line for Lentivirus Vectors", Journal of Virology 73(1):576-584 (1999).

Kaplitt et al, "Expression of a Functional Foreign Gene in Adult Mammalian Brain following in Vivo Transfer via a Herpes Simplex Virus Type 1 Defective Viral Vector", Molecular and Cellular Neurosciences 2:320-330 (1991).

Kihlberg et al, "Protein H, an Antiphagocytic Surface Protein in *Streptococcus pyogenes*", Infection and Immunity 67(4):1708-1714 (1999).

Klein et al, "Distinctive properties of signal sequences from bacterial lipoproteins", Protein Engineering 2(1):15-20 (1988).

Koeberling et el, "Bactericidal Antibody Responses Elicited by a Meningococcal Outer Membrane Vesicle Vaccine with Overexpressed Factor H-binding Protein and Genetically Attenuated Endotoxin", The Journal of Infectious Diseases 198:262-270 (2008).

Koebnik, "Proposal for a peptidoglycan-associating alpha-helical motif in the C-terminal regions of some bacterial cell-surface proteins", Molecular Microbiology 16(6):1269-1270 (1995).

Kohler et al, "Continuous cultures of fused cells secreting antibody of predefined specificity", Nature 256:495-497 (1975).

Kuipers et al, "Improved site-directed mutagenesis method using PCR", Nucleic Acids Research 19(16):4558 (1991).

Kuo et al, "Efficient Gene Transfer into Primary Murine Lymphocytes Obviating the Need for Drug Selection", Blood 82(3):845-852 (1993).

Kyte et al, "A Simple Method for Displaying the Hydropathic Character of a Protein", J. Mol. Biol. 157:105-132 (1982).

Landt et al, "A general method for rapid site-directed mutagenesis using the polymerase chain reaction", Gene 96:125-128 (1990).

Lasalle et al, "An Adenovirus Vector for Gene Transfer into Neurons and Glia in the Brain", Science 259:988-990 (1993).

Lebkowski et al, "Adeno-Associated Virus: a Vector System for Efficient Introduction and Integration of DNA into a Variety of Mammalian Cell Types", Molecular and Cellular Biology 8(10):3988-3996 (1988).

Levrero et al, "Defective and nondefective adenovirus vectors for expressing foreign genes in vitro and in vivo", Gene 101:195-202 (1991).

Liu et al, "Chimeric mouse-human IgG1 antibody that can mediate lysis of cancer cells", Proc. Natl. Acad. Sci. 84:3439-3443 (1987).

Loessner et al, "Evidence for a Holin-Like Protein Gene Fully Embedded Out of Frame in the Endolysin Gene of *Staphylococcus aureus* Bacteriophage 187", Journal of Bacteriology 181(15):4452-4460 (1999).

Lukashin et al, "GeneMark.hmm: new solutions for gene finding", Nucleic Acids Research 26(4):1107-1115 (1998).

Lukomski et al, "Extracellular Cysteine Protease Produced by *Streptococcus pyogenes* Participates in the Pathogenesis of Invasive Skin Infection and Dissemination in Mice", Infection and Immunity 67(4):1779-1788 (1999).

Lunn et al, "Effects of Prolipoprotein Signal Peptide Mutations on Secretion of Hybrid Prolipo-beta-lactamase in *Escherichia coli*", The Journal of Biological Chemistry 262(17):8318-8324 (1987).

Machy et al, "Gene transfer from targeted liposomes to specific lymphoid cells by electroporation", Proc. Natl. Acad. Sci. 85:8027-8031 (1988).

Madore, "Characterization of immune response as an indicator of Haemophilus influenzae type b vaccine efficacy", The Pediatric Infectious Disease Journal 17(9):Supplement:S207-S210 (1998).

Mann, et al, "Construction of a Retrovirus Packaging Mutant and Its Use to Produce Helper-Free Defective Retrovirus", Cell 33:153-159 (1983).

Markowitz et al, "A Safe Packaging Line for Gene Transfer: Separating Viral Genes on Two Different Plasmids", Journal of Virology 62(4):1120-1124 (1988).

Martin et al, "Highly Conserved Neisseria meningitidis Surface Protein Confers Protection against Experimental Infection", J. Exp. Med. 185(7):1173-1183 (1997).

Masignani et al, "Vaccination against Neisseria meningitidis Using Three Variants of the Lipoprotein GNA1870", J. Exp. Med. 197(6):789-799 (2003).

Matsuka et al, "Fibrinogen Cleavage by the *Streptococcus pyogenes* Extracellular Cysteine Protease and Generation of Antibodies That Inhibit Enzyme Proteolytic Activity", Infection and Immunity 67(9):4326-4333 (1999).

Mazmanian et al, "*Staphylococcus aureus* Sortase, an Enzyme that Anchors Surface Proteins to the Cell Wall", Science 285:760-763 (1999).

McAtee et al, "Characterization of a *Helicobacter pylori* vaccine candidate by proteome techniques", Journal of Chromatography B, Biomedical Sciences and Applications 714:325-333 (1998).

(56) References Cited

OTHER PUBLICATIONS

McAtee et al, "Identification of Potential Diagnostic and Vaccine Candidates of *Helicobacter pylori* by "Proteome" Technologies", Helicobacter 3(3):163-169 (1998).

McAtee et al, "Identification of Potential Diagnostic and Vaccine Candidates of *Helicobacter pylori* by Two-Dimensional Gel Electrophoresis, Sequence Analysis, and Serum Profiling", Clinical and Diagnostic Laboratory Immunology 5(4):537-542 (1998).

McCormick, "Human Gene Therapy: The First Round", BioTechnology 3(8):689-693 (1985).

McGuiness et al, "Class 1 outer membrane protein of Neisseria meningitidis: epitope analysis of the antigenic diversity between strains, implications for subtype definition and molecular epidemiology", Molecular Microbiology 7(4):505-514 (1993).

Mejlhede et al, "Ribosomal -1 Frameshifting during Decoding of Bacillus subtilis cdd Occurs at the Sequence CGA AAG", Journal of Bacteriology 181(9):2930-2937 (1999).

Milagres et al., "Specificity of Bactericidal Antibody Response to Serogroup B Miningococcal Strains in Brazilian Children after Immunization with an Outer Membrane Vaccine", Infection and Immunity 66(10):4755-4761 (1998).

Miller et al, "Improved Retroviral Vectors for Gene Transfer and Expression", BioTechniques 7(9):980-990 (1992).

Minutes of Oral Proceedings in Opposition against Novartis EP 1 645 631 dated Mar. 5, 2012.

Mir et al, "Long-term, high level in vivo gene expression after electric pulse-mediated gene transfer into skeletal muscle", Academie des sciences 321:893-899 (1998).

Molinari et al, "The Fibronectin-Binding Protein of *Streptococcus pyogenes*, Sfbl, is Involved in the Internalization of Group A Streptococci by Epithelial Cells", Infection and Immunity 65(4):1357-1363 (1997).

Morbidity and Mortality Weekly Report (MMWR), Recommendations and Reports, Case Definitions for Infectious Conditions Under Public Health Surveillance, May 2, 1997, vol. 46, No. RR-10.

Moreno et al, "Immunity and Protection of Mice Against Neisseria meningitidis Group B by Vaccination, Using Polysaccharide Complexed with Outer Membrane Proteins: A Comparison with Purified B Polysaccharide", Infection and Immunity 47(2):527-533 (1985).

Morley et al, "Vaccine prevention of meningococcal disease, coming soon?", Vaccine 20:666-687 (2002).

Morrison et al, "Chimeric human antibody molecules: Mouse antigen-binding domains with human constant region domains", Proc. Natl. Acad. Sci. 81:6851-6855 (1984).

Mountzouros et al, "Detection of Complement-Mediated Antibody-Dependent Bactericidal Activity in a Fluorescence-Based Serum Bactericidal Assay for Group B Neisseria meningitidis", Journal of Clinical Microbiology 38(8):2878-2884 (2000).

Moxon, "Applications of molecular microbiology to vaccinology," Lancet 350(9086):1240-1244 (1997).

Munkley et al., "Blocking of Bactericidal Killing of Neisseria meningitidis by Antibodies Directed Against Class 4 Outer Membrane Protein", Microbial Pathogenesis 11:447-452 (1991).

Murphy et al, "Sequence Diversity of the Factor H Binding Protein Vaccine Candidate in Epidemiologically Relevant Strains of Serogroup B Neisseria meningitidis" The Journal of Infectious Diseases 200:379-389 (2009).

Nakai et al, "Expert System for Predicting Protein Localization Sites in Gram-Negative Bacteria", Proteins: Structure, Function, and Genetics 11:95-110 (1991).

Naldini et al, "Lentiviruses as gene transfer agents for delivery to non-dividing cells", Current Opinion in Biotechnology 9:457-463 (1998).

Nassif, "A Furtive Pathogen Revealed", Science 287:1767-1768 (2000).

Navarre et al, "Surface Proteins of Gram-Positive Bacteria and Mechanisms of Their Targeting to the Cell Wall Envelope", Microbiology and Molecular Biology Reviews 63(1):174-229 (1999).

NCBI GenBank No. AAF42204.1, Tettelin, H. et al., "Hypothetical protein [Neisseria meningitidis]", Feb. 25, 2000, accessed Jul. 12, 2012.

NCBI GenBank: ACB38141.1, factor H-binding protein [Neisseria meningitidis] (Jun. 4, 2010).

NCBI GenBank No. EF108319.1, O'Leary, M. M. et al., Neisseria meningitidis strain NM452 FHBP/GNA1870 variant (GNA1870) gene, complete cds, Nov. 8, 2006, accessed Sep. 5, 2012.

NCBI GenBank: FJ184233.1, "Neisseria meningitidis factor H binding protein variant B09_004 (fhbp) gene, partial cds" (Aug. 4, 2009).

Neisseria gonorrhoeae FA 1090 chromosome Entire clone gono strain FA1090, complete sequence. GenBank Accession gono AE004969, 2153894 bp, Sep. 26, 2000.

Nielsen et al, "Identification of prokaryotic and eukaryotic signal peptides and prediction of their cleavage sites", Protein Engineering 10(1):1-6 (1997).

Nizet et al, "Genetic Locus for Streptolysin S Production by Group A *Streptococcus*", Infection and Immunity 68(7):4245-4254 (2000).

Nordstrand et al, "Allele Substitution of the Streptokinase Gene Reduces the Nephritogenic Capacity of Group A Streptococcal Strain NZ131", Infection and Immunity 68(3):1019-1025 (2000).

Notice of Opposition against Novartis EP 1 645 631 submitted Jul. 23, 2008.

Novartis submits Bexsero®, a multi-component meningococcal B vaccine, for regulatory review in Europe, Novartis Media Release (Dec. 23, 2010).

Olmsted et al, "High-Resolution Visualization by Field Emission Scanning Electron Microscopy of Enterococcus faecalis Surface Proteins Encoded by the Pheromone-Inducible Conjugative Plasmid pCF10", Journal of Bacteriology 175(19):6229-6237 (1993).

Opponent's Further Submission in Preparation of Oral Proceedings in Opposition against Novartis EP 1 645 631 submitted Nov. 3, 2011.

Oudega et al, "A lipoprotein signal peptide plus a cysteine residue at the amino-terminal end of the periplasmic proteins beta-lactamase is sufficient for its lipid modification, processing and membrane localization in *Escherichia coli*", FEMS Microbiology Letters 108:353-360 (1993).

Oudega et al, "*Escherichia coli* SecB, SecA, and SecY Proteins Are Required for Expression and Membrane Insertion of the Bacteriocin Release Protein, a Small Lipoprotein", Journal of Bacteriology 175(5):1543-1547 (1993).

Pannekoek et al, "Construction of recombinant neisserial Hsp60 proteins and mapping of antigenic domains", Molecular Microbiology 15(2):277-285 (1995).

Park et al, "DIVCLUS: an automatic method in the Geanfammer package that finds homologous domains in single- and multi-domain proteins", Bioinformatics 14(2):144-150 (1998).

Parkhill, "Campylobacter jejuni genome sequence at the Sanger Centre", (May 8, 1998), available at: http:/www.bio.net/bionet/mm/bionews/1997-May/00442.html.

Parkhill et al, "Complete DNA sequence of a serogroup A strain of Neisseria meningitidis Z2491", Nature 404:502-506 (2000).

Patentees' Further Submission Under Rule 116 EPC in Opposition against Novartis EP 1 645 631 submitted Oct. 14, 2011.

Patentees' Response to Opposition against Novartis EP 1 645 631 submitted May 8, 2009.

Patentees' Submissions Under Rule 116 EPC in Opposition against Novartis EP 1 645 631 submitted Sep. 13, 2011.

PCT Annex to Form PCT/ISA/206 Communication Relating to the Results of the Partial International Search, PCT/US2007/026238.

PCT International Search Report for PCT/US2007/026238 dated Feb. 23, 2009.

Perrett et al, "Towards an improved serogroup B Neisseria meningitidis vaccine", Expert Opin. Biol. Ther. 5(12):1611-1625 (2005).

Pettersson, et al., "The meningococcal lactoferrin receptor", IPNC Abstract (1998).

Pettersson et al., "Vaccine potential of the Neisseria meningitidis Lactoferrin-binding Proteins LbpA and LbpB", Vaccine, 24(17):3545-3557 (2006).

(56) References Cited

OTHER PUBLICATIONS

Phase II clinical results for Novartis vaccine, Novartis Media Release (Oct. 9, 2008).
Phillips, "The challenge of gene therapy and DNA delivery", Journal of Pharmacy and Pharmacology 53:1169-1174 (2001).
Pierschbacher et al, "Influence of Stereochemistry of the Sequence Arg-Gly-Asp-Xaa on Binding Specificity in Cell Adhesion", The Journal of Biological Chemistry 262(36):17294-17298 (1987).
Pizza et al, "Identification of Vaccine Candidates Against Serogroup B Meningococcus by Whole-Genome Sequencing", Science 287:1816-1820 (2000).
Pizza, Preparation of Meningococcal Antigens (2005), available at: http://cordis.europa.eu/search/index.cfm?fuseaction=result.document&RS LANG=EN&RS RCN=7461241&q=.
Podbielski et al, "The Group A Streptococcal virR49 Gene Controls Expression of Four Structural vir Regulon Genes", Infection and Immunity 63(1):9-20 (1995).
Pollitt et al, "Effect of Amino Acid Substitutions at the Signal Peptide Cleavage Site of the *Escherichia coli* Major Outer Membrane Lipoprotein", The Journal of Biological Chemistry 261(4):1835-1837 (1986).
Poolman et al, "Colony variants of Neisseria meningitidis strain 2996 (B-2b:P1.2): influence of class-5 outer membrane proteins and lipopolysaccharides", J Med Microbiol 19(2):203-209 (1985).
Poolman, "Development of a meningococcal vaccine," Infectious Agents and Disease 4(1):13-28 (1995).
Poolman, "Bacterial Outer Membrane Protein Vaccines: The Meningococcal Example", Advances in Experimental Medicine & Biology 397:73-77 (1996).
Preliminary Opinion of the Opposition Division in Opposition against Novartis EP 1 645 631 dated Jun. 24, 2011.
Proft et al, "Identification and Characterization of Novel Superantigens from *Streptococcus pyogenes*", J. Exp. Med. 189(1):89-101 (1999).
Progress through the Sanger Institute FTP Server, submitted in Opposition Proceedings against Novartis EP1645631 on May 8, 2009.
Prosecution history of U.S. Appl. No. 13/455,326, dated Apr. 26, 2013.
PSORT analysis of 200 of the sequences disclosed in PCT/US99/09346, submitted in Opposition Proceedings against Novartis EP1645631 on May 25, 2010.
PSORT analysis of SEQ ID Nos. 4 and 6, and of 'Contig295' 300mer, submitted in Opposition Proceedings against Novartis EP1645631 on May 8, 2009.
PSORT prediction result for SEQ ID No. 2, submitted in Opposition Proceedings against Novartis EP1645631 on May 25, 2010.
Pugsley, "The Complete General Secretory Pathway in Gram-Negative Bacteria", Microbiological Reviews 57(1):50-108 (1993).
Quinn et al, "Immunological Relationship between the Class I Epitope of Streptococcal M Protein and Myosin", Infection and Immunity 66(9):4418-4424 (1998).
Random House Dictionary, Random House, New York, p. 546 (1984).
Reda et al, "Phylogenetic Distribution of Streptococcal Superantigen SSA Allelic Variants Provides Evidence for Horizontal Transfer of ssa within *Streptococcus pyogenes*", Infection and Immunity 64(4):1161-1165 (1996).
Richmond, et al, On Behalf of the 2001 Study Investigators, "Safety, immunogenicity, and tolerability of meningococcal serogroup B bivalent recombinant lipoprotein 2086 vaccine in healthy adolescents: a ranomised, single-blind, placebo-controlled, phase 2 trial", www.thelancet.com/infection, 13 pages, Published online May 7, 2012.
Rinaudo et al, "Vaccinology in the genome era", The Journal of Clinical Investigation, 119(9):2515-2525 (2009).
Romero et al, "Current Status of Meningococcal Group B Vaccine Candidates: Capsular or Noncapsular?" Clinical Microbiology Reviews 7(4):559-575 (1994).

Rosenqvist et al, "Human Antibody Responses to Meningococcal Outer Membrane Antigens after Three Doses of the Norwegian Group B Meningococcal Vaccine", Infection and Immunity 63(12):4642-4652 (1995).
Rosenstein et al, "Meningococcal Vaccines", Infectious Disease Clinics of North America 15(1):155-169 (2001).
Ross, et al., "Identification of Vaccine Candidate Antigens from a Genomic Analysis of Porphyromonas gingivalis", Vaccine 19:4135-4142 (2001).
Sahagan et al, "A Genetically Engineered Murine/Human Chimeric Antibody Retains Specificity for Human Tumor-Associated Antigen", The Journal of Immunology 137(3):1066-1074 (1986).
Salzberg et al, "Microbial gene identification using interpolated Markov models", Nucleic Acids Research 26(2):544-548 (1998).
Sambrook et al, Analysis and Cloning of Eukaryotic Genomic DNA, Molecular Cloning: A Laboratory Manual, Second Edition, Cold Spring Harbor Laboratory Press, Cold Spring Harbor, New York, Chapter 9, pp. 9.1-9.62 (1989).
Sambrook et al, "Synthetic Oligonucleotide Probes", Molecular Cloning: A Laboratory Manual, Second Edition, Cold Spring Harbor Laboratory Press, Cold Spring Harbor, New York, Chapter 11, pp. 11.1-11.61 (1989).
Sambrook et al, Molecular Cloning: A Laboratory Manual, Third Edition, Cold Spring Harbor Laboratory Press, Cold Spring Harbor, New York (2001).
Samulski et al, "A Recombinant Plasmid from Which an Infectious Adeno-Associated Virus Genome Can Be Excised in Vitro and Its Use to Study Viral Replication", Journal of Virology 61(10):3096-3101 (1987).
Samulski et al, "Helper-Free Stocks of Recombinant Adeno-Associated Viruses: Normal Integration Does Not Require Viral Gene Expression", Journal of Virology 63(9):3822-3828 (1989).
Sanger Centre FTP files [online] URL: ftp://ftp.sanger.ac.uk/pub/pathogens/nm/, dated Jul. 23, 2008.
Sanger Centre's "Projects" website as of Dec. 10, 1997 as retrievable via http://web.archive.org, accessed Mar. 15, 2010.
Sankaran et al, "Modification of Bacterial Lipoproteins", Methods in Enzymology 250:683-697 (1995).
Saukkonen et al, "Protective efficacy of monoclonal antibodies to class 1 and class 3 outer membrane proteins of Neisseria meningitidis B:15:P1.16 in infant rat infection model: new prospects for vaccine development", Microbial Pathogenesis 3:261-267 (1987).
Sedegah et al, "Protection against malaria by immunization with plasmid DNA encoding circumsporozoite protein", Proc. Natl. Acad. Sci. 91:9866-9870 (1994).
Sedegah et al, "Improving Protective Immunity Induced by DNA-Based Immunization: Priming with Antigen and GM-CSF-Encoding Plasmid DNA and Boosting witih Antigen-Expressing Recombinant Poxvirus", The Journal of Immunology 164:5905-5912 (2000).
Sepelyak et al, "Adsorption of Pepsin by Aluminum Hydroxide I: Adsorption Mechanism", Journal of Pharmaceutical Sciences 73(11):1514-1517 (1984).
Sequence Analysis Primer, Gribskov and Devereux, eds., M Stockton Press, New York 1991.
Sequence Analysis in Molecular Biology. Treasure Trove or Trivial Pursuit, Gunnar von Heijne, Academic Press (1987).
Sequence for "Putative Lipoprotein [Neisseria Meningitidis Z2491]", NCBI Reference Sequence:YP_002342062.1, dated May 6, 2009, accessed Aug. 4, 2009.
Serruto et al, "Genome-based approaches to develop vaccines against bacterial pathogens", Vaccine 27:3245-3250 (2009).
Smith et al., "Nucleotide sequence determination and genetic analysis of the bacteroides plasmid, pBI143," Plasmid 34(3):211-222 (1995).
Snapper et al, "Bacterial Lipoproteins May Substitute for Cytokines in the Humoral Immune Response to T Cell-Independent Type II Antigens", The Journal of Immunology 155:5582-5589 (1995).
Snapper et al, "IL-3 and Granulocyte-Macrophage Colony-Stimulating Factor Strongly Induce Ig secretion by Sort-Purified Murine

(56) References Cited

OTHER PUBLICATIONS

B Cells Activated Through the Membrane Ig, but Not the CD40, Signaling Pathway", The Journal of Immunology 154:5842-5850 (1995).
Sonnenberg et al, "Definition of *Mycobacterium tuberculosis* Culture Filtrate Proteins by Two-Dimensional Polyacrylamide Gel Electrophoresis, N-Terminal Amino Acid Sequencing, and Electrospray Mass Spectrometry", Infection and Immunity 65(11):4515-4524 (1997).
Sonnhammer et al, "Pfam: A Comprehensive Database of Protein Domain Families Based on Seed Alignments", Proteins: Structure, Function, and Genetics 28:405-420 (1997).
Stedman's Medical Dictionary, Illustrated, 24th Edition, Williams & Wilkins, Baltimore, Maryland, p. 707 (1982).
Stevens, "Streptococcal Toxic-Shock Syndrome: Spectrum of Disease, Pathogenesis, and New Concepts in Treatment", Emerging Infectious Diseases 1(3):69-78 (1995).
Stockbauer et al, "A natural variant of the cysteine protease virulence factor of group A *Streptococcus* with an arginine-glycine-aspartic acid (RGD) motif preferentially binds human integrens alphavbeta3 and alphaIIbbeta3", Proc. Natl. Acad. Sci. 96:242-247 (1999).
Stratford-Perricaudet et al, "Widespread Long-term Gene Transfer to Mouse Skeletal Muscles and Heart", J. Clin. Invest. 90:626-630 (1992).
Strauss, "Using DNA Fragments as Probes", Current Protocols in Molecular Biology, Supp. 24, 6.3.1-6.3.6 (1993).
Sun et al, "Chimeric antibody with human constant regions and mouse variable regions directed against carcinoma-associated antigen 17-1A", Proc. Natl. Acad. Sci. 84:214-218 (1987).
Supplementary Declaration by Dr. Julian Parkhill submitted in Opposition Proceedings against Novartis EP1645631 on May 10, 2010.
Supplementary Submission in Opposition Proceedings against Novartis EP 1 645 631 submitted May 25, 2010.
Sutcliff et al, "Lipoproteins of Gram-Positive Bacteria", Journal of Bacteriology 177(5):1123-1128 (1995).
Sworn Statement from Dr. Rino Rappuoli submitted in Opposition Proceedings against Novartis EP1645631 on Oct. 14, 2011.
Sworn Statement from Dr. Giovanna Campanella submitted in Opposition Proceedings against Novartis EP1409013 on Nov. 10, 2011.
Tappero et al, "Immunogenicity of 2 Serogroup B Outer-Membrane Protein Meningococcal Vaccines", JAMA 281(16):1520-1527 (1999).
Tarkka et al, "Antibody production to a meningococcal outer membrane protein cloned into live *Salmonella typhimurium* aroA vaccine strain", Micrb. Pathogen 6:327-335 (1989).
Telford et al., "Chapter 1: Genomics and Proteomics in Vaccine Design", New Bacterial Vaccines, Kleweur Academic/Plenum Publishers, USA, pp. 1-11 (2003).
Tettelin et al, "Complete Genome Sequence of Neisseria meningitidis Serogroup B Strain MC58", Science 287:1809-1815 (2000).
Ton-That et al, "Purification and characterization of sortase, the transpeptidase that cleaves surface proteins of *Staphylococcus aureus* at the LPXTG motif", Proc Natl Acad Sci 96(22):12424-12429 (1999).
Tondella et al, "Distribution of Neisseria meningitidis Serogroup B Serosubtypes and Serotypes Circulating in the United States", Journal of Clinical Microbiology 38(9):3323-3328 (2000).
Ulmer et al, "Heterologous Protection Against Influenza by Injection of DNA Encoding a Viral Protein", Science 259:1745-1748 (1993).
University of Oklahoma-Neisseria gonorrhoeae webpage to retrieve genome [online] URL: http://dna1.chem.ou.edu/gono.html, Apr. 5, 2004, accessed Aug. 3, 2012.
U.S. Pat. No. 8,398,988 B2 Prosecution History (Feb. 23, 2012-Feb. 27, 2013).

Van Der Ende et al, "Multiple Mechanisms of Phase Variation of PorA in Neisseria meningitidis", Infection and Immunity 68(12):6685-6690 (2000).
Van Der Ley et al., "Construction of Neisseria meningitidis Strains Carrying Multiple Chromosomal the porA gene for Use in the production of a Multivalent Outer Membrane Vesicle Vaccine", Vaccine 13(4):401-407 (1995).
Wahl et al, "Improved Radioimaging and Tumor Localization with Monoclonal F(ab')2", J Nucl Med 24:316-325 (1983).
Webster's II New Riverside University Dictionary, The Riverside Publishing Company, p. 933 (1984).
Weldingh et al, "Two-Dimensional Electrophoresis for Analysis of *Mycobacterium tuberculosis* Culture Filtrate and Purification and Characterization of Six Novel Proteins", Infection and Immunity 66(8):3492-3500 (1998).
Welsch et al, "Protective Activity of Monoclonal Antibodies to Genome-Derived Neisserial Antigen 1870, a Neisseria meningitidis Candidate Vaccine", The Journal of Immunology 172:5606-5615 (2004).
Williams et al, "Introduction of foreign genes into tissues of living mice by DNA-coated microprojectiles", Proc. Natl. Acad. Sci. 88:2726-2730 (1991).
Wilson et al, "Hepatocyte-directed Gene Transfer in Vivo Leads to Transient Improvement of Hypercholesterolemia in Low Density Lipoprotein Receptor-deficient Rabbits", The Journal of Biological Chemistry 267(2):963-967 (1992).
Wolff et al, "Direct Gene Transfer into Mouse Muscle in Vivo", Science 247:1465-1468 (1990).
Woods et al., "Resistance to Meningococcemia Apparently Conferred by Anti-H.8 Monoclonal Antibody is Due to Contaminating Endotoxin and Not to Specific Immunoprotection", Infection and Immunity 55(8):1927-1928 (1987).
Wu et al, "Receptor-mediated in Vitro Gene Transformation by a Soluble DNA Carrier System", The Journal of Biological Chemistry 262(10):4429-4432 (1987).
Wu et al, "Receptor-mediated Gene Delivery and Expression in Vivo", The Journal of Biological Chemistry 263(29):14621-14624 (1988).
Yakushi et al, "Lethality of the Covalent Linkage between Mislocalized Major Outer Membrane Lipoprotein and the Peptidoglycan of *Escherichia coli*", Journal of Bacteriology 179(9):2857-2862 (1997).
Yakushi et al, "A new ABC transporter mediating the detachment of lipid-modified proteins from membranes", Nature Cell Biology 2:212-218 (2000).
York, "Pfizer's Investigational Vaccine, rLP2086, for Invasive Meningococcal Serogroup B Disease", Sabin Vaccine Institute, http://www.sabin.org/sites/sabin.org/files/Laura%20J%20York.pdf, accessed Aug. 1, 2014.
Yutsudo et al, "The Gene Encoding a New Mitogenic Factor in a *Streptococcus pyogenes* Strain is Distributed Only in Group A Streptococci", Infection and Immunity 62(9):4000-4004 (1994).
Zagursky et al, "Bioinformatics: Use in Bacterial Vaccine Delivery", BioTechniques 31(3):636-659 (2001).
Zavascki et al, "First Case Report of Neisseria lactamica Causing Cavitary Lung Disease in an Adult Organ Transplant Recipient", Journal of Clinical Microbiology 44(7):2666-2668 (2006).
Zollinger, "New and Improved Vaccines Against Meningococcal Disease", New Generation Vaccines, 2nd Ed., Myron M. Levine, et al. eds., Marcel Dekker, Inc., New York, NY pp. 469-488 (1997).
Zufferey et al, "Self-Inactivating Lentivirus Vector for Safe and Efficient In Vivo Gene Delivery", Journal of Virology 72(12):9873-9880 (1998).
Beernink, P.T., et al., "The modular architecture of meningococcal factor H-binding protein", Microbiology, 155:2873-2883 (2009).
Callahan, P.M., et al., "The Importance of Surface Charge in the Optimization of Antigen-Adjuvant Interactions", Pharmaceutical Research, 8(7):851-858 (1991).
Marshall, H.S., et al., "A phase 2 open-label safety and immunogenicity study of a meningococcal B bivalent rLP2086 vaccine in healthy adults", Vaccine, 31(12):1569-1575 (2013).

(56) References Cited

OTHER PUBLICATIONS

Van Der Ende, A., et al., "Deletion of porA by Recombination between Clusters of Repetitive Extragenic Palindromic Sequences in Neisseria meningitidis", Infection and Immunity, 67(6):2928-2934 (1999).
Murphy, E., "HM807466: Neisseria meningitidis strain M08452 factor H binding protein variant B153 (fhbp) gene, partial cds.", URL:http://getentry.ddbj.nig.ac.jp/getentry/na/HM807466/?filetype=html, Jul. 21, 2010.
Patel, M., "Outbreaks of Serogroup B Meningococcal Disease on University Campuses—2013", Medical Officer, Meningitis and Vaccine Preventable Diseases Branch, URL:http://www.cdc.gov/vaccines/acip/meetings/downloads/slides-2014-02/04-Mening-Patel.pdf, 16 Pages, Apr. 3, 2014.
Wyeth Neisseria Meningitidis Serogroup B Vaccine, Vaccine and Related Biological Products Advisory Committee Pre-Meeting Background Document, URL:http://www.fda.gov/downloads/AdvisoryCommittees/CommitteesMeeting Materials/BloodVaccinesandOtherBiologics/VaccinesandRelatedBiologicalProductsAdvisoryCommittee/UCM249479.pdf, Mar. 4, 2011.
Anderson, "Elicitation of Functional Antibodies by a Group B Neisseria meningitidis Bivalent rLP2086 Vaccine in Non-Human Primates", NHP IPNC Poster Presentation 2008.
Bambini et al, "Distribution and genetic variability of three vaccine components in a panel of strains representative of the diversity of serogroup B meningococcus", Vaccine 27:2794-2803 (2009).
Beernink et al, "Prevalence of Factor H-Binding Protein Variants and NadA among Meningococcal Group B Isolates from the United States: Implications for the Development of a Multicomponent Group B Vaccine", The Journal of Infectious Diseases 195:1472-1479 (2007).
Bergmann et al, "An endogenously synthesized decamer peptide efficiently primes cytotoxic T cells specific for the HIV-1 envelope glycoprotein", Eur. J. Immunol., 23(11):2777-2781 (1993).
Bergmann et al, "Flanking Residues Alter Antigenicity and Immunogenicity of Multi-Unit CTL Epitopes", The Journal of Immunology, 157:3242-3249 (1996).
Borrow et al, "Meningococcal surrogates of protection—serum bactericidal antibody activity", Vaccine 23:2222-2227 (2005).
Coleman et al, "Virus Attenuation by Genome-Scale Changes in Codon Pair Bias", Science, 320:1784-1787 (2008).
Database Geneseq Online, "N. meningitidis NL096 fHBP protein fragment SEQ ID 76", XP002703350, Database accession No. AXQ90374, Nov. 26, 2009.
Database Geneseq Online, "Neisseria meningitidis modified fHBP fusion protein SEQ:140", XP002703351, Database accession No. AZG10689, Apr. 28, 2011.
Database UniProt Online, "Subname: Full=Factor H binding protein variant A62_001; Subname: Full=Factor H binding protein variant A62_002; Flags: Fragment", XP002703353, Database accession No. C0JF81, May 5, 2009.
Findlow et al, "Multicenter, Open-Label, Randomized Phase II Controlled Trial of an Investigational Recombinant Meningococcal Serogroup B Vaccine With and Without Outer Membrane Vesicles, Administered in Infance", Clinical Infectious Diseases 51(10):1127-1137 (2010).
Frankel et al, "Characterization of diphtheria fusion proteins targeted to the human interleukin-3 receptor", Protein Engineering 13(8):579-591 (2000).
Geysen et al, "A Priori Delineation of a Peptide Which Mimics a Discontinuous Antigenic Determinant", Molecular Immunology, 23(7):709-715 (1986).
Geysen et al, "Use of peptide synthesis to probe viral antigens for epitopes to a resolution of a single amino acid", Proc. Natl. Acad. Sci. USA, 81(13):3998-4002 (1984).
Harris et al, "Preclinical evidence for the potential of a bivalent fHBP vaccine to prevent Neisseria meningitidis serogroup C disease", Human Vaccines 7(Supplement):68-74 (2011).

Liu et al, "High-throughput imaging of bacterial colonies grown on filter plates with application to serum bactericidal assays", Journal of Immunological Methods 292(1-2):187-193 (2004).
Mascioni et al, "Structural Basis for the Immunogenic Properties of the Meningococcal Vaccine Candidate LP2086", Journal of Biological Chemistry 284(13):8738-8746 (2009).
McNeil et al, "Detection of LP2086 on the cell surface of Neisseria meningitidis and its accessibility in the presence of serogroup B capsular polysaccharide", Vaccine 27:3417-3421 (2009).
NCBI GenBank : ACI46791, "Factor H binding protein variant A04_001, partial [Neisseria meningitidis]". Aug. 4, 2009.
NCBI GenBank: ACI46789.1; "Factor H binding protein variant A62_001, partial [Neisseria meningitidis]", Aug. 4, 2009.
NCBI GenBank: AC146791.12; "Medicago truncatula chromosome 8 clone mth2-123m17, complete sequence"; Sep. 17, 2010; accessed Jun. 3, 2014.
NCBI GenBank: AY330365.1; "Neisseria meningitidis strain CDC1492 factor H binding protein variant A22_001 (fhbp) gene, partial cds"; Mar. 12, 2009; accessed Jun. 3, 2014.
NCBI GenBank: AY330400.1; "Neisseria meningitidis strain M982 factor H binding variant B09_001 (fhbp) gene, partial cds"; Mar. 12, 2009; accessed Jun. 3, 2014.
NCBI GenBank: AY330401.1; "Neisseria meningitidis strain 880049 factor H binding protein variant B03_001 (fhbp) gene, partial cds"; Mar. 12, 2009; accessed Jun. 3, 2014.
NCBI GenBank: FJ184103.1; "Neisseria meningitidis factor I-I binding protein variant A12_001 (fhbp) gene, partial cds"; Aug. 4, 2009; accessed Jun. 3, 2014.
NCBI GenBank: FJ184126.1; "Neisseria meningitidis factor H binding protein variant B02_001 (fhbp) gene, partial cds"; Aug. 4, 2009; accessed Jun. 3, 2014.
NCBI GenBank: FJ184157.1; "Neisseria meningitidis factor H binding protein variant B44_001 (fhbp) gene, partial cds"; Aug. 4, 2009; accessed Jun. 3, 2014.
Pajon et al, "Frequency of factor H-binding protein modular groups and susceptibility to cross-reactive bactericidal activity in invasive meningococcal isolates", Vaccine 28:2122-2129 (2010).
Paoletti et al, "Potency of clinical group B streptococcal conjugate vaccines", Vaccine, 19(15-16):2118-2126 (2001).
PCT International Search Report for PCT/IB2011/053934 dated Jan. 20, 2012.
PCT International Search Report for PCT/US02/32369 dated Nov. 14, 2003.
Pillai et al, "Outer membrane protein (OMP) based vaccine for Neisseria meningitidis serogroup B", Vaccine 23:2206-2209 (2005).
Pizza et al, "Factor H-binding protein, a unique meningococcal vaccine antigen", Vaccine 26(Supp8):I46-I48 (2008).
Prome et al, "Characterization of new amino-terminal blocking groups in the normal human adult hemoglobin Hb A1b", Eur. Mass Spectrom. 1(2):195-201 (1995).
Prome et al, "Structure of the Human Adult Hemoglobin Minor Fraction A1b bu Electrospray and Secondary Ion Mass Spectrometry. Pyruvic Acid as Amino-Terminal Blocking Group", The Journal of Biological Chemistry 266 (20):13050-13054 (1991).
Rose et al, "Pyruvic Acid is Attached Through Its Central Carbon Atom to the Amino Terminus of the Recombinant DNA-derived DNA-binding Protein Ner of Bacteriophage Mu", The Journal of Biological Chemistry 267 (27)19101-19106 (1992).
Sankaran, K., et al., "Lipid Modification of Bacterial Prolipoprotein", The Journal of Biological Chemistry, 269 (31)19701-19706 (1994).
Sastalla et al, "Codon-Optimized Fluorescent Proteins Designed for Expression in Low-GC Gram-Positive Bacteria", Applied and Environmental Microbiology, 75(7):2099-2110 (2009).
Seib et al, "Characterization of Diverse Subvariants of the Meningococcal Factor H (fH) Binding Protein for Their Ability to Bind fH, to Mediate Serum Resistance, and to Induce Bactericidal Antibodies", Infection and Immunity 79(2):970-981 (2011).
Snape et al, "Immunogenicity of Two Investigational Serogroup B Meningococcal Vaccines in the First Year of Life", The Pediatric Infectious Disease Journal 29(11):e71-e79 (2010).
Suhrbier, "Multi-epitope DNA vaccines", Immunology and Cell Biology, 75(4):402-408 (1997).

(56) References Cited

OTHER PUBLICATIONS

Welsch et al, "Factor H and Neisserial pathogenesis", Vaccine 26(Supp8):I40-I45 (2008).
Wolf et al, "Conditions Affecting Direct Gene Transfer into Rodent Muscle In Vivo", Biotechniques, 11(4):474-485 1991).
Zhu et al, "Evaluation of Recombinant Lipidated P2086 Protein as a Vaccine Candidate for Group B Neisseria meningitidis in a Murine Nasal Challenge Model", Infection and Immunity 73(10):6838-6845 (2005).
Adacel Prescribing information, http://www.fda.gov/downloads/biologicsbloodvaccines/vaccines/approvedproducts/umc142764.pdf, "Revised: [XX/201X]", accessed Feb. 14, 2015.
Budroni, S. et al., "Neisseria Meningitidis is Structured in Clades Associated with Restriction Modification Systems that Modulate Homologous Recombination", PNAS, Mar. 15, 2011,108 (11): 4494-4499 and supporting information pp. 1-17.
Cheetham, et al., "An HPLC Method for the Determination of Acetyl and Pyruvyl Groups in Polysaccharides, Carbohydrade Polymers", School of Chemistry, The University of New South Wales, Dec. 1985, 5 (6): 399-406.
Database Uniprot [Online] Jul. 4, 2004, "SubName: Full=Factor H binding protein variant A05_001";Flags: Fragment, retrieved from EBI; UNIPROT database accession No. Q6VS29; Database entry from Oct. 28, 2014, entry version 29, sequence version 1See strains Neisseria meningitidis M98-250732 & M98250771.
Database Uniprot [Online] Jul. 5, 2004, "Factor H binding protein variant A22_001"; Flags: Fragment, retrieved from EBI; UNIPROT database accession No. Q6VS35; Database entry from Oct. 28, 2014, entry version 28, sequence version 2 updated on Sep. 23, 2008 See strains Neisseria meningitidis: CDC-1034 and L4-891.
Farley, J., et al. poster entitled "Characterization, Cloning and Expression of Different Subfamlies of the ORF 2086 gene Neisseria Meningitidis", presented at the Thirteenth International Pathogenic Neisseria Conference (the 'IPNC Oslo 2002'), hosted at the Norwegian Institute of Public Health, Oslo, Norway between Sep. 1, 2002 and Sep. 6, 2002, as evidenced by photographs and transcript thereof.
Fredriksen, J.H., et al, "Production, Characterization and Control of MenB-vaccine "Folkehelsa": an Outer Membrane Vesicle Vaccine Against Group B Meningococcal Disease", NIPH Annals, 1991, 14 (2): 67-79.
Gil, J., et al., Proteomic Study via a Non-Gel Based Approach of Meningococcal Outer Membrane Vesicle Vaccine Obtained from Strain CU385 Human Vaccines, 2009, 5 (5): 347-356.
Havrix prescribing information, https://www.gsksource.com/pharma/content/dam/GlaxoSmithKline/US/en/Prescribing_Information/Havrix/pdf/HAVRIX.PDF, revised Jul. 2014, accessed Feb. 18, 2015.
Hedari, et al., Meningococcal Serogroups A, C, W-135, and Y Tetanus Toxoid Conjugate Vaccine: A New Conjugate Vaccine Against Invasive Meningococcal Disease., Infect Drug Resist. Apr. 3, 2014;7:85-99.
Menactra prescribing information, http://www.fda.gov/downloads/BiologicsBloodVaccines/Vaccines/ApprovedProducts/UCM131170.pdf, revised Aug. 26, 2014, accessed Feb. 14, 2015.
Menactra, Australian Public Assessment Report for Groups A, C, Y and W-135 Meningococcal Polysaccharide Diphtheria Toxoid Conjugate Vaccine, https://www.tga.gov.au/file/1277/download , Aug. 31, 2011, accessed Feb. 13, 2015 (part 1 and 2).
Mencevax, New Zealand data sheet, http://www.medsafe.govt.nz/profs/datasheet/m/Mencevaxacwyinj.pdf, date of preparation Mar. 25, 2014, accessed Feb. 14, 2015.
Menveo Package insert, http://www.fda.gov/downloads/BiologicsBloodVaccines/Vaccines/ApprovedProducts/UCM201349.pdf, accessed Feb. 19, 2015, revised Aug. 2013.
Nimenrix product monograph, gsk.com/media/673251/nimenrix.pdf, accessed Feb. 19, 2015, date of revision Jan. 9, 2015.
Nimenrix product monograph, http://webprod5.hc-sc.gc.ca/dpd-bdpp/item-iteme.do?pm-mp=00033642, accessed Mar. 2016. Date of revision Nov. 9, 2015.
Okuda et al, Lipoprotein sortingin bacteria, Annu. Rev. Microbiol., 65:239-259 (2011).
Opposition documents (part 1 of part 11) submitted to the European Patent Office in EP2343308 dated Nov. 13, 2015 to Dec. 23, 2015, https://register.epo.org/application?number=EP10183020&Ing=en&tab=doclist, accessed Mar. 30, 2016.
Opposition documents (part 2) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 3) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 4) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 5) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 6) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 7) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 8) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 9) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 10) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Registration document for VA-MENGOC-BC® Vaccine Together with Translation Into English and Translation Certificate.
Resinger, et al., "Safety, Tolerability, and Immunogenicity of Gardasil Given Concomitantly with Menactra and Adacel" Pediatrics, Jun. 2010; 125 (6):1142-1151.
Rodriguez, A.P., et al., "The Epidemiological Impact of Antimeningococcal B Vaccination in Cuba", Mem Inst Oswaldo Cruz, Jul.-Aug. 1999, 94 (4): 433-440.
Rosenqvist, E., et al., "Effect of Aluminium Hydroxide and Meningococcal Serogroup C Capsular Polysaccharide on the Immunogenicity and Reactogenicity of a Group B Neisseria Meningitides Outer Membrane Vesicle Vaccine", Dev Biol Stand, 1998, 92: 323-333.
Rosenqvist et al, "Human Antibody Responses to Meningococcal Outer Membrane Antigens after Three Doses of the Norwegian Group B Meningococcal Vaccine", Infection and Immunity, 1995, 63(12): 4642-4652.
Sierra, G.V.G., et al.,"Vaccine Against Group B Neisseria Meningitidis: Protection Trial and Mass Vaccination Results in Cuba" NIPH Annals, 1991, 14 (2): 195-210.
Witze et al., Mapping Protein Post-Translational Modifications with Mass Spectrometry, Nat Methods, Oct. 2007; 4 (10): 798-806.
*GlaxoSmithKline UK Ltd* v *Wyeth Holdings LLC* [2016] EWHC 1045 (Ch) (May 12, 2016); Case No. HP-2015-000002; 66 pages; accessed http://www.bailii.org/ew/cases/EWHC/Ch/2016/1045.html on Jul. 11, 2016.

(56) References Cited

OTHER PUBLICATIONS

Koeberling, et al., "Bactericidal Antibody Responses Elicited by a Meningococcal Outer Membrane Vesicle Vaccina with Overexpressed Factor H-Binding Protein and Genetically Attenuated Endotoxin", The Journal of Infectious Diseases, Jul. 2008, 198:262-70.

Moe, et al., "Sequential Immunization with Vesicles Prepared from Heterologous Neisseria meningitidis Strains Elicits Broadly Protective Serum Antibodies to Group B Strains", Infection and Immunity, Nov. 2002, 70:11, 6021-6031.

Opposition papers EP2343308 May 2-9, 2016; 274 pages; accessed https://register.epo.org/application?number=EP10183020&lng=en&tab=doclist on May 16, 2016.

Opposition papers EP2343308 Apr. 6-13, 2016; 30 pages; accessed https://register.epo.org/application?number=EP10183020&lng=en&tab=doclist on May 16, 2016.

Opposition notice EP2343308_(Nov. 13, 2015); 21 pages; accessed https://register.epo.org/application?number=EP10183020&lng=en&tab=doclist on Apr. 21, 2016.

Sierra, et al., "Vaccine Against Group B Neisseria Meningitidis: Protection Trial and Mass Vaccination Results in Cuba", NIPH Annals, Dec. 1991, 14:2, 195-210.

Uli, et al., "Outer Membrane Vesicles of VA-MENGOC-BC Vaccine Against Serogroup B of Neisseria Meningitidis: Analysis of Protein Components by Two-Dimensional Gel Electrophoresis and Mass Spectrometry", Proteomics, 2006, 6, 3389-3399.

\* cited by examiner

SEQUENCE LISTING

<160> NUMBER OF SEQ ID NOS: 23

<210> SEQ ID NO 1
<211> LENGTH: 258
<212> TYPE: PRT
<213> ORGANISM: Artificial Sequence
<220> FEATURE:
<223> OTHER INFORMATION: Synthetic amino acid sequence

<400> SEQUENCE: 1

Cys Gly Ser Ser Gly Gly Gly Gly Val Ala Ala Asp Ile Gly Thr Gly
1               5                   10                  15

Leu Ala Asp Ala Leu Thr Ala Pro Leu Asp His Lys Asp Lys Gly Leu
            20                  25                  30

Lys Ser Leu Thr Leu Glu Asp Ser Ile Ser Gln Asn Gly Thr Leu Thr
        35                  40                  45

Leu Ser Ala Gln Gly Ala Glu Lys Thr Phe Lys Val Gly Asp Lys Asp
    50                  55                  60

Asn Ser Leu Asn Thr Gly Lys Leu Lys Asn Asp Lys Ile Ser Arg Phe
65                  70                  75                  80

Asp Phe Val Gln Lys Ile Glu Val Asp Gly Gln Thr Ile Thr Leu Ala
                85                  90                  95

Ser Gly Glu Phe Gln Ile Tyr Lys Gln Asp His Ser Ala Val Val Ala
                100                 105                 110

Leu Gln Ile Glu Lys Ile Asn Asn Pro Asp Lys Ile Asp Ser Leu Ile

```
            115                 120                 125
Asn Gln Arg Ser Phe Leu Val Ser Gly Leu Gly Gly Glu His Thr Ala
        130                 135                 140

Phe Asn Gln Leu Pro Ser Gly Lys Ala Glu Tyr His Gly Lys Ala Phe
145                 150                 155                 160

Ser Ser Asp Asp Ala Gly Gly Lys Leu Thr Tyr Thr Ile Asp Phe Ala
                165                 170                 175

Ala Lys Gln Gly His Gly Lys Ile Glu His Leu Lys Thr Pro Glu Gln
                180                 185                 190

Asn Val Glu Leu Ala Ser Ala Glu Leu Lys Ala Asp Glu Lys Ser His
                195                 200                 205

Ala Val Ile Leu Gly Asp Thr Arg Tyr Gly Ser Glu Glu Lys Gly Thr
        210                 215                 220

Tyr His Leu Ala Leu Phe Gly Asp Arg Ala Gln Glu Ile Ala Gly Ser
225                 230                 235                 240

Ala Thr Val Lys Ile Arg Glu Lys Val His Glu Ile Gly Ile Ala Gly
                245                 250                 255

Lys Gln
```

<210> SEQ ID NO 2
<211> LENGTH: 261
<212> TYPE: PRT
<213> ORGANISM: Artificial Sequence
<220> FEATURE:
<223> OTHER INFORMATION: Synthetic amino acid sequence

<400> SEQUENCE: 2

```
Cys Gly Ser Ser Gly Gly Gly Ser Gly Gly Gly Val Thr Ala
1               5                   10                  15

Asp Ile Gly Thr Gly Leu Ala Asp Ala Leu Thr Ala Pro Leu Asp His
                20                  25                  30

Lys Asp Lys Gly Leu Lys Ser Leu Thr Leu Glu Asp Ser Ile Ser Gln
        35                  40                  45

Asn Gly Thr Leu Thr Leu Ser Ala Gln Gly Ala Glu Lys Thr Tyr Gly
50                  55                  60

Asn Gly Asp Ser Leu Asn Thr Gly Lys Leu Lys Asn Asp Lys Val Ser
65                  70                  75                  80

Arg Phe Asp Phe Ile Arg Gln Ile Glu Val Asp Gly Gln Leu Ile Thr
                85                  90                  95

Leu Glu Ser Gly Glu Phe Gln Val Tyr Lys Gln Ser His Ser Ala Leu
            100                 105                 110

Thr Ala Leu Gln Thr Glu Gln Glu Gln Asp Pro Glu His Ser Glu Lys
        115                 120                 125

Met Val Ala Lys Arg Arg Phe Arg Ile Gly Asp Ile Ala Gly Glu His
        130                 135                 140

Thr Ser Phe Asp Lys Leu Pro Lys Asp Val Met Ala Thr Tyr Arg Gly
145                 150                 155                 160

Thr Ala Phe Gly Ser Asp Asp Ala Gly Gly Lys Leu Thr Tyr Thr Ile
                165                 170                 175

Asp Phe Ala Ala Lys Gln Gly His Gly Lys Ile Glu His Leu Lys Ser
            180                 185                 190

Pro Glu Leu Asn Val Asp Leu Ala Val Ala Tyr Ile Lys Pro Asp Glu
        195                 200                 205

Lys His His Ala Val Ile Ser Gly Ser Val Leu Tyr Asn Gln Asp Glu
        210                 215                 220
```

```
Lys Gly Ser Tyr Ser Leu Gly Ile Phe Gly Glu Lys Ala Gln Glu Val
225                 230                 235                 240

Ala Gly Ser Ala Glu Val Glu Thr Ala Asn Gly Ile His His Ile Gly
                245                 250                 255

Leu Ala Ala Lys Gln
            260

<210> SEQ ID NO 3
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 3

Cys Gly Ser Ser
1

<210> SEQ ID NO 4
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 4

Cys Gly Ser Ser Gly Gly Gly Gly Val Ala Ala Asp
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Synthetic amino acid sequence

<400> SEQUENCE: 5

Cys Ser Ser Gly Ser Gly Ser Gly Gly Gly Val Ala Ala Asp
1               5                   10                  15

<210> SEQ ID NO 6
<211> LENGTH: 255
<212> TYPE: PRT
<213> ORGANISM: Artificial Sequence
<220> FEATURE:
<223> OTHER INFORMATION: Synthetic amino acid sequence

<400> SEQUENCE: 6

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110
```

```
Gln Val Gln Asp Ser Glu Asp Ser Gly Lys Met Val Ala Lys Arg Gln
        115                 120                 125

Phe Arg Ile Gly Asp Ile Ala Gly Glu His Thr Ser Phe Asp Lys Leu
130                 135                 140

Pro Lys Gly Gly Ser Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
                180                 185                 190

Leu Ala Ala Ala Tyr Ile Lys Pro Asp Glu Lys His His Ala Val Ile
            195                 200                 205

Ser Gly Ser Val Leu Tyr Asn Gln Asp Glu Lys Gly Ser Tyr Ser Leu
        210                 215                 220

Gly Ile Phe Gly Gly Lys Ala Glu Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 7
<211> LENGTH: 259
<212> TYPE: PRT
<213> ORGANISM: Neisseria meningitidis (group B)

<400> SEQUENCE: 7

Cys Ser Ser Gly Gly Gly Gly Gly Val Ala Asp Ile Gly Thr
1               5                   10                  15

Gly Leu Ala Asp Ala Leu Thr Ala Pro Leu Asp His Lys Asp Lys Gly
            20                  25                  30

Leu Lys Ser Leu Thr Leu Glu Asp Ser Ile Pro Gln Asn Gly Thr Leu
        35                  40                  45

Thr Leu Ser Ala Gln Gly Ala Glu Lys Thr Phe Lys Ala Gly Asp Lys
    50                  55                  60

Asp Asn Ser Leu Asn Thr Gly Lys Leu Lys Asn Asp Lys Ile Ser Arg
65                  70                  75                  80

Phe Asp Phe Val Gln Lys Ile Glu Val Asp Gly Gln Thr Ile Thr Leu
                85                  90                  95

Ala Ser Gly Glu Phe Gln Ile Tyr Lys Gln Asp His Ser Ala Val Val
            100                 105                 110

Ala Leu Gln Ile Glu Lys Ile Asn Asn Pro Asp Lys Ile Asp Ser Leu
        115                 120                 125

Ile Asn Gln Arg Ser Phe Leu Val Ser Gly Leu Gly Gly Glu His Thr
    130                 135                 140

Ala Phe Asn Gln Leu Pro Gly Asp Lys Ala Glu Tyr His Gly Lys Ala
145                 150                 155                 160

Phe Ser Ser Asp Asp Ala Gly Gly Lys Leu Thr Tyr Thr Ile Asp Phe
                165                 170                 175

Ala Ala Lys Gln Gly His Gly Lys Ile Glu His Leu Lys Thr Pro Glu
            180                 185                 190

Gln Asn Val Glu Leu Ala Ala Ala Glu Leu Lys Ala Asp Glu Lys Ser
        195                 200                 205

His Ala Val Ile Leu Gly Asp Thr Arg Tyr Gly Ser Glu Glu Lys Gly
    210                 215                 220

Thr Tyr His Leu Ala Leu Phe Gly Asp Arg Ala Gln Glu Ile Ala Gly
```

```
                    225                 230                 235                 240

Ser Ala Thr Val Lys Ile Gly Glu Lys Val His Glu Ile Gly Ile Ala
                245                 250                 255

Gly Lys Gln

<210> SEQ ID NO 8
<211> LENGTH: 261
<212> TYPE: PRT
<213> ORGANISM: Neisseria meningitidis (group B)

<400> SEQUENCE: 8

Cys Ser Ser Gly Ser Gly Ser Gly Gly Gly Val Ala Ala Asp Ile
1               5                   10                  15

Gly Thr Gly Leu Ala Asp Ala Leu Thr Ala Pro Leu Asp His Lys Asp
                20                  25                  30

Lys Gly Leu Lys Ser Leu Thr Leu Glu Asp Ser Ile Ser Gln Asn Gly
            35                  40                  45

Thr Leu Thr Leu Ser Ala Gln Gly Ala Glu Lys Thr Phe Lys Val Gly
        50                  55                  60

Asp Lys Asp Asn Ser Leu Asn Thr Gly Lys Leu Lys Asn Asp Lys Ile
65                  70                  75                  80

Ser Arg Phe Asp Phe Val Gln Lys Ile Glu Val Asp Gly Gln Thr Ile
                85                  90                  95

Thr Leu Ala Ser Gly Glu Phe Gln Ile Tyr Lys Gln Asp His Ser Ala
            100                 105                 110

Val Val Ala Leu Gln Ile Glu Lys Ile Asn Asn Pro Asp Lys Ile Asp
        115                 120                 125

Ser Leu Ile Asn Gln Arg Ser Phe Leu Val Ser Gly Leu Gly Gly Glu
130                 135                 140

His Thr Ala Phe Asn Gln Leu Pro Ser Gly Lys Ala Glu Tyr His Gly
145                 150                 155                 160

Lys Ala Phe Ser Ser Asp Asp Ala Gly Gly Lys Leu Thr Tyr Thr Ile
                165                 170                 175

Asp Phe Ala Ala Lys Gln Gly His Gly Lys Ile Glu His Leu Lys Thr
            180                 185                 190

Pro Glu Gln Asn Val Glu Leu Ala Ser Ala Glu Leu Lys Ala Asp Glu
        195                 200                 205

Lys Ser His Ala Val Ile Leu Gly Asp Thr Arg Tyr Gly Ser Glu Glu
    210                 215                 220

Lys Gly Thr Tyr His Leu Ala Leu Phe Gly Asp Arg Ala Gln Glu Ile
225                 230                 235                 240

Ala Gly Ser Ala Thr Val Lys Ile Arg Glu Lys Val His Glu Ile Gly
                245                 250                 255

Ile Ala Gly Lys Gln
            260

<210> SEQ ID NO 9
<211> LENGTH: 254
<212> TYPE: PRT
<213> ORGANISM: Neisseria meningitidis (group B)

<400> SEQUENCE: 9

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
                20                  25                  30
```

```
Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
 50                  55                  60

Thr Gly Lys Leu Lys Asn Asp Lys Val Ser Arg Phe Asp Phe Ile Arg
 65                  70                  75                  80

Gln Ile Glu Val Asp Gly Gln Thr Ile Thr Leu Ala Ser Gly Glu Phe
                 85                  90                  95

Gln Ile Tyr Lys Gln Asn His Ser Ala Val Val Ala Leu Gln Ile Glu
            100                 105                 110

Lys Ile Asn Asn Pro Asp Lys Ile Asp Ser Leu Ile Asn Gln Arg Ser
            115                 120                 125

Phe Leu Val Ser Gly Leu Gly Gly Glu His Thr Ala Phe Asn Gln Leu
130                 135                 140

Pro Asp Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
            195                 200                 205

Gly Asp Thr Arg Tyr Gly Gly Glu Glu Lys Gly Thr Tyr His Leu Ala
210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 10
<211> LENGTH: 254
<212> TYPE: PRT
<213> ORGANISM: Neisseria meningitidis (group B)

<400> SEQUENCE: 10

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
 50                  55                  60

Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
                 85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
            115                 120                 125

Phe Leu Val Ser Gly Leu Gly Gly Glu His Thr Ala Phe Asn Gln Leu
130                 135                 140

Pro Ser Gly Lys Ala Glu Tyr His Gly Lys Ala Phe Ser Ser Asp Asp
```

```
                145                 150                 155                 160
Ala Gly Gly Lys Leu Thr Tyr Thr Ile Asp Phe Ala Ala Lys Gln Gly
                    165                 170                 175

His Gly Lys Ile Glu His Leu Lys Thr Pro Glu Gln Asn Val Glu Leu
                    180                 185                 190

Ala Ser Ala Glu Leu Lys Ala Asp Glu Lys Ser His Ala Val Ile Leu
                    195                 200                 205

Gly Asp Thr Arg Tyr Gly Gly Glu Lys Gly Thr Tyr His Leu Ala
                210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                    245                 250

<210> SEQ ID NO 11
<211> LENGTH: 263
<212> TYPE: PRT
<213> ORGANISM: Neisseria meningitidis (group B)

<400> SEQUENCE: 11

Cys Ser Ser Gly Gly Gly Ser Gly Gly Gly Val Ala Ala Asp
1               5                   10                  15

Ile Gly Ala Gly Leu Ala Asp Ala Leu Thr Ala Pro Leu Asp His Lys
                20                  25                  30

Asp Lys Gly Leu Lys Ser Leu Thr Leu Glu Asp Ser Ile Ser Gln Asn
            35                  40                  45

Gly Thr Leu Thr Leu Ser Ala Gln Gly Ala Glu Arg Thr Phe Lys Ala
        50                  55                  60

Gly Asp Lys Asp Asn Ser Leu Asn Thr Gly Lys Leu Lys Asn Asp Lys
65                  70                  75                  80

Ile Ser Arg Phe Asp Phe Ile Arg Gln Ile Glu Val Asp Gly Gln Leu
                85                  90                  95

Ile Thr Leu Glu Ser Gly Glu Phe Gln Val Tyr Lys Gln Ser His Ser
                100                 105                 110

Ala Leu Thr Ala Leu Gln Thr Glu Gln Val Gln Asp Ser Glu His Ser
            115                 120                 125

Gly Lys Met Val Ala Lys Arg Gln Phe Arg Ile Gly Asp Ile Val Gly
        130                 135                 140

Glu His Thr Ser Phe Asp Lys Leu Pro Lys Asp Val Met Ala Thr Tyr
145                 150                 155                 160

Arg Gly Thr Ala Phe Gly Ser Asp Asp Ala Gly Gly Lys Leu Thr Tyr
                165                 170                 175

Thr Ile Asp Phe Ala Ala Lys Gln Gly His Gly Lys Ile Glu His Leu
                180                 185                 190

Lys Ser Pro Glu Leu Asn Val Asp Leu Ala Ala Ala Asp Ile Lys Pro
            195                 200                 205

Asp Glu Lys His His Ala Val Ile Ser Gly Ser Val Leu Tyr Asn Gln
        210                 215                 220

Ala Glu Lys Gly Ser Tyr Ser Leu Gly Ile Phe Gly Gly Gln Ala Gln
225                 230                 235                 240

Glu Val Ala Gly Ser Ala Glu Val Glu Thr Ala Asn Gly Ile Arg His
                245                 250                 255

Ile Gly Leu Ala Ala Lys Gln
                260
```

<210> SEQ ID NO 12
<211> LENGTH: 255
<212> TYPE: PRT
<213> ORGANISM: Neisseria meningitidis (group B)

<400> SEQUENCE: 12

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Glu Gln Asp Pro Glu His Ser Gly Lys Met Val Ala Lys Arg Arg
        115                 120                 125

Phe Lys Ile Gly Asp Ile Ala Gly Glu His Thr Ser Phe Asp Lys Leu
    130                 135                 140

Pro Lys Asp Val Met Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190

Leu Ala Thr Ala Tyr Ile Lys Pro Asp Glu Lys His His Ala Val Ile
        195                 200                 205

Ser Gly Ser Val Leu Tyr Asn Gln Asp Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255
```

<210> SEQ ID NO 13
<211> LENGTH: 255
<212> TYPE: PRT
<213> ORGANISM: Neisseria meningitidis (group B)

<400> SEQUENCE: 13

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80
```

```
Gln Ile Glu Val Asp Gly Lys Leu Ile Thr Leu Glu Ser Gly Phe
                85                  90                  95

Gln Val Tyr Lys Gln Ser His Ser Ala Leu Thr Ala Leu Gln Thr Glu
            100                 105                 110

Gln Val Gln Asp Ser Glu Asp Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Lys Gly Gly Ser Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190

Leu Ala Thr Ala Tyr Ile Lys Pro Asp Glu Lys Arg His Ala Val Ile
        195                 200                 205

Ser Gly Ser Val Leu Tyr Asn Gln Asp Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255

<210> SEQ ID NO 14
<211> LENGTH: 255
<212> TYPE: PRT
<213> ORGANISM: Neisseria meningitidis (group B)

<400> SEQUENCE: 14

Cys Ser Ser Gly Gly Gly Val Ala Ala Asp Ile Gly Ala Val Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Ser Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ser Asp Ile Lys Pro Asp Lys Lys Arg His Ala Val Ile
        195                 200                 205
```

Ser Gly Ser Val Leu Tyr Asn Gln Ala Glu Lys Gly Ser Tyr Ser Leu
        210                 215                 220

Gly Ile Phe Gly Gly Gln Ala Gln Glu Val Ala Gly Ser Ala Glu Val
225                 230                 235                 240

Glu Thr Ala Asn Gly Ile Arg His Ile Gly Leu Ala Ala Lys Gln
                245                 250                 255

<210> SEQ ID NO 15
<211> LENGTH: 255
<212> TYPE: PRT
<213> ORGANISM: Neisseria meningitidis (group B)

<400> SEQUENCE: 15

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 16
<211> LENGTH: 263
<212> TYPE: PRT
<213> ORGANISM: Neisseria meningitidis (group B)

<400> SEQUENCE: 16

Cys Ser Ser Gly Gly Gly Gly Ser Gly Gly Gly Gly Val Ala Ala Asp
1               5                   10                  15

Ile Gly Ala Gly Leu Ala Asp Ala Leu Thr Ala Pro Leu Asp His Lys
                20                  25                  30

Asp Lys Gly Leu Lys Ser Leu Thr Leu Glu Asp Ser Ile Ser Gln Asn
            35                  40                  45

Gly Thr Leu Thr Leu Ser Ala Gln Gly Ala Glu Arg Thr Phe Lys Ala
 50                  55                  60

Gly Asp Lys Asp Asn Ser Leu Asn Thr Gly Lys Leu Lys Asn Asp Lys
65                  70                  75                  80

Ile Ser Arg Phe Asp Phe Ile Arg Gln Ile Glu Val Asp Gly Gln Leu
                85                  90                  95

Ile Thr Leu Glu Ser Gly Glu Phe Gln Val Tyr Lys Gln Ser His Ser
            100                 105                 110

Ala Leu Thr Ala Leu Gln Thr Glu Gln Val Gln Asp Ser Glu His Ser
        115                 120                 125

Gly Lys Met Val Ala Lys Arg Gln Phe Arg Ile Gly Asp Ile Val Gly
    130                 135                 140

Glu His Thr Ser Phe Gly Lys Leu Pro Lys Asp Val Met Ala Thr Tyr
145                 150                 155                 160

Arg Gly Thr Ala Phe Gly Ser Asp Asp Ala Gly Gly Lys Leu Thr Tyr
                165                 170                 175

Thr Ile Asp Phe Ala Ala Lys Gln Gly His Gly Lys Ile Glu His Leu
            180                 185                 190

Lys Ser Pro Glu Leu Asn Val Asp Leu Ala Ala Ala Asp Ile Lys Pro
        195                 200                 205

Asp Glu Lys His His Ala Val Ile Ser Gly Ser Val Leu Tyr Asn Gln
    210                 215                 220

Ala Glu Lys Gly Ser Tyr Ser Leu Gly Ile Phe Gly Gly Gln Ala Gln
225                 230                 235                 240

Glu Val Ala Gly Ser Ala Glu Val Glu Thr Ala Asn Gly Ile Arg His
                245                 250                 255

Ile Gly Leu Ala Ala Lys Gln
            260

<210> SEQ ID NO 17
<211> LENGTH: 255
<212> TYPE: PRT
<213> ORGANISM: Neisseria meningitidis (group B)

<400> SEQUENCE: 17

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu

```
                130             135             140
Pro Glu Gly Gly Arg Ala Thr Tyr Arg Gly Thr Ala Phe Gly Ser Asp
145                 150                 155                 160

Asp Ala Ser Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ser Asp Ile Lys Pro Asp Lys Lys Arg His Ala Val Ile
            195                 200                 205

Ser Gly Ser Val Leu Tyr Asn Gln Ala Glu Lys Gly Ser Tyr Ser Leu
            210                 215                 220

Gly Ile Phe Gly Gly Gln Ala Gln Glu Val Ala Gly Ser Ala Glu Val
225                 230                 235                 240

Glu Thr Ala Asn Gly Ile Arg His Ile Gly Leu Ala Ala Lys Gln
                245                 250                 255

<210> SEQ ID NO 18
<211> LENGTH: 254
<212> TYPE: PRT
<213> ORGANISM: Neisseria meningitidis (group B)

<400> SEQUENCE: 18

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
130                 135                 140

Pro Gly Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
            195                 200                 205

Gly Asp Thr Arg Tyr Gly Ser Glu Glu Lys Gly Thr Tyr His Leu Ala
            210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250
```

<210> SEQ ID NO 19

<400> SEQUENCE: 19

000

<210> SEQ ID NO 20
<211> LENGTH: 257
<212> TYPE: PRT
<213> ORGANISM: Neisseria meningitidis (group B)

<400> SEQUENCE: 20

```
Cys Ser Ser Gly Gly Gly Gly Val Ala Ala Asp Ile Gly Ala Gly Leu
 1               5                  10                  15

Ala Asp Ala Leu Thr Ala Pro Leu Asp His Lys Asp Lys Gly Leu Lys
            20                  25                  30

Ser Leu Thr Leu Glu Asp Ser Ile Ser Gln Asn Gly Thr Leu Thr Leu
        35                  40                  45

Ser Ala Gln Gly Ala Glu Lys Thr Phe Lys Val Gly Asp Lys Asp Asn
    50                  55                  60

Ser Leu Asn Thr Gly Lys Leu Lys Asn Asp Lys Ile Ser Arg Phe Asp
65                  70                  75                  80

Phe Val Gln Lys Ile Glu Val Asp Gly Gln Thr Ile Thr Leu Ala Ser
                85                  90                  95

Gly Glu Phe Gln Ile Tyr Lys Gln Asn His Ser Ala Val Val Ala Leu
            100                 105                 110

Gln Ile Glu Lys Ile Asn Asn Pro Asp Lys Ile Asp Ser Leu Ile Asn
        115                 120                 125

Gln Arg Ser Phe Leu Val Ser Gly Leu Gly Gly Glu His Thr Ala Phe
    130                 135                 140

Asn Gln Leu Pro Gly Gly Lys Ala Glu Tyr His Gly Lys Ala Phe Ser
145                 150                 155                 160

Ser Asp Asp Ala Gly Gly Lys Leu Thr Tyr Thr Ile Asp Phe Ala Ala
                165                 170                 175

Lys Gln Gly His Gly Lys Ile Glu His Leu Lys Thr Pro Glu Gln Asn
            180                 185                 190

Val Glu Leu Ala Ala Ala Glu Leu Lys Ala Asp Glu Lys Ser His Ala
        195                 200                 205

Val Ile Leu Gly Asp Thr Arg Tyr Gly Ser Glu Glu Lys Gly Thr Tyr
    210                 215                 220

His Leu Ala Leu Phe Gly Asp Arg Ala Gln Glu Ile Ala Gly Ser Ala
225                 230                 235                 240

Thr Val Lys Ile Gly Glu Lys Val His Glu Ile Ser Ile Ala Gly Lys
                245                 250                 255

Gln
```

<210> SEQ ID NO 21
<211> LENGTH: 254
<212> TYPE: PRT
<213> ORGANISM: Neisseria meningitidis (group B)

<400> SEQUENCE: 21

```
Cys Ser Ser Gly Gly Gly Gly Val Ala Ala Asp Ile Gly Ala Gly Leu
 1               5                  10                  15

Ala Asp Ala Leu Thr Thr Pro Leu Asp His Lys Asp Lys Ser Leu Gln
            20                  25                  30
```

```
Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
 50                  55                  60

Thr Gly Lys Leu Lys Asn Asp Lys Val Ser Arg Phe Asp Phe Ile Arg
 65                  70                  75                  80

Gln Ile Glu Val Asp Gly Gln Thr Ile Thr Leu Ala Ser Gly Glu Phe
                 85                  90                  95

Gln Ile Tyr Lys Gln Asn His Ser Ala Val Val Ala Leu Gln Ile Glu
                100                 105                 110

Lys Ile Asn Asn Pro Asp Lys Ile Asp Ser Leu Ile Asn Gln Arg Ser
            115                 120                 125

Phe Leu Val Ser Gly Leu Gly Gly Glu His Thr Ala Phe Asn Gln Leu
130                 135                 140

Pro Asp Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
                180                 185                 190

Ala Ser Ala Glu Leu Lys Ala Asp Glu Lys Ser His Ala Val Ile Leu
            195                 200                 205

Gly Asp Thr Arg Tyr Gly Gly Glu Glu Lys Gly Thr Tyr His Leu Ala
210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 22
<211> LENGTH: 262
<212> TYPE: PRT
<213> ORGANISM: Neisseria meningitidis (group B)

<400> SEQUENCE: 22

Cys Ser Ser Gly Gly Gly Gly Ser Gly Gly Gly Gly Val Ala Ala Asp
 1                5                  10                  15

Ile Gly Thr Gly Leu Ala Asp Ala Leu Thr Ala Pro Leu Asp His Lys
                 20                  25                  30

Asp Lys Gly Leu Lys Ser Leu Thr Leu Glu Asp Ser Ile Pro Gln Asn
            35                  40                  45

Gly Thr Leu Thr Leu Ser Ala Gln Gly Ala Glu Lys Thr Phe Lys Ala
 50                  55                  60

Gly Asp Lys Asp Asn Ser Leu Asn Thr Gly Lys Leu Lys Asn Asp Lys
 65                  70                  75                  80

Ile Ser Arg Phe Asp Phe Val Gln Lys Ile Glu Val Asp Gly Gln Thr
                 85                  90                  95

Ile Thr Leu Ala Ser Gly Glu Phe Gln Ile Tyr Lys Gln Asn His Ser
                100                 105                 110

Ala Val Val Ala Leu Gln Ile Glu Lys Ile Asn Asn Pro Asp Lys Ile
            115                 120                 125

Asp Ser Leu Ile Asn Gln Arg Ser Phe Leu Val Ser Gly Leu Gly Gly
130                 135                 140

Glu His Thr Ala Phe Asn Gln Leu Pro Gly Asp Lys Ala Glu Tyr His
145                 150                 155                 160
```

```
Gly Lys Ala Phe Ser Ser Asp Pro Asn Gly Arg Leu His Tyr Thr
                165                 170                 175

Ile Asp Phe Thr Asn Lys Gln Gly Tyr Gly Arg Ile Glu His Leu Lys
            180                 185                 190

Thr Pro Glu Leu Asn Val Asp Leu Ala Ser Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
            260
```

<210> SEQ ID NO 23
<211> LENGTH: 255
<212> TYPE: PRT
<213> ORGANISM: Neisseria meningitidis (group B)

<400> SEQUENCE: 23

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Ile Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65              70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
130                 135                 140

Pro Glu Gly Gly Arg Ala Thr Tyr Arg Gly Thr Ala Phe Ser Ser Asp
145                 150                 155                 160

Asp Ala Gly Gly Lys Leu Ile Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ala Asp Ile Lys Pro Asp Glu Lys His His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255
```

NEISSERIA MENINGITIDIS COMPOSITIONS AND METHODS THEREOF

CROSS REFERENCE TO RELATED APPLICATIONS

This application claims the benefit of U.S. provisional patent application Ser. No. 61/875,068, filed Sep. 8, 2013, U.S. provisional patent application Ser. No. 61/926,717, filed Jan. 13, 2014, and U.S. provisional patent application Ser. No. 61/989,432, filed May 6, 2014, which are hereby incorporated herein by reference in their respective entirety.

FIELD OF THE INVENTION

The present invention relates to *Neisseria meningitidis* compositions and methods thereof.

BACKGROUND OF THE INVENTION

*Neisseria meningitidis* is a Gram-negative encapsulated bacterium that can cause sepsis, meningitis, and death. *N. meningitidis* can be classified into at least 12 serogroups (including serogroups A, B, C, 29E, H, I, K, L, W-135, X, Y and Z) based on chemically and antigenically distinctive polysaccharide capsules. Strains with five of the serogroups (A, B, C, Y, and W135) are responsible for the majority of disease.

Meningococcal meningitis is a devastating disease that can kill children and young adults within hours despite the availability of antibiotics. There is a need for improved immunogenic compositions against meningococcal serogroups A, B, C, Y, and W135 and/or X.

Currently, a cross-protective vaccine or composition effective against a wide range of MnB isolates is not yet commercially available. For example, published results-to-date relating to a licensed multi-component composition for protection against serogroup B disease has not demonstrated a direct bactericidal immune response against multiple strains expressing heterologous LP2086 (fHBP) variants, at least in adolescents. At most, published results-to-date relating to the multi-component composition for protection against serogroup B disease appear to show immunogenicity against LP2086 (fHBP) variants that are homologous to the LP2086 (fHBP) variant in the multi-component composition. Accordingly, a cross-protective vaccine or composition effective against diverse MnB isolates is needed as is determining real-world vaccine coverage against a panel of diverse or heterologous meningococcal strains (e.g., representing different geographical regions).

SUMMARY OF THE INVENTION

To meet these and other needs, the present invention relates to *Neisseria meningitidis* compositions and methods thereof.

In one aspect, the invention relates to a composition including about 120 µg/ml of a first lipidated polypeptide including the amino acid sequence set forth in SEQ ID NO: 1, 120 µg/ml of a second lipidated polypeptide including the amino acid sequence set forth in SEQ ID NO: 2, about 2.8 molar ratio polysorbate-80 to the first polypeptide, about 2.8 molar ratio polysorbate-80 to the second polypeptide, about 0.5 mg/ml aluminum, about 10 mM histidine, and about 150 mM sodium chloride. In one embodiment, the first dose is about 0.5 ml in total volume. In one embodiment, the composition induces a bactericidal immune response against *N. meningitidis* serogroup B. In one embodiment, the composition induces a bactericidal immune response against *N. meningitidis* serogroup A, C, 29E, H, I, K, L, W-135, X, Y or Z. In one embodiment, the composition does not further include a polypeptide having less than 100% sequence identity to SEQ ID NO: 1. In one embodiment, the composition does not further include a polypeptide having less than 100% sequence identity to SEQ ID NO: 2. In one embodiment, the first polypeptide has a total of 258 amino acids. In one embodiment, the second polypeptide has a total of 261 amino acids. In one embodiment, the composition induces a bactericidal titer of serum immunoglobulin that is at least 2-fold higher in the human after receiving the first dose than a bactericidal titer of serum immunoglobulin in the human prior to receiving the first dose, wherein the increase in bactericidal titer is measured under identical conditions in a serum bactericidal assay using human complement. In one embodiment, the first lipidated polypeptide consists of the amino acid sequence set forth in SEQ ID NO: 1. In one embodiment, the second lipidated polypeptide consists of the amino acid sequence set forth in SEQ ID NO: 2.

In another aspect, the invention relates to a method of inducing an immune response against *Neisseria meningitidis* in a human. The method includes administering to the human a first dose and a second dose of an effective amount of a composition, said composition including 120 µg/ml of a first lipidated polypeptide including the amino acid sequence set forth in SEQ ID NO: 1, 120 µg/ml of a second lipidated polypeptide including the amino acid sequence set forth in SEQ ID NO: 2, 2.8 molar ratio polysorbate-80 to the first polypeptide, 2.8 molar ratio polysorbate-80 to the second polypeptide, 0.5 mg/ml aluminum, 10 mM histidine, and 150 mM sodium chloride. In one embodiment, a dose of the composition has a total volume of 0.5 ml. In one embodiment, the human is administered at most two doses of the composition. In one embodiment, the human is not further administered a booster dose of the composition. In one embodiment, the human is administered a third dose of the composition. In one embodiment, the human is not further administered a booster dose of the composition after the third dose. In one embodiment, the human is not further administered a fourth dose of the composition. In one embodiment, the third dose is administered to the human within a period of about 6 months after the first dose. In one embodiment, the second dose is administered at least 30 days after the first dose. In one embodiment, the method further includes administering a third dose of the composition, wherein the third dose is administered at least 90 days after the second dose. In one embodiment, the composition induces a bactericidal titer of serum immunoglobulin that is at least 2-fold higher in the human after receiving the first dose than a bactericidal titer of serum immunoglobulin in the human prior to receiving the first dose, when measured under identical conditions in a serum bactericidal assay using human complement. In one embodiment, the immune response is bactericidal against a *N. meningitidis* serogroup B subfamily A strain that is heterologous to a *N. meningitidis* strain expressing A05. In one embodiment, the immune response is bactericidal against a *N. meningitidis* serogroup B subfamily B strain that is heterologous to a *N. meningitidis* strain expressing B01. In one embodiment, the immune response is bactericidal against a *N. meningitidis* serogroup B subfamily A strain that is heterologous to *N. meningitidis* strain M98250771. In one embodiment, the immune response is bactericidal against a *N. meningitidis* serogroup B subfamily B strain that is heterologous to *N. meningitidis* strain CDC1127. In a preferred embodiment, the immune response is bactericidal against a *N. meningitidis* serogroup B subfamily B strain that is heterologous to *N. meningitidis* strain CDC1573. In one embodiment, the first polypeptide has a total of 258 amino acids. In one embodiment, the second polypeptide has a total of 261 amino acids. In one embodiment, the first lipidated polypeptide consists of the amino acid sequence set forth in SEQ ID NO: 1. In one embodiment, the second lipidated polypeptide consists of the amino acid sequence set forth in SEQ ID NO: 2.

In another aspect, the invention relates to a composition that includes 60 μg of a first lipidated polypeptide including the amino acid sequence set forth in SEQ ID NO: 1, 60 μg of a second lipidated polypeptide including the amino acid sequence set forth in SEQ ID NO: 2, 2.8 molar ratio polysorbate-80 to the first polypeptide, 2.8 molar ratio polysorbate-80 to the second polypeptide, 0.5 mg/ml aluminum, 10 mM histidine, and 150 mM sodium chloride, wherein the composition has a total volume of about 0.5 ml. In one embodiment, the composition induces a bactericidal immune response against a *N. meningitidis* serogroup B subfamily A strain that is heterologous to a *N. meningitidis* strain expressing A05. In one embodiment, the composition induces a bactericidal immune response against a *N. meningitidis* serogroup B subfamily B strain that is heterologous to a *N. meningitidis* strain expressing B01. In one embodiment, the composition induces a bactericidal titer of serum immunoglobulin that is at least 2-fold higher in the human after receiving the first dose than a bactericidal titer of serum immunoglobulin in the human prior to receiving the first dose, when measured under identical conditions in a serum bactericidal assay using human complement. In one embodiment, the composition does not further include a polypeptide having less than 100% sequence identity to SEQ ID NO: 1. In one embodiment, the composition does not further include a polypeptide having less than 100% sequence identity to SEQ ID NO: 2. In one embodiment, the first polypeptide has a total of 258 amino acids. In one embodiment, the second polypeptide has a total of 261 amino acids. In one embodiment, the first lipidated polypeptide consists of the amino acid sequence set forth in SEQ ID NO: 1. In one embodiment, the second lipidated polypeptide consists of the amino acid sequence set forth in SEQ ID NO: 2.

SEQUENCE IDENTIFIERS

Figure 1:
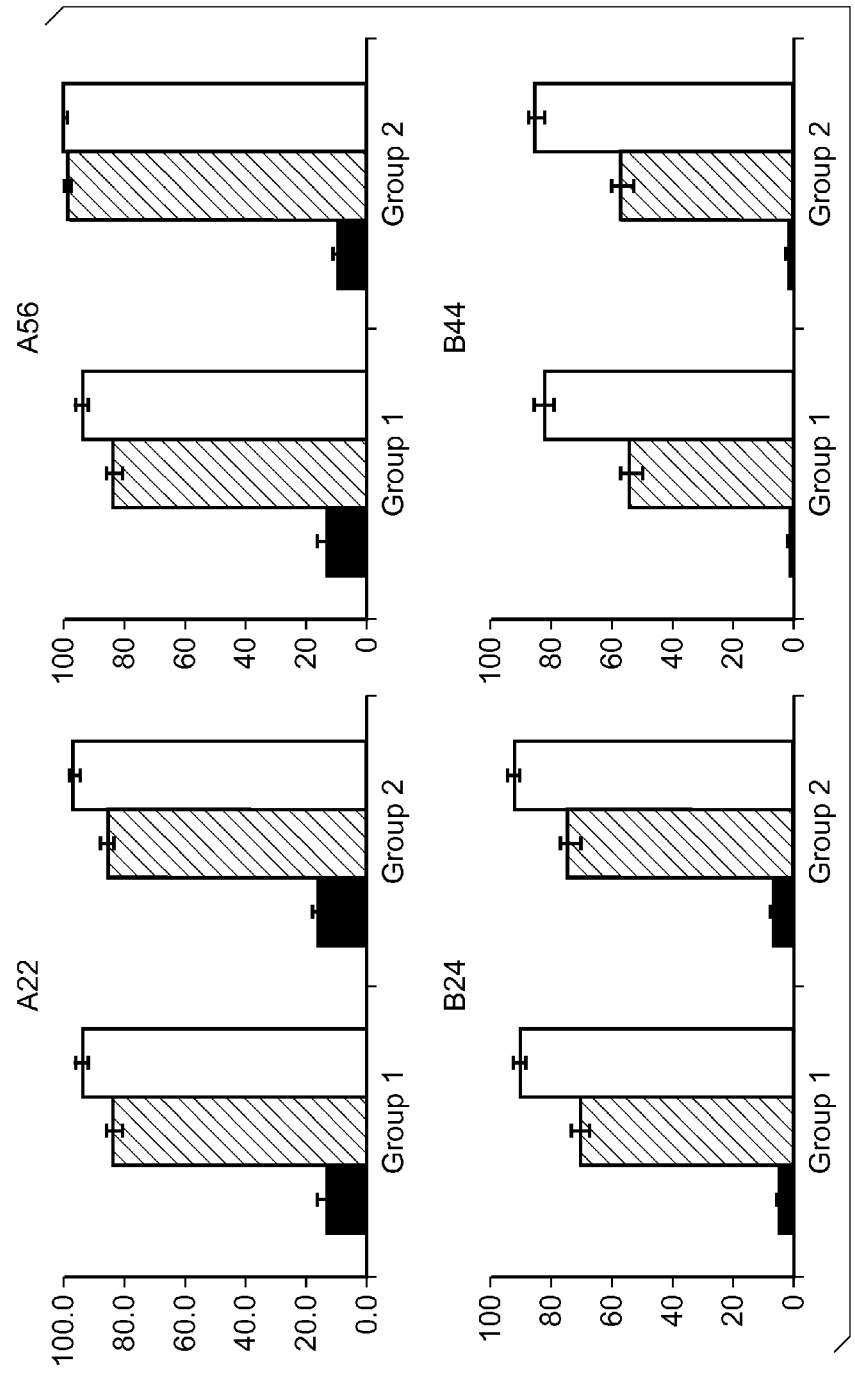
FIG. 1—Proportion of Subjects Achieving hSBA Titers≥LLOQ. hSBA=serum bactericidal assay using human complement; LLOQ=lower limit of quantitation.

SEQ ID NO: 1 sets forth the amino acid sequence for a recombinant *N. meningitidis*, serogroup B, 2086 variant A05 polypeptide antigen.

SEQ ID NO: 2 sets forth the amino acid sequence for a recombinant *N. meningitidis*, serogroup B, 2086 variant B01 polypeptide antigen.

SEQ ID NO: 3 sets forth the amino acid residues at positions 1-4 of SEQ ID NO: 1 and SEQ ID NO: 2.

SEQ ID NO: 4 sets forth the amino acid sequence of the N-terminus of a recombinant Neisserial Subfamily A LP2086 polypeptide (rLP2086) (A05) polypeptide antigen.

SEQ ID NO: 5 sets forth the amino acid sequence of the N-terminus of Neisserial Subfamily A LP2086 M98250771 polypeptide (A05) polypeptide antigen.

SEQ ID NO: 6 sets forth the the amino acid sequence for *N. meningitidis*, serogroup B, 2086 variant B153.

SEQ ID NO: 7 sets forth the amino acid sequence for *N. meningitidis*, serogroup B, 2086 variant A04.

SEQ ID NO: 8 sets forth the amino acid sequence for *N. meningitidis*, serogroup B, 2086 variant A05

SEQ ID NO: 9 sets forth the amino acid sequence for *N. meningitidis*, serogroup B, 2086 variant A12.

SEQ ID NO: 10 sets forth the amino acid sequence for *N. meningitidis*, serogroup B, 2086 variant A22.

SEQ ID NO: 11 sets forth the amino acid sequence for *N. meningitidis*, serogroup B, 2086 variant B02.

SEQ ID NO: 12 sets forth the amino acid sequence for *N. meningitidis*, serogroup B, 2086 variant B03.

SEQ ID NO: 13 sets forth the amino acid sequence for *N. meningitidis*, serogroup B, 2086 variant B09.

SEQ ID NO: 14 sets forth the amino acid sequence for *N. meningitidis*, serogroup B, 2086 variant B22.

SEQ ID NO: 15 sets forth the amino acid sequence for *N. meningitidis*, serogroup B, 2086 variant B24.

SEQ ID NO: 16 sets forth the amino acid sequence for *N. meningitidis*, serogroup B, 2086 variant B44.

SEQ ID NO: 17 sets forth the amino acid sequence for *N. meningitidis*, serogroup B, 2086 variant B16.

SEQ ID NO: 18 sets forth the amino acid sequence for *N. meningitidis*, serogroup B, 2086 variant A07.

SEQ ID NO: 19 sets forth the amino acid sequence for *N. meningitidis*, serogroup B, 2086 variant A19.

SEQ ID NO: 20 sets forth the amino acid sequence for *N. meningitidis*, serogroup B, 2086 variant A06.

SEQ ID NO: 21 sets forth the amino acid sequence for *N. meningitidis*, serogroup B, 2086 variant A15.

SEQ ID NO: 22 sets forth the amino acid sequence for *N. meningitidis*, serogroup B, 2086 variant A29.

SEQ ID NO: 23 sets forth the amino acid sequence for *N. meningitidis*, serogroup B, 2086 variant B15.

DETAILED DESCRIPTION OF THE INVENTION

The inventors surprisingly discovered a composition that includes a first lipidated polypeptide including the amino acid sequence set forth in SEQ ID NO: 1 and a second lipidated polypeptide including the amino acid sequence set forth in SEQ ID NO: 2. The composition has an acceptable safety profile in humans and the composition surprisingly elicits a broadly cross-reactive bactericidal immune response in humans against at least more than two diverse *Neisseria meningitidis* strains.

The inventors further discovered that a 2-dose administration schedule and a 3-dose administration schedule surprisingly yielded hSBA titers of ≥8 against test strains from *N. meningitidis* serogroup B, with vaccine heterologous LP2086 (factor H binding protein (fHBP)) subfamilies A and B in a high proportion of human subjects. A 3-dose administration schedule may provide the broadest protection in humans against diverse MnB clinical strains, when compared to a 2-dose administration schedule.

The inventors also surprisingly discovered that robust immune responses against human papillomavirus and *N. meningitidis* serogroup B were generated after concomitant administration of the rLP2086 composition and a quadrivalent immunogenic composition against human papillomavirus (HPV4). For example, a concomitant administration of the rLP2086 composition and HPV4 composition generated an immune response at least against *N. meningitidis* serogroup B test strains expressing fHBPs that are heterologous to those fHBPs in the rLP2086 composition. Such heterologous test strains include wild-type *N. meningitidis* serogroup B strains that express A22 fHBP, A56 fHBP, B24 fHBP, or B44 fHBP, which are each heterologous to the fHBPs in the rLP2086 composition. See WO/2012/032489, WO/2013/132452, US patent publication number US20120093852, and US patent publication number US20130243807, which describe variant fHBP proteins, including A22 fHBP, A56 fHBP, B24 fHBP, and B44 fHBP, among others. These references are each incorporated by reference in their entirety. The concomitant administration also surprisingly generated an immune response at least against HPV types 6, 11, 16, and/or 18. The immune responses against the HPV types after concomitant administration of the rLP2086 composition and the HPV4 composition were noninferior when compared to the immune response generated by an administration of the HPV4 composition in the absence of the rLP2086 composition.

In addition, the inventors surprisingly discovered that robust immune responses against diphtheria, tetanus, pertussis and poliomyelitis and *N. meningitidis* serogroup B were generated after concomitant administration of the rLP2086 composition and an immunogenic composition against diphtheria, tetanus, pertussis and poliomyelitis. For example, a concomitant administration of the rLP2086 composition and REPEVAX composition generated an immune response at least against *N. meningitidis* serogroup B test strains expressing fHBPs that are heterologous to those fHBPs in the rLP2086 composition. The concomitant administration also surprisingly generated an immune response at least against the 9 antigens in REPEVAX: diphtheria, tetanus, pertussis toxoid, pertussis filamentous hemagglutinin, pertussis pertactin, pertussis fimbrial agglutinogens type 2+3, poliovirus type 1, poliovirus type 2, poliovirus type 3. The immune responses against the REPEVAX antigens after concomitant administration of the rLP2086 composition and the REPEVAX composition were noninferior when compared to the immune response generated by an administration of the REPEVAX composition in the absence of the rLP2086 composition.

Moreover, the inventors surprisingly discovered that the rLP2086 composition induces a bactericidal immune response against an ST409 *N. meningitidis* strain that expresses the fHBP B153 variant. For example, the strain expressing the fHBP B153 variant was found to be susceptible to killing when contacted with human bivalent rLP2086 composition immune sera, in a serum bactericidal assay using human complement (hSBA).

Composition and Vaccine

In one aspect, the invention relates to a composition against *Neisseria meningitidis*. The composition includes a first lipidated polypeptide having the amino acid sequence set forth in SEQ ID NO: 1, and a second lipidated polypeptide having the amino acid sequence set forth in SEQ ID NO: 2.

The inventors surprisingly discovered a single *N. meningitidis* polypeptide component that induces an effective broadly protective immune response against multiple strains of *N. meningitidis* serogroup B. Accordingly, in one embodiment, the composition does not include a fusion protein. In one embodiment, the composition does not include a chimeric protein. In one embodiment, the composition does not include a hybrid protein. In one embodiment, the composition does not further include a peptide fragment. In another embodiment, the composition does not further include a Neisserial polypeptide that is not fHBP. For example, in one embodiment, the composition does not include a PorA protein. In another embodiment, the composition does not include a NadA protein. In another embodiment, the composition does not further include a Neisserial heparin binding antigen (NHBA). In another embodiment, the composition does not further include a Neisserial outer membrane vesicle (OMV). In a preferred embodiment, the composition does not further include antigens, other than the first polypeptide and the second polypeptide.

In another aspect, the inventors surprisingly discovered that polypeptide antigens derived from at most two *N. meningitidis* serogroup B strains induces an effective broadly protective immune response against multiple strains of *N. meningitidis* serogroup B. Accordingly, in one embodiment, the composition does not further include a polypeptide that is not derived from *N. meningitidis* serogroup B subfamily A M98250771 strain and/or *N. meningitidis* serogroup B subfamily B CDC1573 strain.

In one embodiment, the composition does not further include a polypeptide having less than 100% sequence identity to SEQ ID NO: 1. In another embodiment, the composition does not further include a polypeptide having less than 100% sequence identity to SEQ ID NO: 2. For example, the composition does not further include a polypeptide having less than 100% sequence identity to the full length of SEQ ID NO: 1 and/or SEQ ID NO: 2.

In one embodiment, the composition further includes polysorbate-80, aluminum, histidine, and sodium chloride. In one embodiment, the composition includes about 60 µg of a first lipidated polypeptide including the amino acid sequence set forth in SEQ ID NO: 1, about 60 µg of a second lipidated polypeptide including the amino acid sequence set forth in SEQ ID NO: 2, 2.8 molar ratio of polysorbate-80 to each polypeptide, 0.5 mg aluminum/ml as aluminum phosphate, 10 mM histidine, and 150 mM sodium chloride, wherein the composition preferably has a total volume of about 0.5 ml.

In another aspect, the composition includes about 120 µg/ml of a first lipidated polypeptide including the amino acid sequence set forth in SEQ ID NO: 1, about 120 µg/ml of a second lipidated polypeptide including the amino acid sequence set forth in SEQ ID NO: 2, 2.8 molar ratio of polysorbate-80 to each polypeptide, 0.5 mg aluminum/ml as aluminum phosphate, 10 mM histidine, and 150 mM sodium chloride.

In a further aspect, the composition includes a) 60 µg of a first lipidated polypeptide including the amino acid sequence set forth in SEQ ID NO: 1; b) 60 µg of a second lipidated polypeptide including the amino acid sequence set forth in SEQ ID NO: 2; c) 18 µg polysorbate-80; d) 250 µg aluminum; e) 780 µg histidine, and; f) 4380 µg sodium chloride.

In an exemplary embodiment, the composition includes about 60 µg of a first lipidated polypeptide consisting of the amino acid sequence set forth in SEQ ID NO: 1, about 60 µg of a second lipidated polypeptide consisting of the amino acid sequence set forth in SEQ ID NO: 2, 2.8 molar ratio of polysorbate-80 to first lipidated polypeptide and to second lipidated polypeptide, 0.5 mg/ml aluminum phosphate, 10 mM histidine, and 150 mM sodium chloride, wherein the composition has a total volume of about 0.5 ml. In the exemplary embodiment, the composition is a sterile isotonic buffered liquid suspension. In the exemplary embodiment, the composition has a pH 6.0. In the exemplary embodiment, the first polypeptide and the second polypeptide are adsorbed to aluminum.

In one embodiment, the composition has a total volume of about 0.5 ml. In one embodiment, a first dose of the composition has a total volume of about 0.5 ml. A "first dose" refers to the dose of the composition that is administered on Day 0. A "second dose" or "third dose" refers to the dose of the composition that is administered subsequently to the first dose, which may or may not be the same amount as the first dose.

The composition is immunogenic after administration of a first dose to a human. In one embodiment, the first dose is about 0.5 ml in total volume.

The composition induces a bactericidal titer of serum immunoglobulin that is at least greater than 1-fold higher, preferably at least 2-fold higher, in the human after receiving the first dose than a bactericidal titer of serum immunoglobulin in the human prior to receiving the first dose, when measured under identical conditions in a serum bactericidal assay using human complement (hSBA).

The bactericidal titer or bactericidal immune response is against N. meningitidis serogroup B. In a preferred embodiment, the bactericidal titer or bactericidal immune response is against a N. meningitidis serogroup B subfamily A strain and against a N. meningitidis serogroup B subfamily B strain. Most preferably, the bactericidal titer or bactericidal immune response is at least against N. meningitidis serogroup B, subfamily B, B01 strain.

In one embodiment, the composition induces a bactericidal titer of serum immunoglobulin that is at least greater than 1-fold, such as, for example, at least 1.01-fold, 1.1-fold, 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, or 16-fold higher in the human after receiving a dose of the composition than a bactericidal titer of serum immunoglobulin in the human prior to receiving said dose, when measured under identical conditions in a serum bactericidal assay using human complement.

In one embodiment, the composition is an immunogenic composition. In one embodiment, the composition is an immunogenic composition for a human. In another embodiment, the composition is a vaccine. A "vaccine" refers to a composition that includes an antigen, which contains at least one epitope that induces an immune response that is specific for that antigen. The vaccine may be administered directly into the subject by subcutaneous, oral, oronasal, or intranasal routes of administration. Preferably, the vaccine is administered intramuscularly. In one embodiment, the composition is a human vaccine. In one embodiment, the composition is an immunogenic composition against N. meningitidis.

In one embodiment, the composition is a liquid composition. In a preferred embodiment, the composition is a liquid suspension composition. In another preferred embodiment, the composition is not lyophilized.

First Polypeptide

In one embodiment, the composition includes a first polypeptide having the amino acid sequence set forth in SEQ ID NO: 1. In one preferred embodiment, the composition includes about 60 μg of a first polypeptide including the amino acid sequence set forth in SEQ ID NO: 1, wherein the composition preferably has a total volume of 0.5 ml. In another embodiment, the composition includes about 120 μg/ml of a first polypeptide including the amino acid sequence set forth in SEQ ID NO: 1. The polypeptide is a modified factor H binding protein (fHBP) from N. meningitidis strain M98250771. A description of fHBP is disclosed in WO2012032489 and US patent publication US 2012/0093852, which are each incorporated by reference in their entirety. The polypeptide is N-terminally lipidated with three predominant fatty acids C16:0, C16:1, and C18:1 covalently linked at three positions of the polypeptide. The first polypeptide includes a total of 258 amino acids.

The first polypeptide includes two modifications introduced in the N-terminal region of the polypeptide, as compared to the corresponding wild-type sequence from N. meningitidis strain M98250771. A glycine in the second position is added as a consequence of introducing a cloning site. A second modification includes the deletion of four amino acids. Accordingly, in one embodiment, the first polypeptide includes a C-G-S-S sequence (SEQ ID NO: 3) at the N-terminus. See SEQ ID NO: 1, first four amino acid residues.

The N-terminal differences between the first polypeptide sequence and the wild-type Neisserial sequence is shown below. Accordingly, in one embodiment, the first polypeptide includes at least the first 2, 3, 4, 5, 6, 7, 8, 9, 10, 11, 12, 13, or more amino acid residues of the amino acid sequence set forth in SEQ ID NO: 1. Preferably, the first polypeptide includes at least the first 4, more preferably at least the first 6, and most preferably, at least the first 8 amino acid residues of SEQ ID NO: 1.

Comparison of Predicted N-Terminal Sequences of Recombinant and Neisserial Subfamily A LP2086 Polypeptide

```
rLP2086 M98250771
                                        (SEQ ID NO: 4)
CGSS-----GGGGVAAD

Neisserial LP2086 M98250771
                                        (SEQ ID NO: 5)
C-SSGS-GSGGGGVAAD >A05
                                        (SEQ ID NO: 1)
CGSSGGGGVAADIGTGLADALTAPLDHKDKGLKSLTLEDSISQNGTLTLS

AQGAEKTFKVGDKDNSLNTGKLKNDKISRFDFVQKIEVDGQTITLASGEF

QIYKQDHSAVVALQIEKINNPDKIDSLINQRSFLVSGLGGEHTAFNQLPS

GKAEYHGKAFSSDDAGGKLTYTIDFAAKQGHGKIEHLKTPEQNVELASAE

LKADEKSHAVILGDTRYGSEEKGTYHLALFGDRAQEIAGSATVKIREKVH

EIGIAGKQ
```

In one embodiment, the first polypeptide includes the amino acid sequence set forth in SEQ ID NO: 1. In one embodiment, the first polypeptide has a total of 258 amino acids. In one embodiment, the first polypeptide does not include an amino acid sequence having less than 100% sequence identity to SEQ ID NO: 1. In another embodiment, the first polypeptide consists of the amino acid sequence set forth in SEQ ID NO: 1. In another embodiment, the first polypeptide includes the amino acid sequence KDN. See for example, amino acid residues 73-75 of SEQ ID NO: 1. In another embodiment, the first polypeptide includes the amino acid sequence set forth in SEQ ID NO: 3 at the N-terminus of the polypeptide. In another embodiment, the first polypeptide includes the amino acid sequence set forth in SEQ ID NO: 4 at the N-terminus of the polypeptide.

In a preferred embodiment, the first polypeptide is readily expressed in a recombinant host cell using standard techniques known in the art. In another preferred embodiment, the first polypeptide includes a bactericidal epitope on the N- and/or C-domain of SEQ ID NO: 1. In one embodiment, the first polypeptide includes at least the first 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues of the amino acid sequence set forth in SEQ ID NO: 1. Preferably, the first polypeptide includes at least the first 2, more preferably at least the first 4, and most preferably, at least the first 8 amino acid residues of SEQ ID NO: 1.

In another embodiment, the first polypeptide includes at least the last 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues of the amino acid sequence set forth in SEQ ID NO: 1.

Second Polypeptide

In one embodiment, the composition includes a second polypeptide having the amino acid sequence set forth in SEQ ID NO: 2. In one preferred embodiment, the composition includes about 60 μg of a second polypeptide including the amino acid sequence set forth in SEQ ID NO: 2, wherein the composition preferably has a total volume of 0.5 ml. In another embodiment, the composition includes 120 μg/ml of a second polypeptide including the amino acid sequence set forth in SEQ ID NO: 2. The polypeptide is a factor H binding protein (fHBP) from *N. meningitidis* strain CDC1573. A description of fHBP is disclosed in WO2012032489 and US patent publication US 2012/0093852, which are each incorporated by reference in their entirety. The polypeptide is N-terminally lipidated with three predominant fatty acids C16:0, C16:1, and C18:1 covalently linked at three positions of the polypeptide. The second polypeptide includes a total of 261 amino acids. In one embodiment, the second polypeptide includes a C-G-S-S sequence (SEQ ID NO: 3) at the N-terminus. See the first four amino acid residues of SEQ ID NO: 2.

```
>B01
                                         (SEQ ID NO: 2)
CGSSGGGGSGGGGVTADIGTGLADALTAPLDHKDKGLKSLTLEDSISQNG

TLTLSAQGAEKTYGNGDSLNTGKLKNDKVSRFDFIRQIEVDGQLITLESG

EFQVYKQSHSALTALQTEQEQDPEHSEKMVAKRRFRIGDIAGEHTSFDKL

PKDVMATYRGTAFGSDDAGGKLTYTIDFAAKQGHGKIEHLKSPELNVDLA

VAYIKPDEKHHAVISGSVLYNQDEKGSYSLGIFGEKAQEVAGSAEVETAN

GIHHIGLAAKQ
```

In one embodiment, the second polypeptide includes the amino acid sequence set forth in SEQ ID NO: 2. In one embodiment, the second polypeptide has a total of 261 amino acids. In one embodiment, the second polypeptide consists of the amino acid sequence set forth in SEQ ID NO: 2. In another embodiment, the second polypeptide does not further include a polypeptide having less than 100% sequence identity to SEQ ID NO: 2. In a preferred embodiment, the first polypeptide and the second polypeptide includes a C-G-S-S(SEQ ID NO: 3) sequence at the N-terminus of the respective polypeptide.

In a preferred embodiment, the second polypeptide is readily expressed in a recombinant host cell using standard techniques known in the art. In another preferred embodiment, the second polypeptide includes a bactericidal epitope on the N- and/or C-domain of SEQ ID NO: 2. In one embodiment, the second polypeptide includes at least the first 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues of the amino acid sequence set forth in SEQ ID NO: 2. Preferably, the second polypeptide includes at least the first 2, more preferably at least the first 4, and most preferably, at least the first 8 amino acid residues of SEQ ID NO: 2.

In another embodiment, the first polypeptide includes at least the last 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues of the amino acid sequence set forth in SEQ ID NO: 2.

Polysorbate-80

Polysorbate 80 (PS-80) is a non-ionic surfactant. Accelerated stability studies using an in vitro monoclonal antibody based potency assay demonstrated instability of the subfamily B protein at higher molar ratios of PS-80 to MnB rLP2086 protein in the final formulation. Further experiments with varying ratios of PS-80 have demonstrated that the optimal molar ratio of PS-80 to MnB rLP2086 protein is approximately 2.8±1.4 to retain potency.

The concentration of PS-80 in the composition is dependent on a molar ratio of PS-80 to the polypeptide. In one embodiment, the composition includes a 2.8±1.4 molar ratio of PS-80 to the first polypeptide and to the second polypeptide. In one embodiment, the composition includes a 2.8±1.1 molar ratio of PS-80 to the first polypeptide and to the second polypeptide. In one embodiment, the composition includes at least 1.9, 2.0, 2.1, 2.2, 2.3, 2.4, 2.5, 2.6, 2.7, 2.8, 2.9, 3.0, 3.1, 3.2, or 3.3 molar ratio of PS-80 to polypeptide. Preferably, the composition includes a 2.8 molar ratio of PS-80 to polypeptide.

The PS-80 to polypeptide molar ratio is determined by calculation from the measured concentration of PS-80 and the measured total polypeptide concentration, in which both values are expressed in moles. For example, PS-80 to Protein molar ratio is determined by calculation of the measured concentration of PS-80 (e.g., by reverse phase high pressure liquid chromatography (RP-HPLC)) to the measured total protein concentration (e.g., by ion exchange-high pressure liquid chromatography (IEX-HPLC)) in the final drug substance, where both values are expressed in moles.

A RP-HPLC is used to quantitate the concentration of Polysorbate 80 in vaccine formulations. The concentration of detergent is determined by saponification of the fatty acid moiety; Polysorbate 80 is converted to free oleic acid by alkaline hydrolysis at 40° C. The sample is separated by RP-HPLC using a C18 column and quantitated using a UV detector at a wavelength of 200 nm.

The first and the second polypeptides are resolved by anion-exchange HPLC. rLP2086(fHBP) Subfamily A and B proteins elute at distinct retention times and are quantitated using a standard curve generated against the respective rLP2086 protein reference material.

The term "molar ratio" and a description of an immunogenic composition including a fHBP and PS-80 is further disclosed in WO2012025873 and US patent publication US 2013/0171194, which are each incorporated by reference in their entirety.

The term "molar ratio" as used herein refers to the ratio of the number of moles of two different elements in a composition. In some embodiments, the molar ratio is the ratio of moles of detergent to moles of polypeptide. In some embodiments, the molar ratio is the ratio of moles of PS-80 to moles of protein. In one embodiment, based on the protein and Polysorbate 80 concentrations, the Molar Ratio may be calculated using the following equation:

$$\text{Molar Ratio} = \frac{\% PS-80}{\text{mg/ml protein}} \times 216$$

In one embodiment, the composition includes about 0.0015, 0.0017, 0.0019, 0.0021, 0.0023, 0.0025, 0.0027, 0.0029, 0.0031, 0.0033, 0.0035, 0.0037, 0.0039, 0.0041, 0.0043, 0.0045, 0.0047, 0.0049, 0.0051 mg/mL PS-80. Preferably, the composition includes about 0.0035 mg/mL PS-80.

In another embodiment, the composition includes about 10 µg, 11 µg, 12 µg, 13 µg, 14 µg, 15 µg, 16 µg, 17 µg, 18 µg, 19 µg, 20 µg, 21 µg, 22 µg, 23 µg, 24 µg, or 25 µg PS-80. In a preferred embodiment, the composition includes about 18 µg PS-80.

In another embodiment, the composition includes a PS-80 concentration ranging from 0.0005% to 1%. For example, the PS-80 concentration in the composition may be at least 0.0005%, 0.005%, 0.01%, 0.02%, 0.03%, 0.04%, 0.05%, 0.06%, 0.07%, 0.08%, 0.09%, 0.10%, 0.2%, 0.3%, 0.4%, 0.5%, 0.6%, 0.7%, 0.8%, 0.9%, 1%, or 1.1% PS-80. In a preferred embodiment, the composition includes about 0.07% PS-80.

Any minimum value may be combined with any maximum value described herein to define a range.

Aluminum

The composition preferably includes about 0.5 mg/ml aluminum phosphate. In one embodiment, the composition includes about 0.5 mg aluminum/ml as aluminum phosphate. AlPO$_4$ at 0.50 mg/ml is added as a stabilizer to provide enhanced manufacturability and stability. This concentration maintains binding (90% binding or better) of the subfamily A and B proteins to aluminum.

The process for producing an aluminum phosphate is described in US patent publication US 2009/0016946, which is incorporated by reference in its entirety.

In one embodiment, the composition does not further include a multivalent cation, other than aluminum. In one embodiment, the composition does not further include Al(OH)$_3$ or Al(SO$_4$)$_3$.

Excipients

In one embodiment, the composition includes histidine. In one embodiment, the composition includes sodium chloride. The composition preferably includes about 10 mM histidine, and about 150 mM sodium chloride. In one embodiment, the composition includes 10 mM histidine and 150 mM sodium chloride.

In another embodiment, the composition includes about 650 µg, 660 µg, 670 µg, 680 µg, 690 µg, 700 µg, 710 µg, 720 µg, 730 µg, 740 µg, 750 µg, 760 µg, 770 µg, 780 µg, 790 µg, 800 µg, 810 µg, 820 µg, 830 µg, 840 µg, or 850 µg of histidine. Preferably, the composition includes about 780 µg histidine. Any minimum value may be combined with any maximum value described herein to define a range.

In one embodiment, the composition includes a tris, phosphate, or succinate buffer. In a preferred embodiment, the composition does not include tris buffer. In a preferred, the composition does not include phosphate buffer. In one preferred embodiment, the composition does not include succinate buffer. In a preferred embodiment, the composition includes histidine buffer.

In a preferred embodiment, the pH of the composition is between 6.0 and 7.0, most preferably pH 6.0. In one embodiment, the pH of the composition is at most 6.1.

Bactericidal Activity

Immune response induced by administering the composition to a human is determined using a serum bactericidal assay using human complement (hSBA) against four *N. meningitidis* serogroup B (MnB) strains. The 4 MnB strains used in the hSBA were selected from a strain pool. The strain pool represented a collection of systematically collected clinically relevant *N. meningitidis* serogroup B strains from the US and Europe. Two of the 4 strains for the SBA are from *N. meningitidis* serogroup B LP2086 (fHBP) subfamily A, and another two of the 4 strains are from *N. meningitidis* serogroup B LP2086(fHBP) subfamily B.

The high proportion of hSBA response to all test strains, especially strains expressing lipoprotein 2086 variants with sequences heterologous to the first polypeptide suggests that the composition is a broadly protective vaccine and that two doses are sufficient to confer high seroprotection at least against *N. meningitidis* serogroup B subfamily A strains.

The high proportion of hSBA response to all test strains, especially strains expressing lipoprotein 2086 variants with sequences heterologous to both the first polypeptide and the second polypeptide suggests that the composition is a broadly protective vaccine and that at most three doses within about a 6 month period are sufficient to confer high seroprotection against *N. meningitidis* serogroup B strains expressing rLP2086 (FHBP) subfamily A and/or subfamily B.

In one embodiment, the hSBA strain is an LP2086 (fHBP) subfamily A strain. In one embodiment, the hSBA strain is an LP2086 (fHBP) subfamily A strain that expresses a lipoprotein 2086 variant that is heterologous to a *N. meningitidis* strain expressing A05. For example, in one embodiment, the hSBA strain is an LP2086 (fHBP) subfamily A strain that expresses a lipoprotein 2086 variant that is heterologous to strain M98250771. In one embodiment, the hSBA strain is an LP2086 (fHBP) A22 strain. In another embodiment, the hSBA strain is an LP2086 (fHBP) A56 strain. In a further embodiment, the hSBA strains are LP2086 (fHBP) A22 and LP2086 (fHBP) A56 strains. In another embodiment, the hSBA strain is an LP2086 A04 strain. In one embodiment, the hSBA strain is an LP2086 A05 strain. In one embodiment, the hSBA strain is an LP2086 A12 strain. In one embodiment, the hSBA strain is an LP2086 A22 strain. In one embodiment, the hSBA strain is an LP2086 A12 strain. In one embodiment, the hSBA strain is an LP2086 A04 strain. In one embodiment, the hSBA strain is an LP2086 A19 strain. In one embodiment, the hSBA strain is an LP2086 A07 strain. In a further embodiment, the hSBA strains include A22, A12, A19, A05, and A07, or any combination thereof. In one embodiment, the hSBA strains include A06, A15, and A29, or any combination thereof.

In one embodiment, the immune response is bactericidal against a N. meningitidis serogroup B subfamily A strain that is heterologous to a N. meningitidis strain expressing A05. In one embodiment, the immune response is against N. meningitidis serogroup B A22 strain. In one embodiment, the immune response is against N. meningitidis serogroup B A56 strain. In one embodiment, the immune response is against N. meningitidis serogroup B A06 strain. In one embodiment, the immune response is against N. meningitidis serogroup B A15 strain. In one embodiment, the immune response is against N. meningitidis serogroup B A29 strain. In one embodiment, the immune response is against N. meningitidis serogroup B A62 strain. In one embodiment, the immune response is bactericidal against a N. meningitidis serogroup B subfamily A strain that is heterologous to N. meningitidis strain M98250771. In one embodiment, the immune response is bactericidal against a N. meningitidis serogroup B subfamily A strain that expresses a factor H binding protein including an amino acid sequence that has at least 80%, 81%, 82%, 83%, 84%, 85%, 86%, 87%, 88%, 89%, 90%, 91%, 92%, 93%, 94%, 95%, 96%, 97%, 98%, 99%, or 100% identity to the first polypeptide. In another embodiment, the immune response is bactericidal against a N. meningitidis serogroup B subfamily A strain that expresses a factor H binding protein including an amino acid sequence that has at least 80%, 81%, 82%, 83%, 84%, 85%, 86%, 87%, 88%, 89%, 90%, 91%, 92%, 93%, 94%, 95%, 96%, 97%, 98%, 99%, or 100% identity to a factor H binding protein expressed by N. meningitidis strain M98250771. In a preferred embodiment, the immune response is bactericidal against a N. meningitidis serogroup B subfamily A strain that expresses a factor H binding protein including an amino acid sequence that has at least 80%, more preferably at least 84%, identity to a factor H binding protein expressed by N. meningitidis strain M98250771.

In another embodiment, the immune response is bactericidal against a N. meningitidis serogroup B subfamily A strain that expresses a factor H binding protein including an amino acid sequence that has at most 81%, 82%, 83%, 84%, 85%, 86%, 87%, 88%, 89%, 90%, 91%, 92%, 93%, 94%, 95%, 96%, 97%, 98%, 99%, or 100% identity to the first polypeptide. In another embodiment, the immune response is bactericidal against a N. meningitidis serogroup B subfamily A strain that expresses a factor H binding protein including an amino acid sequence that has at most 81%, 82%, 83%, 84%, 85%, 86%, 87%, 88%, 89%, 90%, 91%, 92%, 93%, 94%, 95%, 96%, 97%, 98%, 99%, or 100% identity to a factor H binding protein expressed by N. meningitidis strain M98250771. In a preferred embodiment, the immune response is bactericidal against a N. meningitidis serogroup B subfamily A strain that expresses a factor H binding protein including an amino acid sequence that has at most 85%, more preferably at most 99%, identity to a factor H binding protein expressed by N. meningitidis strain M98250771. Any minimum value may be combined with any maximum value described herein to define a range.

In one embodiment, the hSBA strain is an LP2086 (fHBP) subfamily B strain. In one embodiment, the hSBA strain is an LP2086 (fHBP) subfamily B strain that expresses a lipoprotein 2086 variant that is heterologous to a N. meningitidis strain expressing B01. For example, in one embodiment, the hSBA strain is an LP2086 (fHBP) subfamily B strain that expresses a lipoprotein 2086 variant that is heterologous to strain CDC1127. In a preferred embodiment, the hSBA strain is an LP2086 (fHBP) subfamily B strain that expresses a lipoprotein 2086 variant that is heterologous to strain CDC1573.

In one embodiment, the immune response is bactericidal against a N. meningitidis serogroup B subfamily B strain that is heterologous to a N. meningitidis strain expressing B01. In one embodiment, the immune response is against N. meningitidis serogroup B B24 strain. In one embodiment, the immune response is against N. meningitidis serogroup B B44 strain. In one embodiment, the immune response is against N. meningitidis serogroup B B16 strain. In one embodiment, the immune response is against N. meningitidis serogroup B B03 strain. In one embodiment, the immune response is against N. meningitidis serogroup B B09 strain. In one embodiment, the immune response is against N. meningitidis serogroup B B15 strain. In one embodiment, the immune response is against N. meningitidis serogroup B B153 strain. In one embodiment, the immune response is bactericidal against a N. meningitidis serogroup B subfamily B strain that is heterologous to N. meningitidis strain CDC1573. In one embodiment, the immune response is bactericidal against a N. meningitidis serogroup B subfamily B strain that expresses a factor H binding protein including an amino acid sequence that has at least 80%, 81%, 82%, 83%, 84%, 85%, 86%, 87%, 88%, 89%, 90%, 91%, 92%, 93%, 94%, 95%, 96%, 97%, 98%, 99%, or 100% identity to the second polypeptide. In another embodiment, the immune response is bactericidal against a N. meningitidis serogroup B subfamily B strain that expresses a factor H binding protein including an amino acid sequence that has at least 80%, 81%, 82%, 83%, 84%, 85%, 86%, 87%, 88%, 89%, 90%, 91%, 92%, 93%, 94%, 95%, 96%, 97%, 98%, 99%, or 100% identity to a factor H binding protein expressed by N. meningitidis strain CDC1573. In a preferred embodiment, the immune response is bactericidal against a N. meningitidis serogroup B subfamily B strain that expresses a factor H binding protein including an amino acid sequence that has at least 80% identity, more preferably at least 87% identity, to a factor H binding protein expressed by N. meningitidis strain CDC1573. In another preferred embodiment, the immune response is bactericidal against a N. meningitidis serogroup B subfamily B strain that expresses a factor H binding protein including an amino acid sequence that has 100% identity to a factor H binding protein expressed by N. meningitidis strain CDC1573.

In another embodiment, the immune response is bactericidal against a N. meningitidis serogroup B subfamily B strain that expresses a factor H binding protein including an amino acid sequence that has at most 81%, 82%, 83%, 84%, 85%, 86%, 87%, 88%, 89%, 90%, 91%, 92%, 93%, 94%, 95%, 96%, 97%, 98%, 99%, or 100% identity to the second polypeptide. In another embodiment, the immune response is bactericidal against a N. meningitidis serogroup B subfamily B strain that expresses a factor H binding protein including an amino acid sequence that has at most 81%, 82%, 83%, 84%, 85%, 86%, 87%, 88%, 89%, 90%, 91%, 92%, 93%, 94%, 95%, 96%, 97%, 98%, 99%, or 100% identity to a factor H binding protein expressed by N. meningitidis strain CDC1573. In a preferred embodiment, the immune response is bactericidal against a N. meningitidis serogroup B subfamily B strain that expresses a factor H binding protein including an amino acid sequence that has at most 88% identity, more preferably at least 99% identity, to a factor H binding protein expressed by N. meningitidis strain CDC1573. Any minimum value may be combined with any maximum value described herein to define a range.

In one embodiment, the hSBA strain is an LP2086 (fHBP) B24 strain. In another embodiment, the hSBA strains is an LP2086 (fHBP) B44 strain. In a further embodiment, the hSBA strains includes LP2086 (fHBP) B24 and LP2086 (fHBP) B44 strains. In one embodiment, the hSBA strains includes LP2086 (fHBP) A22, LP2086 (fHBP) A56, LP2086 (fHBP) B24, and LP2086 (fHBP) B44 strains. In one embodiment, the hSBA strain includes B15. In one embodiment, the hSBA strain includes B153. In another embodiment, the hSBA strain is an LP2086 B16 strain. In one embodiment, the hSBA strain is an LP2086 B03 strain. In one embodiment, the hSBA strain is an LP2086 B09 strain. In a further embodiment, the hSBA strains include B24, B16, B44, B03, and B09, or any combination thereof. In another embodiment, the hSBA strains include B24, B16, B44, A22, B03, B09, A12, A19, A05, and A07, or any combination thereof. In another embodiment, the hSBA strains include A06, A07, A12, A15, A19, A29, B03, B09, B15, and B16, or any combination thereof.

In one embodiment, the method induces an immune response against a N. meningitidis serogroup B subfamily A strain and against a N. meningitidis serogroup B subfamily B strain. Preferably, the immune response is bactericidal against a N. meningitidis serogroup B subfamily A strain and against a N. meningitidis serogroup B subfamily B strain.

In one embodiment, the immune response against the N. meningitidis serogroup B subfamily A strain is greater than the immune response against the N. meningitidis serogroup B subfamily B strain. For example, in one embodiment, the immunogenic composition induces higher bactericidal titers against a N. meningitidis serogroup B subfamily A strain than against a N. meningitidis serogroup B subfamily B strain, when tested under identical conditions. In one embodiment, the higher bactericidal titers against a N. meningitidis serogroup B subfamily A strain occurs within 30 days after a second dose of the immunogenic composition against N. meningitidis. In one embodiment, the higher bactericidal titers against a N. meningitidis serogroup B subfamily A strain occur in the absence of a third dose of the immunogenic composition against N. meningitidis.

In another embodiment, the immune response against the N. meningitidis serogroup B subfamily B strain is greater than the immune response against the N. meningitidis serogroup B subfamily A strain. For example, in one embodiment, the immunogenic composition induces higher bactericidal titers against a N. meningitidis serogroup B subfamily B strain than against a N. meningitidis serogroup B subfamily A strain, when tested under identical conditions. In one embodiment, the higher bactericidal titers against a N. meningitidis serogroup B subfamily B strain occurs within 30 days after a second dose of the immunogenic composition against N. meningitidis. In one embodiment, the higher bactericidal titers against a N. meningitidis serogroup B subfamily B strain occur in the absence of a third dose of the immunogenic composition against N. meningitidis.

Titers

In one embodiment, the composition induces an increase in bactericidal titer in the human, as compared to the bactericidal titer in the human prior to administration of a dose of the composition, when measured under identical conditions in an hSBA. In one embodiment, the increase in bactericidal titer is compared to the bactericidal titer in the human before administration of the first dose of the composition, as compared to the bactericidal titer in the human prior to administration of the first dose of the composition, when measured under identical conditions in an hSBA. In one embodiment, the increase in titer is observed after a second dose of the composition, as compared to the bactericidal titer in the human prior to administration of the second dose of the composition, when measured under identical conditions in an hSBA. In another embodiment, the increase in bactericidal titer is observed after a third dose of the composition, as compared to the bactericidal titer in the human prior to administration of the third dose of the composition, when measured under identical conditions in an hSBA.

In one embodiment, the composition induces a bactericidal titer in the human after administration of a dose, wherein the bactericidal titer is at least greater than 1-fold higher than the bactericidal titer in the human prior to administration of the dose, when measured under identical conditions in an hSBA. For example, the bactericidal titer may be at least 1.01-fold, 1.1-fold, 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, or 16-fold higher in the human after receiving a dose of the composition, as compared to the bactericidal titer in the human prior to administration of the dose, when measured under identical conditions in an hSBA.

In one embodiment, a "responder" refers to a human, wherein the composition induces a bactericidal titer in the human after administration of a dose, wherein the bactericidal titer is at least greater than 1-fold higher than the bactericidal titer in the human prior to administration of the dose. In a preferred embodiment, the responder achieves at least a ≥4-fold rise in hSBA titer, as compared to a bactericidal titer in the human prior to administration of the dose. Such a responder may be referred to as having a protective titer.

In one embodiment, the hSBA titer is the reciprocal of the highest dilution of a serum sample that produces a measurable effect. For example, in one embodiment, the hSBA titer is the reciprocal of the highest 2-fold dilution of a test serum that results in at least a 50% reduction of MnB bacteria (50% bacterial survival) compared to the T30 CFU value (i.e., the number of bacteria surviving after incubation in assay wells containing all assay components except test serum; 100% bacterial survival).

In one embodiment, the composition induces a bactericidal titer in the human after receiving the first dose that is at least 2-fold higher than the bactericidal titer in the human prior to receiving the first dose (e.g., higher than the bactericidal titer in the human in the absence of the first dose), when measured under identical conditions in the hSBA. In one embodiment, the composition induces a bactericidal titer in the human that is at least 4-fold higher than the bactericidal titer in the human prior to receiving the first dose, when measured under identical conditions in a human serum bactericidal assay that utilizes human complement (hSBA). In one embodiment, the composition induces a bactericidal titer in the human that is at least 8-fold higher than the bactericidal titer in the human prior to receiving the first dose, when measured under identical conditions in a human serum bactericidal assay that utilizes human complement (hSBA).

In a preferred embodiment, the human serum complement is derived from a human having low intrinsic bactericidal activity for a given SBA test strain. Low intrinsic bactericidal activity refers to, for example, a bactericidal titer that is at least less than a 1:4 dilution against the given SBA test strain. In one embodiment, the human complement is derived from a human having an hSBA titer that is at least less than 1:4, such as a 1:2 dilution, against the given SBA test strain, wherein the composition was not administered to the human.

A human may exhibit an hSBA titer of less than 1:4 prior to administration of a composition, such as the bivalent rLP2086 composition, or a human may exhibit an hSBA titer of ≥1:4 prior to administration of the composition. Accordingly, in preferred embodiments and examples, administration of at least one dose of the composition to the human results in an hSBA titer that is at least greater than 1:4, such as, for example, an hSBA titer of ≥1:8, an hSBA titer of ≥1:16, and an hSBA titer of ≥1:32. The respective Examples described herein include assessments of the proportion of human subjects having an hSBA titer ≥1:8 and/or ≥1:16, wherein the bivalent rLP2086 composition was administered to the human. Such preferred assessments of hSBA titers greater than 1:4 show that the protection, i.e., the bactericidal immune response induced in the human, is associated with the composition.

In one embodiment, the human has an hSBA titer equal to or greater than the hSBA's lower limit of quantitation (LLOQ) after administration of the first dose of the composition. In another embodiment, the human has an hSBA titer equal to or greater than the hSBA's LLOQ after administration of the second dose of the composition. In another embodiment, the human has an hSBA titer equal to or greater than the hSBA's LLOQ after administration of the third dose of the composition.

Additional Immunogenic Compositions

The inventors surprisingly discovered that the immunogenic composition against N. meningitidis may be administered with an immunogenic composition against human papillomavirus (HPV) without negatively affecting the bactericidal response against N. meningitidis. As explained in Example 7 and Example 8, substantial hSBA responses to N. meningitidis test strains were observed among humans who were administered with the immunogenic composition against N. meningitidis and GARDASIL and in humans who were administered with the immunogenic composition against N. meningitidis and saline. Additional increases in hSBA responses were observed about 1 month after a third dose of the immunogenic composition against N. meningitidis.

Moreover, the inventors surprisingly discovered that robust immune responses against both N. meningitidis and HPV were generated in the human following an administration of both the immunogenic composition against N. meningitidis and the immunogenic composition against HPV, as compared to the immune response in the human before administration of the compositions. As explained in Example 7 and Example 8, titers against HPV increased in the human after an administration of the immunogenic composition against N. meningitidis and GARDASIL, as compared to the titers in the human prior to administration of the immunogenic compositions. The increase in titers against HPV was at least greater than 1-fold, at least 2-fold, at least 3-fold, at least 4-fold, or more.

Accordingly, in one embodiment, the method includes inducing an immune response against N. meningitidis in a human, wherein the method further includes administering to the human an immunogenic composition against human papillomavirus. Preferably, the immune response is bactericidal against N. meningitidis. In one embodiment, the method further includes inducing an immune response against HPV. In a preferred embodiment, the method further includes inducing an immune response against any one of human papillomavirus types 6, 11, 16, and 18, or any combination thereof. In one embodiment, the immunogenic composition against HPV is administered to the human within 24 hours of administering said composition against N. meningitidis.

In one embodiment, the method includes inducing an immune response against N. meningitidis in a human, wherein the method further includes administering to the human an immunogenic composition against HPV. Preferably, the immune response is bactericidal against N. meningitidis. In one embodiment, the method further includes inducing an immune response against HPV. In a preferred embodiment, the method further includes inducing an immune response against any one of human papillomavirus types 6, 11, 16, and 18, or any combination thereof. In one embodiment, the immunogenic composition against human papillomavirus is administered to the human within 24 hours of administering said composition against N. meningitidis.

In another aspect, the inventors surprisingly discovered that the immunogenic composition against N. meningitidis may be administered with an immunogenic composition against diphtheria, tetanus, acellular pertussis, and inactivated poliomyelitis virus (dTaP) without negatively affecting the bactericidal response against N. meningitidis. As explained in Example 4, substantial hSBA responses to N. meningitidis test strains were observed among humans who were administered with the immunogenic composition against N. meningitidis and REPEVAX. Additional increases in hSBA responses were observed about 1 month after a third dose of the immunogenic composition against N. meningitidis.

Moreover, the inventors surprisingly discovered that robust immune responses against both N. meningitidis and dTaP were generated in the human following an administration of both the immunogenic composition against N. meningitidis and the immunogenic composition against dTaP, as compared to the immune response in the human before administration of the compositions. As explained in Example 4, titers against dTaP increased in the human after an administration of the immunogenic composition against N. meningitidis and REPEVAX, as compared to the titers in the human prior to administration of the immunogenic compositions. The increase in titers against dTaP was at least greater than 1-fold, at least 2-fold, at least 3-fold, at least 4-fold, or more.

Methods and Administration

In one aspect, the invention relates to a method of inducing an immune response against N. meningitidis in a human. In another aspect, the invention relates to a method of vaccinating a human. In one embodiment, the method includes administering to the human at least one dose of the composition described above. In another embodiment, the method includes administering to the human at least a first dose and a second dose of the composition described above.

Surprisingly, the inventors discovered that a two-dose schedule of the composition induced a bactericidal titer against diverse heterologous subfamily A and against diverse heterologous subfamily B strains in the human. For example, the percentage of humans with an hSBA titer ≥1:8 was 90% or greater for SBA test strains expressing LP2086 (fHBP) A22 or LP2086 (fHBP) A56 following a two-dose schedule of the composition described above. See Example 1.

In one embodiment, the second dose is administered at least 20, 30, 50, 60, 100, 120, 160, 170, or 180 days after the first dose, and at most 250, 210, 200, or 190 days after the first dose. Any minimum value may be combined with any maximum value described herein to define a range.

In another embodiment, the second dose is administered about 30 days after the first dose. In another embodiment, the second dose is administered about 60 days after the first dose, such as, for example, in a 0, 2 month immunization schedule. In another embodiment, the second dose is administered about 180 days after the first dose, such as, for example, in a 0, 6 month immunization schedule. In yet another embodiment, the second dose is administered about 120 days after the first dose, such as, for example, in a 2, 6 month immunization schedule.

In one embodiment, the method includes administering to the human two doses of the composition and at most two doses. In one embodiment, the two doses are administered within a period of about 6 months after the first dose. In one embodiment, the method does not include further administration of a booster to the human. A "booster" as used herein refers to an additional administration of the composition to the human. Administering to the human at most two doses of the composition may be advantageous. Such advantages include, for example, facilitating a human to comply with a complete administration schedule and facilitating cost-effectiveness of the schedule.

In one embodiment, the first dose and the second dose are administered to the human over a period of about 25, 30, 40, 50, 60, 70, 80, 90, 100, 110, 120, 130, 140, 150, 160, 170, 180, 190, or 200 days, and most 400, 390, 380, 370, 365, 350, 340, 330, 320, 310, 300, 290, 280, 270, 260, 250, 240, 230, 220, 210, or 200 days after the first dose. Any minimum value may be combined with any maximum value described herein to define a range.

In one embodiment, the first dose and the second dose are administered to the human over a period of about 30 days. In another embodiment, the first dose and the second dose are administered to the human over a period of about 60 days. In another embodiment, the first dose and the second dose are administered to the human over a period of about 180 days.

Three Doses

The inventors further surprisingly discovered that a three-dose schedule of the composition induced a broader bactericidal titer against strains expressing heterologous LP2086 (fHBP) subfamily B strains in a greater percentage of humans than a two-dose schedule. For example, the percentage of humans with a hSBA titer ≥1:8 was 65% or greater for SBA test strains LP2086 (fHBP) B24 and LP2086 (fHBP) B44 following a two-dose schedule of the composition described above. The percentage of humans with a hSBA titer ≥1:8 was 86% or greater for SBA test strains B24 and B44 following a three-dose schedule of the composition described above. See Example 1.

Accordingly, in one embodiment, a three-dose schedule of the composition induces a bactericidal titer against multiple strains expressing LP2086 (fHBP) heterologous to the first and/or second polypeptide in a greater percentage of humans than a two-dose schedule.

In one embodiment, the method includes administering to the human three doses of the composition. In another embodiment, the method includes administering at most three doses of the composition. In one embodiment, the three doses are administered within a period of about 6 months after the first dose. In one embodiment, the method includes an administration of a booster dose to the human after the third dose. In another embodiment, the method does not include administration of a booster dose to the human after the third dose. In another embodiment, the method does not further include administering a fourth or booster dose of the composition to the human. In a further embodiment, at most three doses within a period of about 6 months are administered to the human.

In an exemplary embodiment, the second dose is administered about 30 days after the first dose, and the third dose is administered about 150 days after the second dose, such as, for example, in a 0, 1, 6 month immunization schedule. In another exemplary embodiment, the second dose is administered about 60 days after the first dose, and the third dose is administered about 120 days after the second dose, such as, for example, in a 0, 2, 6 month immunization schedule.

In one embodiment, the first dose, second dose, and third dose are administered to the human over a period of about 150, 160, 170, or 180 days, and at most 240, 210 200, or 190 days. Any minimum value may be combined with any maximum value described herein to define a range. Preferably, the first dose, second dose, and third dose is administered to the human over a period of about 180 days or 6 months. For example, the second dose may be administered to the human about 60 days after the first dose, and the third dose may be administered to the human about 120 days after the second dose. Accordingly, an exemplary schedule of administration includes administering a dose to the human at about months 0, 2, and 6.

As described above, multiple doses of the immunogenic composition may be administered to the human, and the number of days between each dose may vary. An advantage of the method includes, for example, flexibility for a human to comply with the administration schedules.

EXAMPLES

The following Examples illustrate embodiments of the invention. Unless noted otherwise herein, reference is made in the following Examples to an investigational bivalent recombinant vaccine (rLP2086), which is a preferred exemplary embodiment of a composition including 60 μg of a first lipidated polypeptide including the amino acid sequence set forth in SEQ ID NO: 1 per 0.5 mL dose, 60 μg of a second lipidated polypeptide including the amino acid sequence set forth in SEQ ID NO: 2 per 0.5 mL dose, 2.8 molar ratio polysorbate-80 to the first polypeptide, 2.8 molar ratio polysorbate-80 to the second polypeptide, 0.5 mg $Al^{3+}$/ml of the composition, 10 mM histidine, and 150 mM sodium chloride. More specifically, the investigational bivalent recombinant rLP2086 vaccine includes (a) 60 μg of a first lipidated polypeptide including the amino acid sequence set forth in SEQ ID NO: 1; (b) 60 μg of a second lipidated polypeptide including the amino acid sequence set forth in SEQ ID NO: 2; (c) 18 μg polysorbate-80; (d) 250 μg aluminum; (e) 780 μg histidine, and (f) 4380 μg sodium chloride. Each dose was 0.5 mL.

Example 1

Safety, Tolerability, and Immunogenicity of an Investigational Meningococcal Serogroup B Bivalent (MnB) rLP2086 Vaccine in Healthy Adolescents when Administered in Regimens of 2 or 3 Doses in Healthy Subjects Aged 11 to 18 Years Background:

Safety, tolerability, and immunogenicity of an investigational bivalent, recombinant vaccine (rLP2086) were studied in healthy adolescents 11-18 years of age using 5 dose regimens including 2 or 3 vaccinations (Table 1).

The vaccine is a 0.5 ml-dose formulated to contain 60 μg each of a purified subfamily A and a purified subfamily B rLP2086 protein, 2.8 molar ratio polysorbate-80, and 0.25 mg of $Al^{3+}$ as $AlPO_4$, 10 mM histidine-buffered saline at pH 6.0.

Saline is used as a placebo because there is no known proven safe, immunogenic, and effective vaccine against MnB that could serve as an active control. The normal saline solution includes 0.9% sodium chloride in a 0.5 ml dose.

of rLP2086 recipients experienced redness and swelling, respectively, by group. Injection site pain was the most common local reaction after study dose 1 (7.6-13.1% severe). Fever ≥38° C. after the first study dose of the bivalent rLP2086 vaccine was experienced in 3.3-6.5% by group compared to 2.1% in saline recipients. Local and systemic reactions were generally more frequent after dose 1 than after subsequent doses. 43 of 1712 subjects (2.5%) reported 51 serious AEs; 2 cases were considered related (1 case of vertigo, chills and headache and 1 case of fever and vomiting). No deaths were reported.

TABLE 1

Statistical Analysis on Proportion of Evaluable Study Subjects Achieving hSBA Titer ≥8* for Each Primary Strain 1 Month After Last Dose of Bivalent rLP2086 - Evaluable Immunogenicity Population

| Strain [variant] | Group 1 (0, 1, 6 mo) | | Group 2 (0, 2, 6 mo) | | Group 3 (0, 6 mo) | |
|---|---|---|---|---|---|---|
| | n†/N‡ | %§(95% CI)¶ | n†/N‡ | %§(95% CI)¶ | n†/N‡ | %§ (95% CI)¶ |
| PMB80 [A22] | 330/360 | 91.7¶(88.3, 94.3) | 339/357 | 95.0¶(92.1, 97.0) | 345/369 | 93.5¶(90.5, 95.8) |
| PMB2001 [A56] | 360/362 | 99.4¶(98.0, 99.9) | 355/359 | 98.9¶(97.2, 99.7) | 364/370 | 98.4¶(96.5, 99.4) |
| PMB2948 [B24] | 315/354 | 89.0¶(85.2, 92.0) | 313/354 | 88.4¶(84.6, 91.6) | 291/359 | 81.1¶(76.6, 85.0) |
| PMB2707 [B44] | 315/356 | 88.5¶(84.7, 91.6) | 303/352 | 86.1¶(82.0, 89.5) | 276/356 | 77.5¶(72.2, 82.3) |

| Strain [variant] | Group 4 (0, 2 mo) | | Group 5 (2, 6 mo) | |
|---|---|---|---|---|
| | n†/N‡ | % (95% CI)¶ | n†/N‡ | % (95% CI)¶ |
| PMB80 [A22] | 216/238 | 90.8 (86.3, 94.1) | 102/111 | 91.9 (85.2, 96.2) |
| PMB2001 [A56] | 240/240 | 100.0 (98.5, 100.0) | 112/113 | 99.1 (95.2, 100.0) |
| PMB2948 [B24] | 173/237 | 73.0 (66.9, 78.5) | 76/110 | 69.1 (59.6, 77.6) |
| PMB2707 [B44] | 164/234 | 70.1 (63.8, 75.9) | 81/111 | 73.0 (63.7, 81.0) |

*Lower limit of quantification for all strains = 8.
†Number of subjects with hSBA titer ≥8.
‡Number of subjects with valid hSBA titers.
§P < 0.001 using one-sided exact test based on binomial distribution; Values < 0.0125 are considered significant.
¶Exact 2-sided confidence interval (Clopper and Pearson) based upon the observed proportion of subjects.

Methods:

All subjects in this phase 2, randomized, placebo-controlled, single-blind study attended vaccination visits at months 0, 1, 2 and 6. For blinding, a saline control was given when vaccine was not scheduled. Serum bactericidal assays using human complement (hSBA) were performed with 4 MnB test strains expressing LP2086 (fHBP) fHBP variants A22, A56, B24 and B44 (i.e., the 4 "primary hSBA test strains" in the primary endpoint analysis), all of which are different from the variants in the vaccine. Unsolicited adverse events (AE), solicited local and systemic reactions, and antipyretic use were assessed.

Geometric mean hSBA titers were computed for each primary strain at each blood sampling time point along with 2-sided 95% confidence intervals (CIs). Geometric mean fold rises were computed along with 95% CIs.

A responder was defined as a subject with an hSBA titer equal or above the lower limit of quantitation (LLOQ) of the hSBA assays. The LLOQ for each of the 4 hSBA test strains in the primary endpoint analysis was an hSBA titer equal to 1:8. The limit of detection (LOD) for each primary test strain was a titer equal to 1:4 (widely viewed as the correlate of protection against meningococcal disease).

Results:

1 month after the last vaccine dose, 86-99% subjects (after 3 doses; P<0.001) and 69-100% of subjects (after 2 doses) had hSBA titers ≥8 to each MnB test strain. After study dose 1, 19-27% (1.1-4.3% severe) and 23-27% (0.0-1.0% severe)

Conclusions:

Bivalent rLP2086 had an acceptable safety profile. All 5 dosing regimens yielded hSBA titers against all 4 test strains in a high proportion of subjects. The higher proportions against some test strains after 3 doses compared with 2 doses indicate that 3 doses may provide the broadest protection against diverse MnB clinical strains. Global phase 3 clinical trials are underway with the bivalent rLP2086 vaccine.

One of the objectives of this study was to assess the immune response, as measured by hSBA performed with MnB strains expressing LP2086 subfamily A and B proteins, 1 month after the third vaccination with bivalent rLP2086, among Group 1 subjects (0-, 1-, and 6-month schedule as randomized) and among Group 2 subjects (0-, 2-, and 6-month schedule as randomized). An endpoint for the immunogenicity analysis was the proportion of subjects in Groups 1 and 2 achieving an hSBA titer LLOQ at Month 7 (or 1 month after the third dose of bivalent rLP2086) for each of the 4 primary MnB test strains (A22, A56, B24, and B44). The LLOQ was 1:8 for the 4 primary MnB test strains.

For the evaluable immunogenicity population, the proportion of subjects in Group 1 achieving an hSBA titer ≥1:8 after 3 doses of bivalent rLP2086 was 91.7% for A22, 99.4% for A56, 89% for B24, and 88.5% for B44 (See Table 1 above). Since the lower limit of the 97.5% CI was >50% for all strains (87.8%, p<0.001; 97.8%, p<0.001; 84.7%, p<0.001; and 84.1%, p<0.001 for strains A22, A56, B24, and B44, respectively, the study objective was met for subjects in Group 1.

For Group 2, the proportion of subjects achieving an hSBA titer ≥1:8 after 3 doses of bivalent rLP2086 was 95.0% for A22, 98.9% for A56, 88.4% for B24, and 86.1% for B44 (See Table 1 above). Similar to what was seen for Group 1, the lower limit of the 97.5% CI was >50% for all strains (91.7%, p<0.001; 96.9%, p<0.001; 84.1%, p<0.001; and 81.4%, p<0.001 for strains A22, A56, B24, and B44, respectively, demonstrating that the objective was also met for the subjects in Group 2.

A secondary objective was to assess the immune response, as measured by hSBA performed with MnB strains expressing LP2086 subfamily A and B proteins, 1 month after the second dose of bivalent rLP2086, among group 3 subjects (0- and 6-month schedule as randomized). This secondary objective was the proportion of subjects in Group 3 achieving an hSBA titer≥LLOQ (1:8) at Month 7 (or 1 month after the second dose of bivalent rLP2086) for each of the 4 primary MnB test strains.

This secondary objective was also met since the proportion of subjects in Group 3 achieving an hSBA titer ≥1:8 after 2 doses of bivalent rLP2086 was 93.5%, 98.4%, 81.1%, and 77.5% for the primary MnB test strains with the lower limit of the 97.5% CI >50% for all strains (90.0%, p<0.001; 96.2%, p<0.001; 76.0%, p<0.001; and 72.2%, p<0.001 for strains A22, A56, B24, and B44, respectively. See Table 1 above).

Another secondary objective was the proportion of subjects with hSBA titer ≥ LLOQ for each of the 4 primary MnB test strains at each blood sampling time point for subjects in Groups 1 to 5. The LLOQ for each of the 4 primary hSBA test strains was a titer of 1:8. The proportions of subjects with an hSBA titer ≥1:8 by study time for the evaluable immunogenicity population is shown in Table 1 above.

The proportion of subjects who had an hSBA titer ≥1:8 after 1 dose of bivalent rLP2086 (Group 5 [2- and 6-month schedule] 1 month after Injection 3) was 55.9% for A22, 67.6% for A56, 56.9% for B24, and 23.8% for B44.

The proportion of subjects who had an hSBA titer ≥1:8 one month after 2 doses of bivalent rLP2086 ranged from 74.6% to 100% for subfamily A strains, and from 54.0% to 81.1% for subfamily B strains. After 3 doses, the proportion increased and ranged from 91.7% to 99.4% and from 86.1% to 89.0% for subfamily A and B strains, respectively.

Example 2

Serum Bactericidal Assay Using Human Complement (HSBA)

MnB clearance from the human bloodstream is primarily achieved by complement-mediated bacteriolysis and an intact complement system is important for resistance against infections caused by MnB. The in vivo complement-mediated bacteriolysis of MnB is mimicked in vitro by the serum bactericidal assay using human complement (hSBA), a functional serological assay shown to be the surrogate of protection for meningococcal disease. That is, demonstration of bacterial killing in the serum bactericidal assay using human complement (hSBA) correlates with protection against meningococcal disease. Immunity elicited by the vaccine is determined using hSBAs against 4 MnB strains (fHBP variants A22, A56, B24, and B44).

The four primary MnB test strains were used in the hSBAs described in the Examples for the determination of endpoints. That is, these strains were used to estimate vaccine efficacy using hSBA immunogenicity endpoints. These test strains represent 4 of the 6 fHBP phylogenetic subgroups that account for >90% of disease isolates circulating in the USA and Europe.

TABLE 2

| Variant | Identity to matched fHBP subfamily vaccine component | fHBP subgroup | CC | PorA | Lipooligo-saccharides Sialation Level (mol %) |
|---|---|---|---|---|---|
| A56 | 98.1% | N1C2 | CC213 | P1.22,14 | 55% |
| B44 | 91.6% | N4/N5 | CC269 | P1.19-1,10-4 | 23% |
| A22 | 88.9% | N2C2 | CC41/44 | P1.21,16 | 84% |
| B24 | 86.2% | N6 | CC32 | P1.12-1,13-1 | 22% |

In selecting the 4 primary MnB test strains from invasive disease isolates, an approach was used which took into account the population distribution of the in vitro LP2086 surface expression. Furthermore, the hSBA test strains had to show low baseline hSBA positivity, as the populations at risk for meningococcal disease are characterized by non-existing or low baseline bactericidal activity to most strains. In addition, each of the 4 primary MnB test strains expresses an LP2086 variant that is different from the LP2086 variant in the vaccine, thus allowing an objective assessment of functional immunogenicity and efficacy to invasive meningococcal disease (IMD) strains circulating in the population.

The hSBA measures the amount of anti-meningococcal serogroup B (MnB) antibody in serum capable of initiating complement-mediated bactericidal activity. Briefly, test serum is serially-diluted in 2-fold steps and added to 96-well assay plates. MnB SBA test strains and human serum complement are added, initiating the bactericidal reaction. After incubation of the assay plates at 37° C. for 30-60 minutes (depending on SBA test strain; called T30), the reaction mixture containing bacteria surviving this incubation are diluted and transferred to microfilter plates. Following overnight incubation, surviving bacteria expressed as colony-forming units (CFU) are enumerated using an Immunospot Analyzer. The raw CFU data are recorded electronically and transferred to a data analysis application that calculates the hSBA titer. The hSBA titer is the reciprocal of the highest 2-fold dilution of a test serum that results in at least a 50% reduction of MnB bacteria (50% bacterial survival) compared to the T30 CFU value (i.e., the number of bacteria surviving after incubation in assay wells containing all assay components except test serum; 100% bacterial survival). Titers may be reported as step titers, i.e., 1:4, 1:8, 1:16, etc. Serum samples are tested by two individual, replicate determinations in the same assay. The final titer reported for samples in which the replicate measurements are not identical is the lower of the two replicate measurements when system suitability and sample suitability criteria (e.g. replicate titers must agree within one 2-fold dilution) are met.

hSBA assays were done after serially diluting test sera in Dulbecco's phosphate-buffered saline. Bacteria (roughly 2000 colony-forming units) and human serum complement (20% by weight final concentration) were added to the serially diluted sera in 96-well plates and incubated at 37° C. for 30-40 min (depending on hSBA test strain) in a small-radius orbital shaker at 700 rpm. After incubation, a portion of the reaction mixture was transferred to microfilter plates. After overnight incubation, surviving bacteria were counted with an Immunospot Analyzer (Cellular Technology Limited; Shaker Heights, Ohio, USA) and hSBA titers were analysed with SAS (version 9.2). The hSBA titer was calculated as the reciprocal of the interpolated test serum dilution that resulted in a 50% reduction of bacteria compared with a control not subjected to test serum (i.e., surviving bacteria at the end of the hSBA reaction). Per protocol hSBAs were done on the basis of the hSBA titer that was at or above the lower limit of quantitation of the hSBA assays as established during qualification of the assays with strains listed in the Table 1 of Example 1.

Human serum is the complement source for the SBA. However, the hSBA titers may vary depending on the human complement lot used. Accordingly, human complement is preferably controlled through rigorous screening and qualification to ensure consistent performance in the hSBA. For the hSBA, human serum complement may be pooled from multiple normal healthy human adults or used from individual donors (i.e., not pooled).

Example 3

Polysorbate-80

Three parameters have been optimized for drug product formulation: pH, aluminum concentration and polysorbate 80 (PS-80) to protein molar ratio. In a dose of the composition having a total volume of 0.5 ml, optimal protein binding to aluminum is achieved at a pH of about 6.0 and about a 0.5 mg/ml concentration of aluminum as aluminum phosphate ($AlPO_4$) (which is equivalent to 0.25 mg aluminum per dose). The PS-80 to protein molar ratio is maintained at 2.8±1.4 in order to stabilize the formulation with respect to in vitro potency. Polysorbate 80 (PS-80) is added to drug substance to obtain the target PS-80 to protein molar ratio of 2.8. Therefore, PS-80 is preferably not added during the drug product formulation.

Example 4

Randomized, Placebo-Controlled, Phase 2 Study of the Immunogenicity and Safety of REPEVAX® Administered Concomitantly with Bivalent rLP2086 Vaccine in Healthy Adolescents Background/Aims:

The investigational bivalent rLP2086 vaccine, being developed to prevent *Neisseria meningitidis* serogroup B (MnB) disease in adolescents, was evaluated with concomitant administration of REPEVAX®, a dTaP-inactivated polio vaccine (which may be described in U.S. Pat. No. 7,479,283, WO1990/013313, and EP1666057 B1, and UK Marketing Authorization PL06745/0121) currently used in this population.

Methods:

Adolescents, randomized 1:1 to REPEVAX+rLP2086 or REPEVAX+saline were vaccinated at 0, 2, and 6 months. The proportion of subjects achieving prespecified antibody levels to 9 REPEVAX antigens 30 days after initial vaccination were determined. Immune responses (hSBA) to 4 MnB test strains were measured 30 days after vaccinations 2 and 3. Adverse events (AE) and local/systemic reactions were assessed.

REPEVAX (Sanofi Pasteur MSD limited) is a combined low-dose diphtheria, tetanus, acellular pertussis, and inactivated poliomyelitis virus vaccine containing diphtheria toxoid (not less than 2 IU), tetanus toxoid (not less than 20 IU), pertussis antigens (pertussis toxoid (2.5 micrograms), filamentous haemagglutinin (5 micrograms), pertacti (3 micrograms), and fimbriae Types 2 and 3 (5 micrograms)), polio virus (inactivated) type 1 (40 D antigen units), poliovirus (inactivated type 2 (8 D antigen units), poliovirus (inactivated) type 3 (32 D antigen units), adsorbed on aluminum phosphate (1.5 mg (0.33 mg aluminum)) per 0.5-mL dose.

Immune responses to the diphtheria, tetanus, and pertussis components of REPEVAX (diphtheria toxoid, tetanus toxoid, pertussis toxoid, pertactin, fimbriae types 2 and 3 and filamentous haemagglutinin) were assessed using a multiplexed LUMINEX assay. Immune responses to poliovirus types 1, 2, and 3 were measured in virus neutralization assays. Sera obtained from all subjects in both groups were used in these assays.

For assessment of the immune response to bivalent rLP2086, functional antibodies were analyzed in hSBAs with the 4 primary MnB test strains described. Four primary MnB hSBA test strains (A22, A56, B44, and B24), 2 expressing LP2086 subfamily A and the other 2 expressing LP2086 subfamily B variants were selected. These 4 primary hSBA test strains (from 4 of the 6 fHBP phylogenetic subgroups and representing >90% of disease isolates circulating in the USA and Europe) were used for determination of the primary immunogenicity endpoints in this study. Additionally, the A22, B24, and B44 variants are epidemiologically relevant variants in Europe, while in the US, A22 and B24 are the most prevalent variants found expressed on disease causing MnB strains. The MnB hSBAs were validated prior to testing of samples used for the primary and secondary analyses.

Serum samples from 50% of randomly selected subjects in both groups had hSBA performed with A22 and B24 and the other 50% were tested with A56 and B44. These tests were performed on blood samples collected before Vaccination 1, after Vaccination 2, and after Vaccination 3.

The immunogenicity of REPEVAX is assessed by using prespecified criteria for each antigen defined in the pivotal Phase 3 clinical trials in adolescents that formed the basis of licensure for REPEVAX. The REPEVAX concomitant antigens include diphtheria, tetanus, pertussis toxoid, pertussis filamentous hemagglutinin, pertussis pertactin, pertussis fimbrial agglutinogens type 2+3, poliovirus type 1, poliovirus type 2, poliovirus type 3. The exception is for pertussis fimbrial agglutinogens (FIM) types 2+3, which defined a titer of ≥5 EU/mL in the assay used for licensure of REPEVAX. In this study the lower limit of quantification (LLOQ) of the pertussis FIM types 2+3 assay was ≥10.6 EU/mL, which is higher and therefore more stringent than the licensing criteria of REPEVAX.

The LLOQs for the concomitant antigens were 0.037 IU/mL for diphtheria toxoid; 0.05 IU/ml for tetanus toxoid; 0.9 EU/mL for pertussis toxoid; 2.9 EU/mL for pertussis filamentous hemagglutinin, 3.0 EU/mL pertussis pertactin; 10.6 EU/mL pertussis fimbrial agglutinogens type 2+3; 1:8 for poliovirus type 1, poliovirus type 2, poliovirus type 3.

Additional descriptive endpoints for the primary objective were the antibodies to concomitant vaccine antigens measured as geometric mean titer (GMTs) or geometric mean concentrations (GMCs) at postvaccination 1 (Visit 2).

Another endpoint was the proportion of subjects with hSBA titer ≥LLOQ at Postvaccination 3 (Visit 6) for each of the 4 primary MnB test strains.

Concomitant Vaccine Antigens.

The proportion of subjects achieving the prespecified criteria for the concomitant vaccine antigens 1 month after vaccination of diphtheria, tetanus, and pertussis acellular (dTaP)-IPV (REPEVAX) was computed with a 2-sided 95% exact (or Clopper-Pearson confidence limit) for Group 1 and Group 2. The difference (bivalent rLP2086/dTaP-IPV-dTaP-IPV, or Group 1-Group 2) of the proportions was also calculated along with a 2-sided 95% exact CI for the difference. Noninferiority was declared if the lower limit of the 2-sided 95% CI for the difference was greater than −0.10 (−10%) for all of the 9 antigens in the dTaP-IPV vaccine.

hSBAs with Primary Test Strains.

For each primary MnB hSBA test strain, the number and proportion of subjects achieving hSBA titers ≥LLOQ, ≥1:4, ≥1:8, ≥1:16, and ≥1:128 at each blood sampling time point were descriptively summarized along with the exact 2-sided 95% CI (or Clopper-Pearson confidence limit) for the proportion.

Results:

Of 749 subjects randomized, 685 (91.5%) included the evaluable immunogenicity population. Immune responses following REPEVAX+rLP2086 or REPEVAX+saline were noninferior for all 9 REPEVAX antigens. Immune responses to the bivalent rLP2086 vaccine were substantial after 2 doses and further enhanced after 3 doses (Table 3). Mild-to-moderate injection site pain was the most common local reaction; headache and fatigue were the most common systemic events. The proportion of subjects reporting an AE within 30 days postvaccination was similar (8.8% and 11.4%, for REPEVAX+rLP2086 and REPEVAX+saline, respectively).

For the concomitant vaccine evaluable immunogenicity population, the proportion of subjects achieving the pre-specified level of antibodies to concomitant vaccine antigens (threshold for response) 1 month after the REPEVAX dose was similar between the bivalent rLP2086+REPEVAX group and the REPEVAX alone group for concomitant vaccine antigens: diphtheria toxoid (99.4% in each group), tetanus toxoid (100% in each group), pertussis toxoid (94.7% and 96.0%, respectively), pertussis filamentous hemagglutinin (100% in each group), pertussis pertactin (100% in each group), pertussis fimbrial agglutinogens type 2+3 (97.6% and 98.9%, respectively), poliovirus type 1 (100% in each group), poliovirus type 2 (100% in each group), poliovirus type 3 (100% in each group).

Noninferiority was achieved because the lower bound of the 2-sided 95% CI for the difference in proportion of responders between the bivalent rLP2086+REPEVAX group (Group 1) and the REPEVAX alone group (Group 2), 1 month after the REPEVAX dose was greater than −0.10 (−10%) for the 9 antigens in REPEVAX (i.e., the lowest lower bound of the 95% CI on the proportion difference was −4.7% (pertussis toxoid). Hence, the immune response induced by REPEVAX given with bivalent rLP2086 was noninferior to the immune response induced by REPEVAX alone.

The proportion of subjects with an hSBA titer≥LLOQ for each of the 4 primary MnB test strains for the Postvaccination 3 evaluable immunogenicity population was assessed. The LLOQ for A22 was an hSBA titer equal to 1:16 while the LLOQ for all the other MnB test stains was an hSBA titer equal to 1:8.

For Group 1, the proportion of subjects with an hSBA titer ≥LLOQ at baseline (before Vaccination 1) was 14.4% for primary MnB strain A22, 18.2% for A56, 12.7% for B24, and 6.2% for B44. For Group 2, the proportion of subjects with an hSBA titer ≥LLOQ at baseline (before Vaccination 1) was 23.0% for primary MnB strain A22, 21.8% for A56, 12.9% for B24, and 6.3% for B44.

Substantial hSBA responses were observed among Group 1 subjects after Dose 2 of bivalent rLP2086, with additional increases observed after 3 doses 1 month after Vaccination 3. For Group 1 (bivalent rLP2086+REPEVAX), the proportion of subjects achieving an hSBA titer≥LLOQ at 1 month after Vaccination 2 and at 1 month after Vaccination 3 was 81.1% and 95.6% for A22, 97.3% and 100% for A56, 81.0% and 96.8% for B24, and 55.5% and 81.5% for B44. While substantial hSBA responses were achieved after only two bivalent rLP2086 doses, the increase in the proportion of subjects with an hSBA titer≥LLOQ after 2 doses (1 month after Vaccination 2) compared to 3 doses (1 month after Vaccination 3) exemplifies the enhancement of an immune response after 3 doses. In the control group (Group 2), the proportions of subjects with an hSBA titer≥LLOQ for each of the 4 primary MnB test strains at 1 month after Vaccination 2 and 1 month after Vaccination 3 were similar to the baseline hSBA results for each MnB test strain (before Vaccination 1).

For the 4 primary MnB test strains, the proportion of subjects in Group 1 exhibiting a defined hSBA titer was greater after 3 doses than after 2 doses. Subjects who achieved an hSBA titer of ≥1:16 are described, since this titer is a 4-fold increase from a 1:4 titer (a titer of ≥1:4 is widely recognized as the correlate of protection against IMD). For Group 1, the proportion of subjects with an hSBA titer of 1:16 at 1 month after Vaccination 2 was 81.8% for A22, 97.3% for A56, 68.0% for B24, and 53.4% for B44. One month after Vaccination 3, the proportion of subjects with an hSBA titer of 1:16 was 95.6% for A22, 100% for A56, 87.3% for B24, and 79.5% for B44.

In the control group (Group 2), the proportions of subjects exhibiting defined hSBA titers for each of the 4 primary MnB test strains at 1 month after Vaccination 2 and 1 month after Vaccination 3 were similar to the proportion of subjects with the defined hSBA titer at baseline (before Vaccination 1).

For Group 1, the proportion of subjects with an hSBA titer of 1:16 following 3 doses of bivalent rLP2086 demonstrated that the vaccine elicits a robust immune response when 3 doses of bivalent rLP2086 were administered.

hSBA Geometric Mean Titers (GMTs).

In general, the GMTs at baseline were below the hSBA LLOQs for both groups. For Group 1, hSBA GMTs at 1 month after Vaccination 2 were 35.5 for A22, 91.1 for A56, 15.9 for B24, and 14.6 for B44. The hSBA GMTs at 1 month after Vaccination 3 were 63.4 for A22, 151.5 for A56, 28.3 for B24, and 36.5 for B44.

For Group 1, the observed GMTs after 2 doses for subfamily A strains, as well as after 3 doses for subfamily B strains, were indicative of a robust immune response.

Reverse cumulative distribution curves (RCDCs) showing the distribution of hSBA titers for A22, A56, B24, and B44 were assessed. Results from the RCDCs in Group 1 showed that substantial immune responses were observed among Group 1 subjects after Vaccination 2 of bivalent rLP2086; however, the figures also showed the benefit of a third dose of bivalent rLP2086 as greater proportion of subjects achieved higher titers against the 4 MnB test strains. The effect was most pronounced for strain B44.

Conclusions:

When given concomitantly with bivalent rLP2086, REPEVAX induced immune responses that were noninferior to those elicited by REPEVAX alone. The bivalent rLP2086 vaccine induced robust bactericidal responses to four diverse MnB test strains, particularly to those representing subfamily B, that were greater after 3 doses than 2 doses. Concomitant administration was generally safe and well tolerated.

TABLE 3

Immune response to 4 heterologous MnB test strains after doses 2 and 3 of bivalent rLP2086

| | rLP2086 + REPEVAX | | | | Saline + REPEVAX | | | |
|---|---|---|---|---|---|---|---|---|
| | | | hSBA ≥ LLOQ | | | | hSBA ≥ LLOQ | |
| Strain [fHBP variant] Time point | $N^a$ | hSBA GMT (95% CI)$^c$ | $n^b$ (%) | (95% CI)$^d$ | $N^a$ | hSBA GMT (95% CI)$^c$ | $n^b$ (%) | (95% CI)$^d$ |
| PMB80 [A22] | | | | | | | | |
| Dose 2 | 154 | 35.5 (30.27, 41.61) | 126 (81.8) | (74.8, 87.6) | 166 | 11.2 (10.02, 12.46) | 36 (21.7) | (15.7, 28.7) |
| Dose 3 | 158 | 63.4 (55.29, 72.79) | 151 (95.6) | (91.1, 98.2) | 166 | 11.0 (9.92, 12.27) | 33 (19.9) | (14.1, 26.8) |
| PMB2001 [A56] | | | | | | | | |
| Dose 2 | 149 | 91.1 (78.00, 106.51) | 145 (97.3) | (93.3, 99.3) | 151 | 8.3 (6.76, 10.29) | 39 (25.8) | (19.1, 33.6) |
| Dose 3 | 148 | 151.5 (131.47, 174.59) | 148 (100.0) | (97.5, 100.0) | 152 | 8.5 (6.90, 10.54) | 40 (26.3) | (19.5, 34.1) |
| PMB2948 [B24] | | | | | | | | |
| Dose 2 | 153 | 15.9 (13.55, 18.55) | 124 (81.0) | (73.9, 86.9) | 167 | 4.8 (4.41, 5.19) | 20 (12.0) | (7.5, 17.9) |
| Dose 3 | 157 | 28.3 (24.49, 32.66) | 152 (96.8) | (92.7, 99.0) | 170 | 4.8 (4.41, 5.15) | 22 (12.9) | (8.3, 18.9) |
| PMB2707 [B44] | | | | | | | | |
| Dose 2 | 146 | 14.6 (11.6, 18.43) | 81 (55.5) | (47.0, 63.7) | 159 | 4.7 (4.24, 5.12) | 12 (7.5) | (4.0, 12.8) |
| Dose 3 | 146 | 36.5 (28.93, 46.18) | 119 (81.5) | (74.2, 87.4) | 159 | 4.7 (4.29, 5.24) | 13 (8.2) | (4.4, 13.6) |

GMT = geometric mean titer; hSBA = serum bactericidal assay using human complement; LLOQ = lower limit of quantitation (titer 1:16 for PMB80 [A22] and 1:8 for the other MnB test strains); rLP2086 = recombinant lipoprotein 2086.
$^a$Number of subjects with valid hSBA titers for the given strain
$^b$Number of subjects with hSBA titer ≥LLOQ for given strain at specified time point
$^c$Confidence intervals are back transformations of confidence intervals based on Student t distribution for the mean logarithm of the hSBA titers
$^d$Exact 2-sided confidence intervals based on observed proportion of subjects using the Clopper and Pearson method

Example 5

Immunogenicity of an Investigational Meningococcal Serogroup B Bivalent rLP2086 Vaccine in Healthy Adolescents Background and Aims:

Neisseria meningitidis serogroup B (MnB) causes invasive disease in infants, adolescents, and adults. A conserved, surface-exposed lipoprotein, LP2086 (a factor H binding protein [fHBP]), is a promising MnB vaccine target. Safety and immunogenicity of an investigational bivalent, recombinant vaccine (rLP2086) were studied in healthy adolescents (11-18 years).

Methods:

Subjects in this placebo-controlled, single-blind study were randomized to two 3-dose schedules and three 2-dose schedules. Each 120-μg dose contained 2 rLP2086 antigens, 1 from each LP2086 subfamily (A and B). Saline was given when vaccine was not scheduled. Serum bactericidal assays using human complement (hSBA) were performed with 4 MnB test strains (heterologous to vaccine fHBP).

Results:

1713 subjects (mean age, 14.4 y) were randomized. One month after 3 doses of vaccine, hSBA titers ≥8 to subfamily A and B strains were observed in 95-99% and 86-89% of subjects, respectively; after 2 doses, these numbers ranged from 91-100% and 69-77% of subjects, respectively. Of the 2-dose schedules, 0 and 6 months induced the highest antibody responses (Table 4). hSBA GMTs after 2 doses ranged from 6.2-125.6 and after 3 doses ranged from 25.6-155.6 across the 4 MnB heterologous test strains. Mild-to-moderate injection site pain was the most common local reaction. Fever ≥38° C. was experienced in 3.3-6.5% and 2.1% of rLP2086 and saline recipients, respectively, after dose 1.

TABLE 4

Proportion of Subjects Achieving hSBA Titer ≥8* for Each Strain 1 Month After Last Dose of Bivalent rLP2086

| | Group 1 (0, 1, 6 mo) | Group 2 (0, 2, 6 mo) | Group 3 (0, 6 mo) | Group 4 (0, 2 mo) | Group 5 (2, 6 mo) |
|---|---|---|---|---|---|
| Strain [fHBP variant] | n = 354-362 % (95% CI)$^\dagger$ | n = 352-359 % (95% CI)$^\dagger$ | n = 356-370 % (95% CI)$^\dagger$ | n = 234-240 % (95% CI)$^\dagger$ | n = 110-113 % (95% CI)$^\dagger$ |
| PBM80 [A22] | 91.7$^\ddagger$ (88.3, 94.3) | 95.0$^\ddagger$ (92.1, 97.0) | 93.5$^\ddagger$ (90.5, 95.8) | 90.8 (86.3, 94.1) | 91.9 (85.2, 96.2) |
| PBM2001 [A56] | 99.4$^\ddagger$ (98.0, 99.9) | 98.9$^\ddagger$ (97.2, 99.7) | 98.4$^\ddagger$ (96.5, 99.4) | 100.0 (98.5, 100.0) | 99.1 (95.2, 100.0) |
| PBM2948 [B24] | 89.0$^\ddagger$ (85.2, 92.0) | 88.4$^\ddagger$ (84.6, 91.8) | 81.1$^\ddagger$ (76.6, 85.0) | 73.0 (66.9, 78.5) | 69.1 (59.6, 77.6) |
| PBM2702 [B44] | 88.5$^\ddagger$ (84.7, 91.6) | 86.1$^\ddagger$ (82.0, 89.5) | 77.5$^\ddagger$ (72.2, 82.3) | 70.1 (63.8, 75.9) | 73.0 (63.7, 81.0) | hSBA = serum bactericidal assay using human complement.
*Lower limit of quantification for all strains = 8.
$^\dagger$Exact 2-sided confidence interval (Clopper and Pearson) based upon the observed proportion of subjects.
$^\ddagger$P < 0.001; values <0.0125 are considered significant. P values only apply to Groups 1, 2 and 3.

TABLE 2 hSBA GMTs for Each Strain 1 Month After Last Dose of Bivalent rLP2086

| Strain [fHBP variant] | Group 1 (0, 1, 6 mo) n = 354-362 GMT* (95% CI)† | Group 2 (0, 2, 6 mo) n = 352-359 GMT* (95% CI)† | Group 3 (0, 6 mo) n = 356-370 GMT* (95% CI)† | Group 4 (0, 2 mo) n = 234-240 GMT* (95% CI)† | Group 5 (2, 6 mo) n = 110-113 GMT* (95% CI)† |
|---|---|---|---|---|---|
| PBM80 [A22] | 55.1 (48, 87, 62, 07) | 56.3 (50.91, 62.27) | 48.4 (43.45, 53.86) | 14.2 (12.08, 16.73) | 39.6 (32.31, 48.46) |
| PBM2001 [A56] | 152.9 (137.23, 170.47) | 155.6 (140.39, 172.38) | 125.6 (112.59, 140.17) | 26.5 (22.24, 31.58) | 111.8 (92.73, 134.90) |
| PBM2948 [B24] | 29.1 (25.88, 32.66) | 25.6 (23.03, 28.45) | 20.6 (18.38, 23.18) | 8.0 (7.01, 9.24) | 14.7 (12.01, 18.01) |
| PBM2702 [B44] | 40.3 (35.16, 46.11) | 35.0 (30.63, 39.91) | 22.5 (19.60, 25.72) | 6.2 (5.52, 7.07) | 17.8 (14.12, 22.42) |

GMT = geometric mean titer; hSBA = serum bactericidal assay using human complement.
*GMTs were calculated using of subjects with valid and determinate hSBA at the given time point.
†CIs are back transformations of confidence levels based on the students distribution for the mean logarithm for the hSBA titers.

Conclusions:

rLP2086 was well tolerated. All dosing regimens yielded robust bactericidal responses that were most pronounced after 3 doses.

Table 4 is the same as Table 1 of Example 1, described above. Table 5 summarizes the hSBA GMTs and the corresponding CIs by study time for the evaluable immunogenicity population. GMTs increased from baseline (before Injection 1) and continued to increase with each subsequent dose of bivalent rLP2086.

For the 4 primary MnB strains, the GMTs were greater after 3 doses of bivalent rLP2086 (Groups 1 and 2) than after 2 doses (Groups 3, 4, and 5). The GMTs were similar between the two 3-dose groups, and they were similar among the three 2-dose groups.

Before injection 1 (baseline), hSBA GMTs for Groups 1, 2, 3, 4, and 5 were as follows: 7.1, 6.3, 6.4, 6.4, and 6.8 for A22, respectively; 6.8, 6.1, 6.7, 6.3, and 6.2 for A56, respectively; 5.3, 5.1, 5.0, 4.9, and 5.1 for B24, respectively; and 4.4, 4.5, 4.5, 4.6, and 4.4 for B44, respectively.

For Group 1 (0-, 1-, and 6-month), there was a substantial increase in GMTs noted 1 month after Dose 2 for all 4 primary MnB strains (24.4, 77.3, 13.8, and 13.1 for A22, A56, B24, and B44, respectively). The GMTs further increased after 3 doses of bivalent rLP2086 for Group 1 subjects for the 4 primary MnB test strains; 55.1 (A22); 152.96 (A56); 29.1 (B24); and 40.3 (B44).

For Group 2, similar increases in GMTs were noted after 2 and 3 doses of bivalent rLP2086. GMTs for Group 2 subjects after 2 doses of bivalent rLP2086 were 32.9 for A22; 94.6 for A56; 14.9 for B24; and 15.5 for B44. After 3 doses, the GMTs increased to 56.3 for A22; 155.6 for A56; 25.6 for B24; and 35.0 for B44.

For Groups 1 and 2, the observed GMTs after 2 doses for subfamily A strains, as well as after 3 doses for subfamily B strains, are indicative of a robust immune response.

For Group 3, small increases in GMTs were noted after 1 dose of bivalent rLP2086 as follows: 12.0 for A22; 18.5 for A56; 9.2 for B24; and 5.7 for B44. After 2 doses GMTs increased to 48.4 for A22; 125.6 for A56; 20.6 for B24; and 22.5 for B44.

For Group 4, GMTs were 13.3 for A22; 17.7 for A56; 9.8 for B24; and 5.9 for B44 after 1 dose of bivalent rLP2086. After 2 doses of bivalent rLP2086, GMTs were 37.1 for A22; 104.9 for A56; 17.7 for B24; and 19.1 for B44.

For Group 5, GMTs after 1 dose of bivalent rLP2086 were 16.0 for A22; 26.8 for A56; 12.6 for B24; and 6.8 for B44. After 2 doses of bivalent rLP2086, the GMTs increased to 39.6 for A22; 111.8 for A56; 14.7 for B24; and 17.8 for B44.

Taken together, for Groups 3, 4, and 5, the observed GMTs are indicative of an immune response for subfamily A and B strains after 2 doses of bivalent rLP2086.

In summary, 3 doses of bivalent rLP2086 provided a robust and the broadest immune response based on the hSBA titers for the 4 primary MnB test strains. In comparison to 2 doses, a higher proportion of subjects receiving 3 doses of bivalent rLP2086 achieved an hSBA titer ≥1:8 to the 4 primary MnB test strains.

The results following the 0-, 1-, and 6-month dosing schedule (Group 1) were similar to the results following the 0-, 2-, and 6-month dosing schedule (Group 2). For Groups 1 and 2, the post-Dose 3 GMT values achieved were higher than the post-Dose 2 GMT values. For Groups 1 and 2, the post-Dose 2 GMT values ranged from 24.4 to 94.6 for subfamily A strains and from 13.1 to 15.5 for subfamily B strains. The post-Dose 3 GMT values ranged from 55.1 to 155.6 for subfamily A strains and from 25.6 to 40.3 for subfamily B strains. For Groups 1 and 2, a higher proportion of subjects achieved an hSBA titer ≥1:8 to the 4 primary MnB test strains following 3 doses of bivalent rLP2086 when compared to the proportion of subjects achieving an hSBA titer ≥1:8 to the 4 primary MnB test strains after 2 doses of bivalent rLP2086.

Subjects who achieved an hSBA titer of ≥1:16 were also assessed. For Group 1, the percentage of subjects who achieved an hSBA titer of ≥1:16 one month after 2 doses of bivalent rLP2086 was 73.5% for A22; 96.3 for A56; 57.6 for B24; and 47.2% for B44. Following 3 doses of bivalent rLP2086, the percentage of subjects in Group 1 who achieved an hSBA titer of ≥1:16 was 91.4% for A22; 99.2% for A56; 82.8% for B24; and 84.8% for B44.

For Group 2, the percentage of subjects who achieved an hSBA titer of ≥1:16 one month after 2 doses of bivalent rLP2086 was 88.1% for A22; 97.9% for A56; 63.5% for B24; and 58.6% for B44. Following 3 doses of bivalent rLP2086, the percentage of subjects in Group 2 who achieved an hSBA titer of ≥1:16 was 95.0% for A22; 98.9% for A56; 83.6% for B24; and 83.8% for B44.

For Groups 1 and 2, the percentage of subjects achieving an hSBA titer of ≥1:16 following 3 doses of bivalent rLP2086 demonstrated that the vaccine elicits a robust immune response.

For Group 3, the percentage of subjects who achieved an hSBA titer of ≥1:16 after 2 doses of bivalent rLP2086 was 93.2% for A22; 98.4% for A56; 73.8% for B24; and 70.8% for B44.

For Group 4, the percentage of subjects who achieved an hSBA titer of ≥1:16 one month after 2 doses of bivalent rLP2086 was 90.8% for A22; 99.2% for A56; 67.1% for B24; and 64.5% for B44.

For Group 5, the percentage of subjects who achieved an hSBA titer of ≥1:16 after 2 doses of bivalent rLP2086 was 91.0% for A22; 99.1% for A56; 64.5% for B24; and 66.7% for B44.

For Groups 3, 4, and 5, the percentage of subjects achieving an hSBA titer of ≥1:16 demonstrated that the vaccine elicits a robust immune response to subfamily A strains following only 2 doses. However, 3 doses increases the robustness of response to subfamily B strains.

The percentage of subjects achieving an hSBA titer of ≥1:16 after 3 doses of bivalent rLP2086 shows that the vaccine elicits a robust and broad immune response to MnB strains expressing LP2086 variants that are different from the vaccine components.

Reverse cumulative distribution curves (RCDCs) showing the distribution of hSBA titers by study times were also assessed for the evaluable immunogenicity populations for each strain by group. The RCDCs show robust immune responses after 2 doses of bivalent rLP2086 subfamily A strains. Following the third dose of bivalent rLP2086, the area under the response curves increases for all 4 primary MnB test strains, thereby demonstrating the enhancement of the immune response after 3 doses of bivalent rLP2086.

The results from the primary and secondary immunogenicity endpoint analyses show that the vaccine can generate antibodies with significant hSBA activity against heterologous subfamily A and subfamily B variants of MnB. While the proportion of subjects achieving an hSBA titer ≥1:8 was higher after 2 or 3 doses of bivalent rLP2086, a large proportion of subjects achieved an hSBA titer ≥1:8 one month after 1 dose of bivalent rLP2086. See Group 5 for example.

For the 4 primary MnB test strains, the GMTs were greater after 3 doses of bivalent rLP2086 (Groups 1 and 2) than after 2 doses (Groups 3, 4, and 5). The GMTs were similar in the two 3-dose groups. The GMTs were also similar among the three 2-dose groups. These data also demonstrate robust hSBA responses after 3 doses of bivalent rLP2086 based on the percentages of subjects achieving an hSBA titer ≥1:16.

These data demonstrate that the final formulation of bivalent rLP2086 generates a robust immune response and is safe and well tolerated when given in 2 or 3 doses. Even 1 dose of bivalent rLP2086 provides a substantial immune response above baseline and is also safe and well tolerated. Overall, there was no clinically meaningful difference in the safety profile after 2 or 3 doses of bivalent rLP2086.

Example 6

Safety, Tolerability, and Immunogenicity of a Meningococcal Serogroup B Bivalent rLP2086 Vaccine in Healthy Adolescents Aged 11 to 18 Years in Three Phase 2, Randomized, Controlled Studies Background:

Neisseria meningitidis serogroup B (MnB) is a major cause of invasive meningococcal disease in adolescents. A conserved, surface-exposed lipoprotein, LP2086 (factor H binding protein [fHBP]), is a promising vaccine target to protect against invasive disease caused by MnB. Safety, tolerability, and immunogenicity of an investigational bivalent, recombinant MnB vaccine (including SEQ ID NO: 1 and SEQ ID NO: 2, 2.8 molar ratio polysorbate-80, 0.5 mg/ml aluminum, 10 mM histidine, and 150 mM sodium chloride, herein referred to throughout the Examples as "bivalent rLP2086") were examined in three phase 2, randomized, controlled studies in healthy adolescents 11-18 years of age.

Methods:

Study 1012 examined 5 vaccine regimens of bivalent rLP2086, whereas studies 1010 and 1011 evaluated a 3-dose schedule of bivalent rLP2086 vaccine given concomitantly with the TdaP-IPV and HPV-vaccines, respectively. Each dose of bivalent rLP2086 contained 60 μg of the rLP2086 subfamily A variant A05 and 60 μg of the rLP2086 subfamily B variant B01. To examine immunogenicity of bivalent rLP2086 in each of the three studies, serum bactericidal assays using human complement (hSBA) were performed with 4 MnB test strains expressing the heterologous fHBP variants A22, A56, B24 and B44, which were selected to represent relevant diversity of fHBP variability, as well as to provide a perspective on the breadth of the vaccine-elicited immune response against strain expressing epidemiologically prevalent fHBP variants. Adverse events and solicited local and systemic reactions were assessed.

Results:

82-100% of subjects in all 3 studies achieved hSBA titers above the lower limit of quantification (LLOQ) for each of the 4 MnB test strains 1 month after dose 3 (Table 6). Across the three studies, the majority of systemic events and local reactions were mild to moderate in severity; adverse events were generally not serious or related to the study vaccine.

Conclusions:

Serum bactericidal antibody titers above 1:4 protect against invasive meningococcal disease. The demonstration of hSBA titers ≥LLOQ to 4 MnB test strains, each heterologous to vaccine antigen, in each of these adolescent phase 2 studies, suggest that the bivalent rLP2086 vaccine provided a functional antibody response that may be broadly active against diverse MnB disease-associated strains. Vaccinations with the bivalent rLP2086 were generally well tolerated.

TABLE 6

Proportion of Subjects Achieving an hSBA Titer ≥LLOQ for Each fHBP Variant Expressed by Each Test Strain 1 Month After the Last Dose of the Bivalent rLP2086 Vaccine

| fHBP variant expressed | % of Subjects | | | |
|---|---|---|---|---|
| by hSBA test strain | A22 | A56 | B24 | B44 |
| Study 1012 (dosing regimen) | | | | |
| Group 1 (0, 1, 6 mo); n = 354-360 | 91.4 | 99.4 | 89.0 | 88.5 |
| Group 2 (0, 2, 6 mo); n = 352-359 | 95.0 | 98.9 | 88.4 | 86.1 |
| Group 3 (0, 6 mo); n = 356-370 | 93.2 | 98.4 | 81.1 | 77.5 |
| Group 4 (0, 2 mo); n = 234-240 | 90.8 | 100.0 | 73.0 | 70.1 |
| Group 5 (0, 4 mo); n = 110-113 | 91.0 | 99.1 | 69.1 | 73.0 |
| Study 1010 (dosing regimen: 0, 2, 6 mo) | | | | |
| rLP2086 + TdaP-IPV Vaccine; n = 146-158 | 95.6 | 100.0 | 96.8 | 81.5 |
| Study 1011 (dosing regimen: 0, 2, 6 mo) | | | | |
| rLP2086 + HPV Vaccine; n = 833-849 | 94.0 | 98.9 | 90.5 | 82.7 |
| rLP2086 + Saline; n = 847-848 | 96.3 | 99.4 | 92.6 | 85.7 |

LLOQ = lower limit of quantification;
fHBP = factor H binding protein;
hSBA = serum bactericidal assays using human complement;
TdaP-IPV Vaccine = Tetanus, Diphtheria, Pertussis, Polio Vaccine.
LLOQ = the lowest amount of an analyte in a sample that can be quantitatively determined.
hSBA titers ≥1:4 are a correlate of protection for invasive meningococcal disease.
hSBA titers ≥LLOQ are above the minimal correlate. LLOQ was 1:16 for A22; and 1:8 for A56, B24, and B44.

Example 7

Immunogenicity of a Meningococcal Serogroup B Bivalent rLP2086 Vaccine in Healthy Adolescents Aged 11 to 18 when Administered Concomitantly with Human Papillomavirus Vaccine This Phase 2, randomized, observer-blind, controlled study evaluated the immunogenicity of bivalent rLP2086 with or without coadministration with GARDASIL®, which is a quadrivalent vaccine against human papillomavirus (HPV4) (as also described in U.S. Pat. No. 5,820,870), in healthy adolescents ≥11 to <18 years of age. GARDASIL contains recombinant antigens of HPV type 6, 11, 16, and 18 (i.e., HPV-6, HPV-11, HPV-16, and HPV-18) L1 protein. An endpoint was the hSBA GMTs for each of the 4 primary MnB test strains at each applicable blood sampling time point.

Methods:

Subjects received bivalent rLP2086 (including SEQ ID NO: 1 and SEQ ID NO: 2, 2.8 molar ratio polysorbate-80, 0.5 mg/ml aluminum, 10 mM histidine, and 150 mM sodium chloride)+HPV4 (Group 1), bivalent rLP2086+saline (Group 2), or HPV4+saline (Group 3) at months 0, 2, and 6. Sera from subjects in Groups 1 and 2 before vaccination 1, and 1 month after vaccinations 2 and 3, were tested by serum bactericidal assay using human complement (hSBA) using 4 MnB test strains, each expressing an fHBP (A22, A56, B44, and B24) that is heterologous to the vaccine components and represents the breadth of fHBP diversity, as well as epidemiological prevalence. Endpoints assessed included the proportion of subjects with hSBA titers the lower limit of quantitation (LLOQ; 1:16 [A22] or 1:8 [A56, B44, B24]) and hSBA geometric mean titers (GMTs).

To demonstrate noninferiority of administrating GARDASIL plus bivalent rLP2086 compared to GARDASIL alone, immunogenicity assessments were performed with 2 hSBAs, using 1 primary test strain representing subfamily A variants (A22) and 1 primary test strain representing subfamily B variants (B24). However, all 4 primary MnB test strains were used for determination of additional bivalent rLP2086 immunogenicity/efficacy exploratory endpoints.

For assessment of the immune response to bivalent rLP2086, functional antibodies were analyzed in hSBAs with meningococcal serogroup B strains randomly selected from Pfizer's representative MnB SBA strain pool, as described in Example 2. The hSBAs measured the functional antibodies in human sera that in a complement-dependent manner kill the target meningococcal strain.

Results:

814 and 812 subjects included the evaluable immunogenicity population for Groups 1 and 2, respectively. Compared with before vaccination 1, the proportion of subjects with hSBA titers ≥LLOQ against all 4 test strains was higher after vaccinations 2 (55%-99%) and 3 (83%-99%; FIG. 1). Table 7 presents the hSBA GMTs for each of the 4 primary MnB strains and the corresponding CIs by sampling time point for the evaluable immunogenicity population. The GMTs at baseline were below the hSBA LLOQs for both groups. GMTs ranged from 11.1-70.6 and 11.9-76.3 after vaccination 1, and 25.8-117.2 and 28.0-128.2 after vaccination 2 in Groups 1 and 2, respectively (Table 7 below).

For the evaluable immunogenicity population, the hSBA GMTs to the 2 primary MnB strains at 1 month after the Vaccination 3 bivalent rLP2086 dose for Group 1 and Group 2 were as follows: 53.3 and 57.8, respectively for A22 and 25.8 and 28.0, respectively for B24.

For Group 2 (bivalent rLP2086+saline), hSBA GMTs at 1 month after Vaccination 2 were 33.7 for A22, 76.3 for A56, 16.3 for B24, and 11.9 for B44. The hSBA GMTs at 1 month after Vaccination 3 were 57.8 for A22, 128.2 for A56, 28.0 for B24, and 31.9 for B44.

For Group 1 (bivalent rLP2086+GARDASIL), hSBA GMTs at 1 month after Vaccination 2 were 31.9 for A22, 70.6 for A56, 15.0 for B24, and 11.1 for B44. The hSBA GMTs at 1 month after Vaccination 3 were 53.3 for A22, 117.2 for A56, 25.8 for B24, and 27.2 for B44.

Reverse cumulative distribution curves (RCDCs) showing the distribution of hSBA titers for A22, A56, B24, and B44 were assessed for Group 1 and Group 2 at all sampling time points for the evaluable immunogenicity population. The RCDCs showed that the majority of subjects responded after Vaccination 2 and had an additional increase in titer for the 4 primary MnB test strains after Vaccination 3. Immune responses to the antigens were similar for Groups 1 and 2.

Conclusions:

Bivalent rLP2086 can be administered with HPV4 without affecting the bactericidal response assessed by hSBA seroresponse or GMTs. Since hSBA titers ≥1:4 correlate with protection against meningococcal disease, these data indicate the potential for protection of adolescents against a broad range of MnB strains following administration of the bivalent rLP2086 in the setting of concomitant administration of HPV vaccine.

TABLE 7

| hSBA GMTs - Evaluable Immunogenicity Population | | | | |
|---|---|---|---|---|
| Strain [Variant] Sampling Time Point | Group 1 rLP2086 + HPV4 | | Group 2 rLP2086 + Saline | |
| | $n^a$ | $GMT^b$ (95% CI)$^c$ | $n^a$ | $GMT^b$ (95% CI)$^c$ |
| PMB80 [A22] | | | | |
| Before Vaccination 1 | 794 | 9.6 (9.3, 10.0) | 799 | 9.9 (9.5, 10.3) |
| 1 Month After Vaccination 2 | 794 | 31.9 (29.96, 33.94) | 801 | 33.7 (31.69, 35.85) |
| 1 Month After Vaccination 3 | 803 | 53.3 (50.22, 56.66) | 801 | 57.8 (54.44, 61.44) |
| PMB2001 [A56] | | | | |
| Before Vaccination 1 | 757 | 5.0 (4.78, 5.32) | 740 | 5.0 (4.75, 5.28) |

TABLE 7-continued hSBA GMTs - Evaluable Immunogenicity Population

| Strain [Variant] Sampling Time Point | Group 1 rLP2086 + HPV4 | | Group 2 rLP2086 + Saline | |
|---|---|---|---|---|
| | $n^a$ | $GMT^b$ (95% CI)$^c$ | $n^a$ | $GMT^b$ (95% CI)$^c$ |
| 1 Month After Vaccination 2 | 790 | 70.6 (66.17, 75.34) | 795 | 76.3 (71.93, 80.99) |
| 1 Month After Vaccination 3 | 796 | 117.2 (110.14, 124.76) | 802 | 128.2 (120.65, 136.27) |
| PMB2948 [B24] | | | | |
| Before Vaccination 1 | 801 | 4.3 (4.23, 4.46) | 793 | 4.5 (4.35, 4.65) |
| 1 Month After Vaccination 2 | 770 | 15.0 (13.88, 16.15) | 770 | 16.3 (15.15, 17.62) |
| 1 Month After Vaccination 3 | 788 | 25.8 (24.14, 27.56) | 793 | 28.0 (26.24, 29.87) |
| PMB2702 [B44] | | | | |
| Before Vaccination 1 | 806 | 4.1 (4.04, 4.15) | 805 | 4.2 (4.10, 4.31) |
| 1 Month After Vaccination 2 | 783 | 11.1 (10.21, 12.01) | 776 | 11.9 (10.94, 12.96) |
| 1 Month After Vaccination 3 | 799 | 27.2 (24.99, 29.68) | 795 | 31.9 (29.25, 34.82) |

GMT = geometric mean titer;
HPV4 = quadrivalent human papillomavirus vaccine;
hSBA = serum bactericidal assay using human complement.
$^a$n = number of subjects with valid and determinate hSBA titers for the given strain.
$^b$Geometric mean titers were calculated using all subjects with valid and determinate hSBA titers at the given time point.
$^c$Confidence intervals are back transformations of confidence intervals based on the Student t distribution for the man logarithm of the hSBA titers.

Example 8

Immunogenicity of Human Papilloma Vaccine Coadministered with a Bivalent rLP2086 Vaccine Against Meningococcal Serogroup B in Healthy Adolescents Background:

This Phase 2, randomized study evaluated coadministration of a quadrivalent vaccine against human papillomavirus (HPV4), with bivalent rLP2086, an investigational vaccine against invasive disease caused by Neisseria meningitidis serogroup B (MnB), in healthy adolescents ≥11 to <18 years of age.

Methods:

Subjects received HPV4+bivalent rLP2086 (Group 1), bivalent rLP2086+saline (Group 2), or saline+HPV4 (Group 3) at months 0, 2, and 6. Sera were collected at baseline and after doses 2 and 3 in all groups. Immune responses to HPV4 antigens (HPV-6, 11, 16, and 18) were determined by competitive LUMINEX immunoassays (cLIAs). Bivalent rLP2086 immunogenicity was measured by serum bactericidal assay using human complement (hSBA) with 2 MnB test strains expressing vaccine-heterologous fHBP variants (A22 and B24). Immunogenicity endpoints, all after dose 3, included: geometric mean titers (GMTs) against HPV antigens in Groups 1 and 3; hSBA GMTs for strains expressing variants A22 and B24 in Groups 1 and 2; and seroconversion rate for HPV antigens in baseline seronegative subjects in Groups 1 and 3. Safety of bivalent rLP2086 was also assessed after concomitant administration with HPV4 or saline.

Assessments of the immune response to GARDASIL (HPV type 6, 11, 16, and 18 L1 protein) were performed using cLIAs based on a fluorescently labeled microsphere-based platform (LUMINEX). Sera obtained from all subjects in Groups 1 and 3 prior to the first vaccination with GARDASIL (Visit 1) and 1 month after the third vaccination with GARDASIL (Visit 5) were used in these assays.

The comparison of the GMTs to the 4 HPV antigens for Group 1 and Group 3, with their corresponding GMT ratios (GMRs) of Group 1 to Group 3 and the 2-sided 95% Cls of the ratios is presented in Table 8. The criterion for the noninferiority margin was 1.5-fold, which corresponds to a value of 0.67 for the lower limit of the 2-sided 95% CI of the GMR. The 1.5-fold criterion of 0.67 was met for all the MnB test strains and the HPV antigens except for HPV-18, which had a lower bound 95% confidence interval (CI) of 0.62. In a separate analysis, ≥99% of subjects seroconverted to all 4 HPV antigens in both the Saline+HPV4 and rLP2086+ HPV4 groups.

Another objective of this study was to describe the immune response induced by bivalent rLP2086+GARDASIL (Group 1) and by saline+GARDASIL (Group 3), as measured by seroconversion in the HPV immunogenicity assays after the Vaccination 3 dose of GARDASIL (Visit 5) in both groups.

The seroconversion rate for each of the 4 HPV antigens, 1 month after the last dose of GARDASIL for subjects who were HPV-seronegative at baseline in Group 1 and Group 3, was calculated as the proportion of subjects with anti-HPV serum cLIA levels ≥20 mMU/ml for HPV-6, ≥16 mMU/ml for HPV-11, ≥20 mMU/ml for HPV-16, and ≥24 mMU/ml for HPV-18.

The number and proportion of baseline HPV-seronegative subjects achieving the prespecified criteria for seroconversion for the 4 HPV antigens with the corresponding 95% Cls in each group, the percent differences (Group 1-Group 3) in the proportion, and the 95% CIs of the differences are presented in Table 9 for the baseline HPV-seronegative evaluable immunogenicity population.

Results:

The prespecified noninferiority criteria set at 1.5-fold (0.67 lower limit of 95% CI for GMRs) were met for 3 of 4 HPV antigens (not HPV-18) and both MnB test strains (Table 8). Seroconversion rates in Groups 1 and 3 were ≥99% for all HPV antigens (Table 9). Greater local reactogenicity occurred after rLP2086 compared with saline but did not increase with later doses; injection site pain was the most common local reaction. Systemic events in all 3 groups were generally mild and moderate in severity.

For the evaluable immunogenicity population, the GMTs of antibodies to the 4 HPV antigens at 1 month after the GARDASIL dose at Vaccination 3 for Group 1 and Group 3 were as follows: 451.8 and 550.3, respectively (HPV-6); 892.9 and 1084.3, respectively (HPV-11); 3695.4 and 4763.4, respectively (HPV-16); and 744.0 and 1047.4, respectively (HPV-18). The GMRs of Group 1 to Group 3 at 1 month after the GARDASIL dose at Vaccination 3 were 0.82 for HPV-6 (95% CI: 0.72, 0.94), 0.82 for HPV-11 (95% CI: 0.74, 0.91), 0.78 for HPV-16 (95% CI: 0.68, 0.88), and 0.71 for HPV-18 (95% CI: 0.62, 0.81). Therefore, the lower limits of the 2-sided 95% CIs for anti-HPV GMRs for Group 1 compared with Group 3 were 0.72 for HPV-6, 0.74 for HPV-11, 0.68 for HPV-16, and 0.62 for HPV-18. The 1.5-fold criterion of 0.67 (the lower limit of the 2-sided 95% CI of the GMR) was met for all HPV antigens except for HPV-18, which had a lower bound of the 95% CI of 0.62.

The GMRs of the bivalent rLP2086+GARDASIL group to the bivalent rLP2086+saline group at 1 month after the Vaccination 3 bivalent rLP2086 dose were 0.92 for A22 (95% CI: 0.85, 1.00), and 0.92 for B24 (95% CI: 0.84, 1.01). The lower limits of the 2-sided 95% CIs for the hSBA GMRs for Group 1 compared with Group 2 were 0.85 for A22 and 0.84 for B24, which are both greater than 0.67 and therefore met the noninferiority margin of 1.5-fold.

The data from bivalent rLP2086+GARDASIL (Group 1) administration were compared to data from the bivalent rLP2086+saline (Group 2) administration by analyzing the hSBA titer 4-fold response rates for 2 primary MnB strains (A22 and B24) at 1 month after Vaccination 3 The proportions of subjects achieving ≥4-fold rise in hSBA titer from baseline to 1 month after Vaccination 3 for the 2 primary MnB strains were measured for both Group 1 subjects who received bivalent rLP2086+GARDASIL and Group 2 subjects who received bivalent rLP2086+saline. Of the subjects in Group 1, 85.3% exhibited ≥4-fold rise in hSBA titers against B24. Of the subjects in Group 2, 86.4% exhibited ≥4-fold rise in hSBA titers against A22, and 84.8% exhibited ≥4-fold rise in hSBA titers against B24.

The difference in the proportion of responders between Group 1 and Group 2 at 1 month after Vaccination 3 was −1.1% for A22 (95% CI: −4.6, 2.3) and −1.4% for B24 (95% CI: −5.1, 2.3). The differences of 4-fold response rates were all near a value of 1%, with the lower bounds of the 95% CI of the proportion difference being −4.6% A22 and −5.1% B24.

The noninferiority criteria of bivalent rLP2086+GARDASIL compared to saline+GARDASIL or compared to bivalent rLP2086+saline required that the lower limit of the 2-sided 95% CIs for the GMRs for antibodies to HPV for all 4 HPV antigens (HPV-6, HPV-11, HPV-16, and HPV-18) and for hSBA titers using 2 primary MnB test strains (A22 and B24) 1 month after Vaccination 3 be greater than 0.67. This prespecified criterion was met for both MnB test strains and at least 3 of the 4 HPV antigens. For HPV-18, the lower limit of the 2-sided CIs for the GMR was slightly below the prespecified threshold of 0.67, at 0.62.

The 4-fold rise responses to 2 primary MnB test strains (A22 and B24) were similar (ranged from 83.4% to 86.4%) between the group that received bivalent rLP2086+GARDASIL and the group that received bivalent rLP2086+saline.

The proportions of subjects in Groups 1 and 2 with prevaccination (i.e., before Vaccination 1) hSBA titers of ≥1:4 were 15.2% and 18.8%, respectively, for strain A22; 10.4% and 10.5%, respectively, for strain A56; 6.1% and 8.4%, respectively, for strain B24; and 1.7% and 3.2%, respectively for strain B44. In addition, the proportions of subjects in Groups 2 and 1 with prevaccination hSBA titers of ≥1:16 were 13.7% and 16.4%, respectively for strain A22; 9.0% and 9.1%, respectively, for strain A56; 4.1% and 5.4%, respectively, for strain B24; and 1.2% and 2.1%, respectively, for strain B44.

In Group 2 (bivalent rLP2086+saline), the proportion of subjects with an hSBA titer ≥1:4 at 1 month after Vaccination 2 was 86.3% for A22, 98.7% for A56, 77.1% for B24, and 60.1% for B44. One month after Vaccination 3, the proportion of subjects with an hSBA titer of ≥1:4 was 96.4% for A22, 99.4% for A56, 92.8% for B24, and 86.5% for B44. In Group 1 (bivalent rLP2086+GARDASIL), the proportion of subjects with an hSBA titer of ≥1:4 at 1 month after Vaccination 2 was 83.8% for A22, 97.8% for A56, 71.9% for B24, and 57.7% for B44. One month after Vaccination 3, the proportion of subjects with an hSBA titer of ≥1:4 was 94.3% for A22, 99.1% for A56, 91.1% for B24, and 84.4% for B44.

In Group 2 (bivalent rLP2086+saline), the proportion of subjects with an hSBA titer ≥1:16 at 1 month after Vaccination 2 was 85.8% for A22, 98.4% for A56, 68.8% for B24, and 49.9% for B44. One month after Vaccination 3, the proportion of subjects with an hSBA titer of ≥1:16 was 96.3% for A22, 99.4% for A56, 89.2% for B24, and 82.4% for B44. In Group 1 (bivalent rLP2086+GARDASIL), the proportion of subjects with an hSBA titer of ≥1:16 at 1 month after Vaccination 2 was 83.0% for A22, 97.2% for A56, 65.2% for B24, and 46.4% for B44. One month after Vaccination 3, the proportion of subjects with an hSBA titer of ≥1:16 was 94.0% for A22, 98.9% for A56, 86.3% for B24, and 78.0% for B44.

For both Group 1 and Group 2, a high proportion of subjects achieved an hSBA titer of ≥1:16 or greater following 2 or 3 doses of bivalent rLP2086, while most of the subjects had no measureable hSBA titer to any of the primary MnB test strains at prevaccination Visit 1.

For the baseline HPV-seronegative evaluable immunogenicity population, the proportion of subjects achieving the prespecified criteria for HPV seroconversion for the HPV antigens at 1 month after the GARDASIL dose at Vaccination 3 for the bivalent rLP2086+GARDASIL group (Group 1) and the saline+GARDASIL group (Group 3) were as follows: HPV-6 (99.4% and 99.3%, respectively), HPV-11 (99.6% and 99.5%, respectively), HPV-16 (99.6% and 99.5%, respectively), and HPV-18 (99.5% and 99.0%, respectively).

The difference in proportion of responders between the bivalent rLP2086+GARDASIL group (Group 1) and the saline+GARDASIL group (Group 3) at 1 month after the GARDASIL dose was 0.1% for HPV-6 (95% CI; −0.9, 1.5), 0.1% for HPV-11 (95% CI: −0.7, 1.3), 0.1% for HPV-16 (95% CI; −0.7, 1.3), and 0.5% for HPV-18 (95% CI; −0.6, 1.9).

For the bivalent rLP2086+GARDASIL group (Group 1) and the saline+GARDASIL group (Group 3), the seroconversion rate differences were within 0.1% and 0.5% across all 4 HPV antigens and the seroconversion rates were very similar across groups, with greater than 99% of subjects seroconverting for all 4 HPV antigens.

As an additional evaluation, bivalent rLP2086+GARDASIL (Group 1) was compared to bivalent rLP2086+saline (Group 2), by analyzing the hSBA titer 4-fold response rates for 2 primary MnB strains (A22 and B24) at 1 month after Vaccination 3. The proportions of subjects achieving an hSBA titer fold rise ≥4 from baseline to 1 month after Vaccination 3 for the 2 primary MnB strains are as follows: Of the subjects in Group 1, 85.3% exhibited ≥4-fold rise in hSBA titers against test strain A22, and 83.4% exhibited ≥4-fold rise in hSBA titers against test strain B24. Of the subjects in Group 2, 86.4% exhibited ≥4-fold rise in hSBA titers against test strain A22 and 84.8% exhibited ≥4-fold rise in hSBA titers against test strain B24.

The difference in the proportion of responders between Group 1 and Group 2 at 1 month after Vaccination 3 was −1.1% for A22 (95% CI: —4.6, 2.3) and −1.4% for B24 (95% CI: −5.1, 2.3). The differences of 4-fold response rate were all near a value of 1%, with the lower bounds of the 95% CI of the proportion difference being −4.6% (A22) and −5.1% (B24).

Immune Responses to Bivalent rLP2086.

Another objective of this study was to describe the immune response as measured by hSBA performed with 4 primary MnB test strains, 2 expressing LP2086 subfamily A proteins (A22 and A56) and 2 expressing LP2086 subfamily B proteins (B24 and B44), measured 1 month after the second visit (Visit 3) and the third (Visit 5) vaccinations with bivalent rLP2086.

One of the endpoints for this objective was the proportion of subjects with hSBA titers ≥LLOQ at 1 month after Vaccination 2 (Visit 3) and at 1 month after Vaccination 3 (Visit 5) for each of the 4 primary MnB test strains. The proportion of subjects with hSBA titer ≥LLOQ for each of the 4 primary MnB test strains for the evaluable immunogenicity population was assessed. The LLOQ for A22 was an hSBA titer equal to 1:16, while the LLOQ for all the other MnB test strains was an hSBA titer equal to 1:8.

For Group 2 (bivalent rLP2086+saline), the proportion of subjects with an hSBA titer ≥LLOQ at baseline (before Vaccination 1) was 16.4% for A22, 9.3% for A56, 6.9% for B24, and 2.5% for B44. For Group 2, the proportions of subjects achieving an hSBA titer ≥LLOQ at 1 month after Vaccination 2 and at 1 month after Vaccination 3 were 85.8% and 96.3%, respectively, for A22; 98.5% and 99.4%, respectively, for A56; 74.2% and 92.6%, respectively for B24; and 57.1% and 85.7%, respectively, for B44.

For Group 1 (bivalent rLP2086+GARDASIL), the proportion of subjects with an hSBA titer ≥LLOQ at baseline (before Vaccination 1) was 13.7% for A22, 9.2% for A56, 5.1% for B24, and 1.4% for B44. For Group 1, the proportions of subjects achieving an hSBA titer ≥LLOQ at 1 month after Vaccination 2 and at 1 month after Vaccination 3 were 83.0% and 94.0%, respectively, for A22; 97.5% and 98.9%, respectively, for A56; 70.6% and 90.5%, respectively for B24; and 54.5% and 82.7%, respectively, for B44.

Substantial hSBA responses to the 4 primary MnB test strains were observed among both Group 1 and Group 2 subjects at 1 month after Vaccination 2, with additional increases observed at 1 month after Vaccination 3.

The proportion of subjects achieving an hSBA titer fold rise ≥4 for each of the 4 primary MnB test strains and the proportions of subjects achieving the composite response for the evaluable immunogenicity population were assessed. The proportions of subjects with an observed hSBA titer ≥LLOQ for all 4 MnB strains combined at baseline (before Vaccination 1) were similar between Group 1 (0.3%) and Group 2 (0.7%).

For Group 2 (bivalent rLP2086+saline), the proportion of subjects achieving an hSBA titer fold rise ≥4 from baseline to 1 month after Vaccination 3 was 86.4% for A22, 95.3% for A56, 84.8% for B24, and 80.7% for B44, and 83.9% of subjects achieved a composite hSBA response (hSBA≥LLOQ for all 4 primary strains combined). At 1 month after Vaccination 2, the proportion of subjects achieving an hSBA titer fold rise ≥4 from baseline was 74.2% for A22, 92.6% for A56, 63.4% for B24, and 47.4% for B44, and 51.9% of subjects achieved a composite hSBA response.

For Group 1 (bivalent rLP2086+saline), the proportion of subjects achieving an hSBA titer fold rise ≥4 from baseline to 1 month after Vaccination 3 was 86.4% for A22, 95.3% for A56, 84.8% for B24, and 80.7% for B44, and 83.9% of subjects achieved a composite hSBA response (hSBA≥LLOQ for all 4 primary strains combined). At 1 month after Vaccination 2, the proportion of subjects achieving an hSBA titer fold rise ≥4 from baseline was 74.2% for A22, 92.6% for A56, 63.4% for B24, and 47.4% for B44, and 51.9% of subjects achieved a composite hSBA response.

Additional hSBA Fold Response.

Other endpoints were the proportion of subjects achieving at least 2-fold and 3-fold hSBA titer increases from baseline to each postvaccination blood sampling visit for each of the 4 primary MnB strains. Note that the LLOQ for A22 was an hSBA titer equal to 1:16, while the LLOQ for all the other MnB test strains was an hSBA titer equal to 1:8.

The proportion of subjects achieving a ≥2-fold rise in hSBA titer from baseline to 1 month after Vaccination 2 for Group 1 and Group 2 for MnB strains were 77.3% and 81.1%, respectively, for A22; 94.4% and 95.3%, respectively, for A56; 63.0% and 66.0%, respectively, for B24; and 46.1% and 48.6%, respectively, for B44. The proportions of subjects achieving an hSBA titer fold rise ≥2 from baseline to 1 month after Vaccination 3 for Group 1 and Group 2 for MnB strains were 90.2% and 92.8%, respectively, for A22; 97.2% and 97.9%, respectively, for A56; 84.6% and 87.2%, respectively, for B24; and 77.7% and 81.7%, respectively, for B44.

The proportions of subjects achieving an hSBA titer fold rise ≥3 from baseline to 1 month after Vaccination 2 for Group 1 and Group 2 for MnB strains were 73.1% and 74.2%, respectively, for A22; 92.5% and 92.6%, respectively, for A56; 61.3% and 63.4%, respectively, for B24; and 45.7% and 47.4%, respectively, for B44. The proportions of subjects achieving an hSBA titer fold rise ≥3 from baseline to 1 month after Vaccination 3 for Group 1 and Group 2 for MnB strains were 85.3% and 86.4%, respectively, for A22;

95.0% and 95.3%, respectively, for A56; 83.4% and 84.8%, respectively, for B24; and 77.0% and 80.7%, respectively, for B44.

In summary of the descriptive endpoints under the objectives, the majority of subjects achieved an hSBA titer ≥LLOQ for both Group 1 (bivalent rLP2086+GARDASIL) and group 2 (bivalent rLP2086+saline) for all 4 primary MnB test strains, while only a very small proportion of subjects had measurable hSBA titers≥LLOQ at baseline (prevaccination Visit 1). Substantial immune responses with the 4 MnB strains were observed at 1 month after Vaccination 2, with additional increases observed at 1 month after Vaccination 3 for both Group 1 and Group 2 subjects. This conclusion was confirmed by the proportion of subjects with an hSBA titer of ≥1:16 following 3 doses, the observed GMTs achieved after 2 doses and after 3 doses in both groups, and the RCDCs for the 4 primary MnB test strains.

For both Group 1 and Group 2, a high proportion of subjects achieved an hSBA titer fold rise ≥4 for each of the primary MnB test strains and a composite hSBA response LLOQ for all 4 primary MnB strains after the third study vaccination.

In addition, the majority of subjects achieved an hSBA titer fold rise ≥3 and an hSBA titer fold rise ≥2 for the 4 primary MnB strains at all sampling time points for both Group 1 (bivalent rLP2086+GARDASIL) and Group 2 (bivalent rLP2086+saline). The proportion of subjects with results meeting these criteria was higher after 3 vaccinations compared with 2 vaccinations.

These results support the evidence that the immune response to bivalent rLP2086 when coadministered with the HPV vaccine, GARDASIL, yields a robust immune response that is comparable to the immune response to bivalent rLP2086+saline.

HPV GMTs.

Table 9 presents the GMTs and the corresponding Cls for each of the 4 HPV antigens at 1 month after Vaccination 3 for Group 1 (bivalent rLP2086+GARDASIL) and Group 3 (saline+GARDASIL) in the evaluable immunogenicity population.

For Group 3, the HPV GMTs at baseline (before Vaccination 1) and at 1 month after Vaccination 3 were 6.0 and 550.3, respectively, for HPV-6; 4.3 and 1084.3, respectively, for HPV-11; 6.1 and 4763.4, respectively, for HPV-16; and 5.3 and 1047.4, respectively, for HPV-18. For Group 1 (bivalent rLP2086+GARDASIL), the HPV GMTs at baseline (before Vaccination 1) and at 1 month after Vaccination 3 were 5.8 and 451.8, respectively for HPV-6; 4.2 and 892.9, respectively, for HPV-11; 5.8 and 3695.4, respectively, for HPV-16; and 5.2 and 744.0, respectively, for HPV-18. Overall, the GMTs were numerically higher for Group 3 compared with Group 1. Reverse cumulative distribution curves (RCDCs) showing the distribution of titers for HPV-6, HPV-11, HPV-16, and HPV-18 were assessed for Group 1 (bivalent rLP2086+GARDASIL) and Group 3 (saline+GARDASIL) at all sampling time points for the evaluable immunogenicity population. The RCDCs showed robust immune responses among subjects after Vaccination 3 for both Group 1 and Group 3.

Summary of Immune Response to GARDASIL.

The GMTs to HPV antigens were numerically higher for Group 3 (saline+GARDASIL) as compared with Group 1 (bivalent rLP2086+GARDASIL), and the observed HPV GMTs after Vaccination 3 were indicative of a robust immune response for both groups. RCDCs also supported robust immune responses after Vaccination 3 for both Group 1 and Group 3. This was also supported by the proportion of subjects with seropositive status for the 4 HPV antigens, which was >99% at 1 month after Vaccination 3 for both groups. The younger age subgroup had higher HPV GMTs in Group 3 (saline+GARDASIL) than the older age subgroup. This difference was maintained when GARDASIL was given concomitantly with bivalent rLP2086.

Immunogenicity Conclusions.

The noninferiority criteria of bivalent rLP2086_GARDASIL compared to saline+GARDASIL or compared to bivalent rLP2086+saline required that the lower limit of the 2-sided 95% Cls for the geometric mean titer ratios (GMRs) for antibodies to HPV for all 4 HPV antigens (HPV-6, HPV-11, HPV-16, and HPV-18) and for hSBA titers using 2 primary MnB test strains (A22 and B24) 1 month after Vaccination 3 be greater than 0.67. This prespecified threshold was met for both MnB strains and 3 of the 4 HPV antigens. For HPV-18, the lower limit of the 2-sided 95% Cls for the GMR was slightly below the prespecified threshold of 0.67, at 0.62.

Seroconversion for all 4 HPV antigens was achieved by 99% or more of the subjects for the groups that received GARDASIL concomitantly with bivalent rLP2086 or with saline. The RCDCs for all 4 HPV antigens show that the majority of subjects achieved a response above the seroconversion threshold at 1 month after Vaccination 3. Robust GMTs relative to baseline were observed for both groups that received GARDASIL.

The 4-fold rise responses to 2 primary MnB test strains (A22 and B24) were similar (ranged from 83.4% to 86.4%) between the group that received bivalent rLP2086+GARDASIL (85.3% and 83.4%, respectively) and the group that received bivalent rLP2086+saline (86.4% and 84.8%, respectively).

Further descriptive analyses of the response to bivalent rLP2086 were performed using 4 primary MnB test strains (A22, A56, B24, and B44). A high proportion of subjects achieved an hSBA titer fold rise and the composite response (all 4 primary MnB test strains and the same immunogenicity/efficacy endpoint definition as used in the Phase 3 clinical program) for the evaluable immunogenicity population for both groups that received bivalent rLP2086, either concomitantly with GARDASIL (bivalent rLP2086+GARDASIL) or with saline (bivalent rLP2086+saline), 1 month after Vaccination 2 or 3. These responses are substantially higher than an hSBA titer ≥1:4 that has been demonstrated to correlate with protection against meningococcal disease including serogroup B disease. These results also indicate and support the evidence of a robust immune response to bivalent rLP2086 whether administered with saline or concomitantly with GARDASIL.

Conclusions:

Data indicate that robust immune responses to both vaccines were generated after concomitant administration of rLP2086+HPV4. Prespecified noninferiority criteria were met for 5 of 6 antigens. Although GMRs to HPV-18 narrowly missed noninferiority criteria, the high proportion of responders (≥99%) indicates clinical effectiveness is expected to be maintained after concomitant administration. Bivalent rLP2086 was well tolerated and elicited a robust immune response to test strains expressing fHBPs heterologous to those in the vaccine.

TABLE 8

Comparison of Geometric Mean Titers at 1 Month After Vaccination 3 (Evaluable Immunogenicity Population)

| Strain [Variant] | Group 1 rLP2086 + HPV4 | | Group 2 rLP2086 + Saline | | Group 3 Saline + HPV4 | | Ratio[d] |
|---|---|---|---|---|---|---|---|
| | n[a] | GMT[b] (95% CI)[c] | n[a] | GMT[b] (95% CI)[c] | n[a] | GMT[b] (95% CI)[c] | (95% CI)[e] |
| HPV antigens (Group 1 vs Group 3) | | | | | | | |
| HPV-6 | 813 | 451.8 (417.5, 489.0) | | NA | 423 | 550.3 (490.4, 617.6) | 0.82 (0.72, 0.94) |
| HPV-11 | 813 | 892.9 (839.5, 949.6) | | | 423 | 1084.3 (997.3, 1179.0) | 0.82 (0.74, 0.91) |
| HPV-16 | 813 | 3695.4 (3426.3, 3985.7) | | | 423 | 4763.4 (4285.9, 5294.2) | 0.78 (0.68, 0.88) |
| HPV-18 | 813 | 744.0 (687.7, 805.0) | | | 423 | 1047.4 (939.0, 1168.3) | 0.71 (0.62, 0.81) |
| hSBA strains (Group 1 vs Group 2) | | | | | | | |
| PMB80 [A22] | 803 | 53.3 (50.2, 56.7) | 801 | 57.8 (54.4, 61.4) | | NA | 0.92 (0.85, 1.00) |
| PMB2948 [B24] | 788 | 25.8 (24.1, 27.6) | 793 | 28.0 (26.2, 29.9) | | | 0.92 (0.84, 1.01) |

CI = confidence interval;
GMT = geometric mean titer;
HPV = human papillomavirus;
hSBA = serum bactericidal assay using human complement;
LLOQ = lower limit of quantitation; NA = not applicable.
Note:
LLOQ = 11 mMU/ml for HPV-6, 8 mMU/ml for HPV-11; 11 mMU/ml for HPV-16; and 10 mMU/ml for HPV-18. LLOQ = 1:16 for A22; 1:8 for A56, B24, and B44. Results below the LLOQ were set to 0.5 * LLOQ for analysis.
[a]n = number of subjects with valid and determinate assay results for the given antigen or strain.
[b]Geometric mean titers (GMTs) were calculated using all subjects with valid and determinate assay results at 1 month after Vaccination 3.
[c]Confidence intervals (CIs) are back transformations of confidence levels based on the Student t distribution for the mean logarithm of assay results.
[d]Ratios of GMTs (Group 1/Group 3 for HPV antigen titers and Group 1/Group 2 for hSBA strain titers).
[e]Confidence Intervals (CIs) for the ratio are back transformations of a confidence interval based on the Student t distribution for the mean difference of the logarithms of the measures(Group 1 - Group 3 for HPV titers and Group 1 - Group 2 for hSBA strain titers).

TABLE 9

Comparison of Subjects Achieving HPV Seroconversion at 1 Month After Vaccination 3 - Baseline HPV Seronegative Evaluable Immunogenicity Population

| Antigen | Seropositive Criteria | Group 1 rLP2086 + HPV4 | | | Group 3 Saline + HPV4 | | | Difference | |
|---|---|---|---|---|---|---|---|---|---|
| | | N[a] | n[b] (%) | (95% CI)[c] | N[a] | n[b] (%) | (95% CI)[c] | (%)[d] | (95% CI)[e] |
| HPV-6 | ≥20 mMU/mL | 802 | 797 (99.4) | (98.6, 99.8) | 414 | 411 (99.3) | (97.9, 99.9) | 0.1 | (−0.9, 1.5) |
| HPV-11 | ≥16 mMU/mL | 801 | 798 (99.6) | (98.9, 99.9) | 417 | 415 (99.5) | (98.3, 99.9) | 0.1 | (−0.7, 1.3) |
| HPV-16 | ≥20 mMU/mL | 800 | 797 (99.6) | (98.9, 99.9) | 413 | 411 (99.5) | (98.3, 99.9) | 0.1 | (−0.7, 1.3) |
| HPV-18 | ≥24 mMU/mL | 805 | 801 (99.5) | (98.7, 99.9) | 418 | 414 (99.0) | (97.6, 99.7) | 0.5 | (−0.6, 1.9) |

CI = Confidence interval; HPV = human papillomavirus.
[a]N = number of subjects with baseline HPV seronegative status for the given antigen.
[b]n = Number of subjects achieving seroconversion (prespecified criteria) at 1 month after Vaccination 3 for the given antigen.
[c]Exact 2-sided confidence interval (Clopper and Pearson) based upon the observed proportion of subjects.
[d]Difference in proportions, expressed as a percentage.
[e]Exact 2-sided confidence interval (based on Chan & Zhang) for the difference in proportions, expressed as a percentage.

Example 9

Bivalent rLP2086 Vaccine Efficacy

The efficacy of bivalent rLP2086 has been inferred using hSBA responses as the surrogate of efficacy and demonstration of serum bactericidal antibody responses to invasive *N. meningitidis* serogroup B (MnB) strains.

Four MnB strains, representative of invasive meningococcal disease (IMD) causing strains, were used in the evaluation. Each MnB test strain expresses an fHBP protein variant (A22, A56, B24 or B44) that is heterologous (differs) from the vaccine components (A05 and B01).

The efficacy of bivalent rLP2086 was assessed in 3 randomized controlled Phase II studies conducted in 4,459 adolescents aged 11 through 18 years of age in the US and Europe. See also Example 6. A total of 2,293 received at least 1 dose of 120 μg of bivalent rLP2086 using a 0-, 2-, and 6-month vaccination schedule. Efficacy was assessed by evaluating hSBA immune responses in subjects vaccinated with bivalent rLP2086.

Efficacy was inferred using 5 co-primary immunogenicity endpoints. For 4 of the 5 co-primary endpoints, pre-specified proportions of subjects had to achieve 4-fold rises in hSBA titer to each of the 4 MnB test strains following 3 doses of bivalent rLP2086. The fifth co-primary endpoint was a composite endpoint requiring that a prespecified high proportion of subjects each respond in all 4 hSBAs with the primary MnB test strains following 3 doses of bivalent rLP2086. Immune response was also assessed based on the proportion of subjects who achieved an hSBA titer≥the lower limit of quantitation (LLOQ) 1 month after the third dose of vaccine. LLOQ is defined as the lowest amount of the antibody in a sample that can be measured.

Study 1 (described in Example 7 and Example 8) was a Phase II, randomized, active-controlled, observer-blinded, multicenter trial in which 2,499 US subjects, 11 through 17 years of age, were randomly assigned (in a 2:2:1 ratio) to 1 of 3 groups: Group 1 received bivalent rLP2086+HPV4, Group 2 received bivalent rLP2086+Saline, and Group 3 received Saline+HPV4. All vaccinations were administered on a 0-, 2-, and 6-month schedule.

Study 2 (described in Example 4) was a Phase II, randomized, placebo-controlled, single-blind trial in which 753 European subjects, 11 through 18 years of age, were randomly assigned in a 1:1 ratio to 2 groups: Group 1 received bivalent rLP2086 at 0-, 2-, and 6-months and dTaP-IPV (diphtheria, tetanus, acellular pertussis-inactivated polio virus) at Month 0. Group 2 received Saline at 0-, 2-, and 6-months and dTaP-IPV at Month 0.

Study 3 (described in Example 5) was a Phase II, randomized, placebo-controlled, single-blind, multicenter trial in which 1,713 European subjects, 11 through 18 years of age, were randomly assigned in a 3:3:3:2:1 ratio to 5 groups. Subjects received 2 or 3 doses of bivalent rLP2086 administered on a 0-, 1-, and 6-month schedule (Group 1); on a 0-, 2-, and 6-month schedule (Group 2); on a 0- and 6-month schedule (Group 3); on a 0- and 2-month schedule (Group 4); or on a 0- and 4-month schedule (Group 5). Saline injections (1 or 2 doses depending on group) were administered in each group to maintain the blind.

Results in Studies 1, 2, and 3 among subjects who received a 3-dose series of bivalent rLP2086 at 0-, 2-, and 6-months are described above in the respective Examples 4-8. Evaluation of the 4-fold and composite response rates were exploratory endpoints for all studies. The 4-fold response rates showed that the lower bounds of the 95% Confidence Interval (CI) for all 4 endpoints were similar among the 3 studies and consistently met the threshold limits for the Phase III endpoints. The proportion of subjects achieving hSBA titer ≥LLOQ was similar across the 3 studies.

Based on the hSBA data acquired following 2 administrations of the vaccine given 1 or 2 months apart, 2 doses of vaccine administered over these intervals may provide protection to individuals at increased risk, due to potential exposure to a case of meningococcal serogroup B disease. The responses observed after 2 vaccine administrations delivered 1 or 2 months apart showed that a proportion of subjects expressed hSBA levels equal to or above the LLOQ values for each of the 4 primary test strains (see Study 1 results for Group 1 and Group 2; see Study 2 results for Group 1; see Study 3 results for Group 2). A third dose of the vaccine, administered at 6 months, can achieve vaccine-mediated protection.

Concomitant Vaccine Administration.

Study 1 (described in Example 7 and Example 8) evaluated the concomitant use of bivalent rLP2086 and HPV4 in US adolescents. The study endpoints included noninferiority assessment of the immune response for the four HPV4 antigens (based on geometric mean titer [GMT]) and for bivalent rLP2086 (based on hSBA using two MnB test strains [variants A22 and B24]) 1 month after the third vaccination. HPV4 immune response was also evaluated by seroconversion for each of the 4 HPV antigens.

Study 1 shows the comparison of the geometric mean titers (GMTs) of the antibodies to HPV antigens for Group 1 (bivalent rLP2086+HPV4) and Group 3 (Saline+HPV4), with their corresponding GMT ratio (GMRs) between Group 1 and Group 3 and the 2-sided 95% CIs of the ratios. Study 1 also provides the comparison of hSBA GMTs to the 2 primary MnB test strains for Group 1 and Group 2 with their corresponding GMRs between Group 1 and Group 2 and the 2-sided 95% CI of the ratios. The criterion for noninferiority margin was 1.5-fold, which corresponds to a value of 0.67 for the lower limit of the 2-sided 95% CI of the GMR. The 1.5-fold criterion of 0.67 was met for all the MnB test strains and the HPV antigens except for HPV-18, which had a lower bound 95% confidence interval (CI) of 0.62. Although the response to HPV-18 did not meet the pre-specified noninferiority criterion, the difference was marginal. In a separate analysis, ≥99% of subjects seroconverted to all 4 HPV antigens in both the Saline+HPV4 and bivalent rLP2086+HPV4 groups.

Example 10

Bivalent rLP2086 Elicits Antibodies in Individuals that Provide Broad Coverage Against MnB Strains Expressing Prevalent and Outbreak-Associated fHBP Variants Bactericidal antibodies measured in serum bactericidal assays using human complement (hSBAs) have been correlated with protection from meningococcal disease and hSBA responses have been used routinely as surrogates of vaccine efficacy. Global epidemiological studies of fHBP diversity revealed that ~80% of meningococcal disease is caused by strains that express one of 10 prevalent fHBP variants.

Methods:

hSBA responses to *Neisseria meningitidis* serogroup B (MnB) strains expressing the 10 most prevalent fHBP variants in the US and Europe (B24, B16, B44, A22, B03, B09, A12, A19, A05 and A07) in individual human subjects immunized with bivalent rLP2086 were evaluated. MnB strains expressing these ten most prevalent variants represent the breadth of fHBP diversity, including 5 of the 6 major fHBP subgroups, that are representative of >98% and 97% of strains (by subgroup) in the MnB SBA strain pool, and US subset of the MnB SBA strain pool, respectively. Twenty-three MnB test strains were obtained from Pfizer's MnB SBA strain pool (N=1263) that represent strains systematically collected from the US and Europe between the years 2000 and 2006. In addition, isolates from recent MnB disease outbreaks were included in the analysis. Matched prevaccination and postvaccination sera (postdose 2 and postdose 3) were obtained randomly from adolescent and young adult subjects enrolled in clinical studies B1971005, B1971012 or B1971003.

To provide additional information supporting the potential coverage afforded by vaccination with bivalent rLP2086, hSBAs were performed with the outbreak strains and serum samples from nine subjects immunized with bivalent rLP2086 (clinical study B1971012, described in Example 5 and Example 6. The subjects (11 to <19 years of age) had received 3 doses of bivalent rLP2086 at 0, 2 and 6 months. To ensure a conservative hSBA assessment the nine subjects were selected in a non-biased manner from a set of subjects with no baseline hSBA activity against the primary MnB test strains. Two of the clonal Princeton University outbreak strains (PMB5021 and PMB5025) and two of the UCSB outbreak strains (one from each of the two genetic clusters, PMB4478 and PMB4479, were tested.

Genetic characterization of the clonal Princeton University MnB Outbreak Strains is as follows: data suggest that the Princeton University outbreak strains are clonal. Each of the strains was typed as CC41/44 (ST 409) and expressed fHBP variant B153 (SEQ ID NO: 6). The strains had identical allele assignments for NHBA (2), porA (subtype P1.5-1, 2-2) and porB (3-82), all were null for nadA, and all had the same pulsed field gel electrophoresis (PFGE) profile (429).

Genetic characterization of the 2013 University of California Santa Barbara Outbreak Strains is as follows: The UCSB strains were typed as CC32(ET5; ST32), expressed fHBP variant B24, and are related to the Oregon clone that has been associated with hyperendemic serogroup B disease since 1993. Unlike the Princeton outbreak group of strains, the UCSB strains segregated genetically into two distinct clusters that were differentiated by their PFGE profile (468 or 467) and porB type (3-461 or 3-24). The strains had identical allele assignments for NadA (1), NHBA (5), porA (subtype P1.7, 16-20)

hSBA titers at baseline for all subjects and all outbreak strains were <4, indicating that the subjects had no protective antibodies to any of the outbreak strains prior to immunization with bivalent rLP2086.

Figure 2:
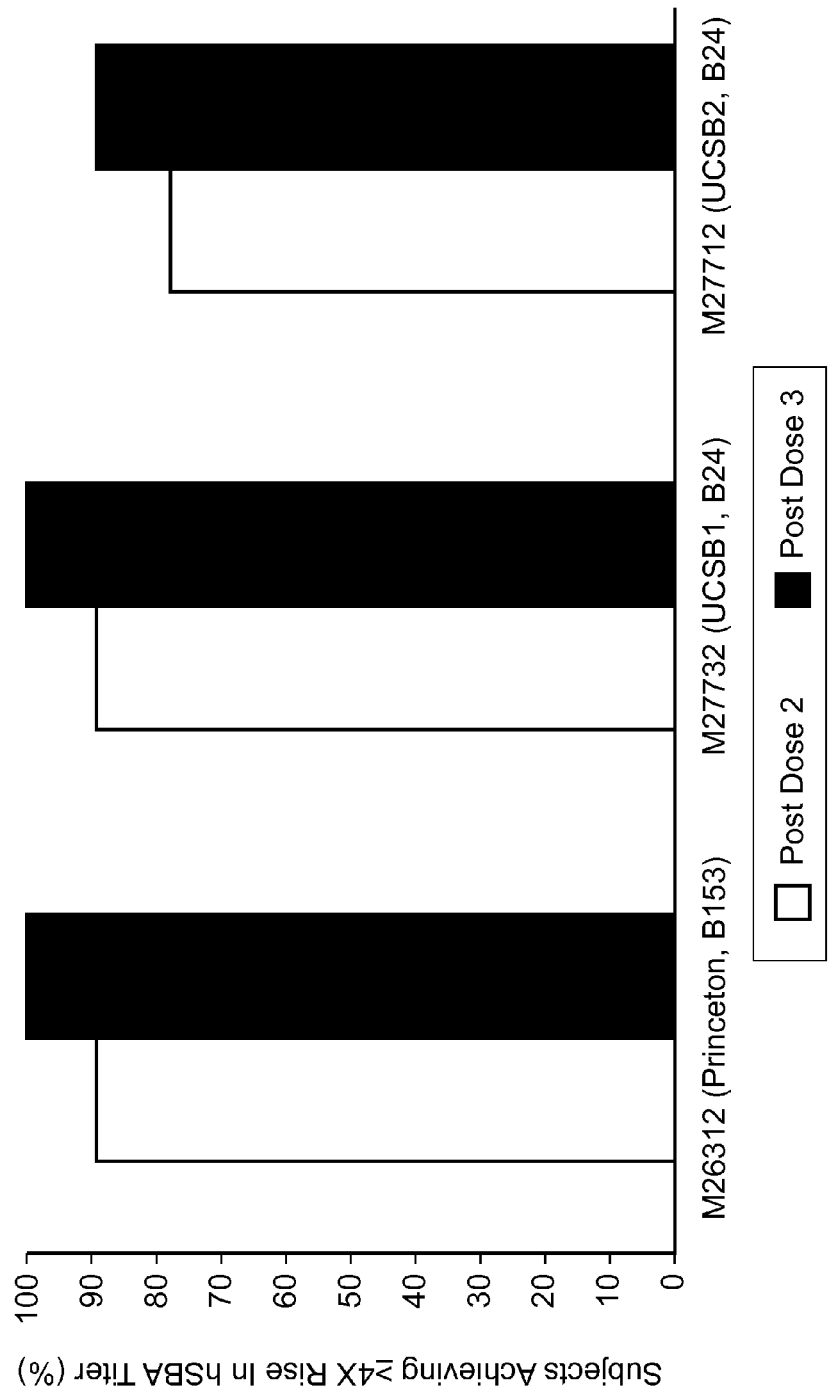
FIG. 2—Percentage of subjects achieving 4× rise in hSBA titers to Princeton University Outbreak Strains and UCSB Outbreak Strains of Individual Human Subjects Following Immunization With rLP2086 (Study B1971012—described in Example 5, Example 6). Serum samples from nine human subjects immunized with bivalent rLP2086 in clinical study B1971012 were evaluated in exploratory hSBAs using MnB outbreak strains from Princeton University and from UCSB. See Example 9.

Results:

All 23 MnB strains were susceptible in hSBA with sera from individual subjects immunized with bivalent rLP2086. Strains representing all 10 prevalent fHBP variants as well as additional strains were all killed by hSBA. Baseline hSBA seroprotection rates (proportions of subjects achieving hSBA titers≥1:4) were generally low. The lower seroprotective rates observed in subjects before immunization with bivalent rLP2086 exemplify the vulnerability of a non-vaccinated adolescent or young adult population to MnB disease. However, robust seroprotection rates were observed in adolescents and young adults with postvaccination sera: seroprotection rates >70% were observed for 83% of these strains depending on MnB strains and population tested. Postvaccination seroprotection rates for strains expressing the most prevalent subfamily A and B fHBP variants, B24 and A22, ranged from 81.0% to 100%, and 77.8% to 100% for recent outbreak strains expressing fHBP variants B24 and B153. Furthermore, robust postdose 2 responses (compared to baseline) to all outbreak strains were observed in these subjects, ranging from 56 to 89% depending on the outbreak strain used in the hSBA. In contrast, prevaccination seroprotective rates were low, or not detectable, for recent US outbreak strains. The hSBA responses to the Princeton University and UCSB outbreak strains are shown in FIG. 2.

Conclusions:

Bivalent rLP2086 elicits robust seroprotective hSBA responses in individuals to diverse invasive MnB strains expressing prevalent fHBPs in the US and Europe, as well as newly emerging variants (B153)(SEQ ID NO: 6). The proportion of subjects that showed a seroprotective response after immunization with bivalent rLP2086 greatly exceeded the proportion of subjects that was seroprotected at baseline. The data support that bivalent rLP2086 has the potential to provide broad protection of adolescents and young adults from invasive meningococcal serogroup B disease, including disease from recent outbreaks.

> B153

(SEQ ID NO: 6)

CSSGGGGVAADIGAGLADALTAPLDHKDKGLQSLTLDQSVRKNEKLKLAA

QGAEKTYGNGDSLNTGKLKNDKVSRFDFIRQIEVDGQLITLESGEFQVYK

QSHSALTALQTEQVQDSEDSGKMVAKRQFRIGDIAGEHTSFDKLPKGGSA

TYRGTAFGSDDAGGKLTYTIDFAAKQGHGKIEHLKSPELNVDLAAAYIKP

DEKHHAVISGSVLYNQDEKGSYSLGIFGGKAEEVAGSAEVKTVNGIRHIG

LAAKQ

---

What is claimed is:

1. A method of inducing a bactericidal immune response against a *Neisseria meningitidis* serogroup B subfamily A strain and against a *Neisseria meningitidis* serogroup B subfamily B strain in a human, comprising administering to the human an effective amount of a composition, said composition comprising
   a) a first lipidated polypeptide comprising the amino acid sequence set forth in SEQ ID NO: 1, and
   b) a second lipidated polypeptide comprising the amino acid sequence set forth in SEQ ID NO: 2.

2. The method according to claim 1, wherein the composition further comprises polysorbate-80, aluminum, histidine, and sodium chloride.

3. The method according to claim 1, wherein the immune response against the *Neisseria meningitidis* serogroup B subfamily A strain is greater than the immune response against the *Neisseria meningitidis* serogroup B subfamily B strain.

4. The method according to claim 1, wherein the immune response against the *Neisseria meningitidis* serogroup B subfamily A strain in the human comprises a bactericidal titer that is greater than the bactericidal titer against the *Neisseria meningitidis* serogroup B subfamily B strain in the human.

5. The method according to claim 1, wherein the composition induces a bactericidal immune response against any one of *N. meningitidis* serogroup B A22, A56, B24, B44 strains, or any combination thereof.

6. The method according to claim 1, wherein the composition induces a bactericidal immune response against any one of *N. meningitidis* serogroup B B24, B16, B44, A22, B03, B09, A12, A19, A05, A07, B153 strains, or any combination thereof.

7. A method of inducing a bactericidal immune response against a *Neisseria meningitidis* serogroup B strain expressing B153 factor H binding protein in a human, comprising administering to the human an effective amount of a composition, said composition comprising
   a) a first lipidated polypeptide comprising the amino acid sequence set forth in SEQ ID NO: 1, and
   b) a second lipidated polypeptide comprising the amino acid sequence set forth in SEQ ID NO: 2.

8. The method according to claim 7, wherein the composition further comprises polysorbate-80, aluminum, histidine, and sodium chloride.

* * * * *